(12) United States Patent
Poirier et al.

(10) Patent No.: US 8,653,054 B2
(45) Date of Patent: Feb. 18, 2014

(54) 2-(N-SUBSTITUTED PIPERAZINYL) STEROID DERIVATIVES

(75) Inventors: Donald Poirier, Quebec (CA); Jenny Roy, Quebec (CA); Rene Maltais, Quebec (CA)

(73) Assignee: Universite Laval, Quebec (CA)

( * ) Notice: Subject to any disclaimer, the term of this patent is extended or adjusted under 35 U.S.C. 154(b) by 0 days.

(21) Appl. No.: 13/130,621

(22) PCT Filed: Nov. 25, 2009

(86) PCT No.: PCT/CA2009/001726
§ 371 (c)(1),
(2), (4) Date: Sep. 7, 2011

(87) PCT Pub. No.: WO2010/060215
PCT Pub. Date: Jun. 3, 2010

(65) Prior Publication Data
US 2011/0312926 A1    Dec. 22, 2011

Related U.S. Application Data

(60) Provisional application No. 61/117,837, filed on Nov. 25, 2008.

(51) Int. Cl.
*A61K 31/58* (2006.01)
*C07J 41/00* (2006.01)

(52) U.S. Cl.
USPC .......................................... 514/176; 540/106

(58) Field of Classification Search
USPC .......................................... 540/106; 514/176
See application file for complete search history.

(56) References Cited

PUBLICATIONS

Roy, et al., 2β-(N-Substituted Piperazino)-5α-Androstane-3α, 17β-Diols: Parallel Solid-Phase Synthesis and Antiproliferative Activity on Human Leukemia HL-60 Cells, J. Comb. Chem., 9 (2007), pp. 347-358.
Thibeault, D., et al., Chemical Synthesis of 2β-amino-5α-Androstane-3α, 17β-Diol N-Derivatives and their Antiproliferative Effect on HL-60 Human Leukemia Cells, Bioorg. Med. Chem, 16 (2008), pp. 5062-5077.
Thibeault, D., et al., An Efficient Method for the Regioselective Aminolysis of 2,3α-Steroidal Expoxide, Synlet, 2003, pp. 1192-1194.
He, Q., et al., The Effects and Mechanisms of a Novel 2-Aminosteroid on Murine WEHI-3B Leukemia Cells In Vitro and In Vivo, Leukemia Research, 25 (2001), pp. 455-461.
He, Q., et al., A Novel Aminosteroid is Active for Proliferation Inhibition and Differentiation Induction of Human Acute Myeloid Leukemia HL-60 Cells, Leukemia Research, 23 (1999), pp. 369-372.
Robert et al., "Multidrug Resistance Reversal Agents," Journal of Medicinal Chemistry, Nov. 2003, pp. 4805-4817, vol. 46, No. 23.
Taplin, "Drug Insight: role of the androgen receptor in the development and progression of prostate cancer," Nature Clinical Practice, Apr. 2007, pp. 236-244, vol. 4, No. 4.
Chowdhury et al., "Chemotherapy for the treatment of hormone-refractory prostate cancer," Int J Clin Pract, Dec. 2007, pp. 2064-2070, vol. 61, No. 12.
McGuire et al., "Cyclophosphamide and Cisplatin Compared with Paclitaxel and Cisplatin in Patients With Stage III and Stage IV Ovarian Cancer," The New England Journal of Medicine, Jan. 1996, pp. 1-6, vol. 334, No. 1.
Parmar et al., (The International Collaborative Ovarian Neoplasm (ICON) Group), "Paclitaxel plus carboplatin versus standard chemotherapy with either single-agent carboplatin or cyclophosphamide, doxorubicin, and cisplatin in women with ovarian cancer: the ICON3 randomised trial," The Lancet, Aug. 2002, pp. 505-515, vol. 360.
Armstrong et al., "Intraperitoneal Cisplatin and Paclitaxel in Ovarian Cancer," The New England Journal of Medicine, Jan. 2006, pp. 34-43, vol. 354, No. 111.
Harrison, "Molecular Mechanisms of Drug Resistance in Tumours," Journal of Pathology, 1995, pp. 7-12, vol. 175.
Stavrovskaya, "Cellular Mechanisms of Multidrug Resistance of Tumour Cells," Biochemistry (Moscow), 2000, pp. 95-106, vol. 65, No. 1.
Huggins et al., "Studies on Prostatic Cancer: I. The Effect of Castration, of Estrogen and of Androgen Injection on Serum Phosphatases in Metastatic Carcinoma of the Prostate," Cancer Research, 1941, pp. 293-297.
Rasmusson, "Chapter 18. Chemical Control of Androgen Action," Annual Reports in Medicinal Chemistry, 1986, pp. 179-188, vol. 21.
McGuire et al., "Estrogen Receptors in Human Breast Cancer: An Overview," Estrogen Receptors in Human Breast Cancer, 1975, pp. 1-7, Raven Press, New York, NY.
Dickson et al., "Estrogenic Regulation of Growth and Polypeptide Growth Factor Secretion in Human Breast Carcinoma," Endocrine Reviews, 1987, pp. 29-42, vol. 8, No. 1.
Labrie et al., "Down-Staging of Early Stage Prostate Cancer Before Radical Prostatectomy: the First Randomized Trial of Neoadjuvant Combination Therapy with Flutamide and a Luteinizing Hormone-Releasing Hormone Agonist," Urology Symposium, Dec. 1994, pp. 29-37, vol. 44, No. 6A.
Labrie et al., "Major impact of hormonal therapy in localized prostate cancer-death can already be exception," Journal of Steroid Biochemistry & Molecular Biology, 2004, pp. 327-344, vol. 92.
Labrie et al., "Complete Androgen Blockade for the Treatment of Prostate Cancer 10," Important Advances in Oncology 1985, 1985, p. 193, J. B. Lippincott Company, Philadelphia, PA.
Chari, "Targeted Cancer Therapy: Conferring Specificity to Cytotoxic Drugs," Accounts of Chemical Research, Jan. 2008, pp. 98-107, vol. 41, No. 1.

*Primary Examiner* — Barbara P Badio
(74) *Attorney, Agent, or Firm* — Dentons US LLP

(57) ABSTRACT

Novel chemical agents are described herein. More specifically, 2-(N-substituted piperazinyl) pregnane and 2-(N-substituted piperazinyl) androstane derivatives exhibiting cytotoxicity on a variety of cancer cell lines are disclosed herein.

10 Claims, 1 Drawing Sheet

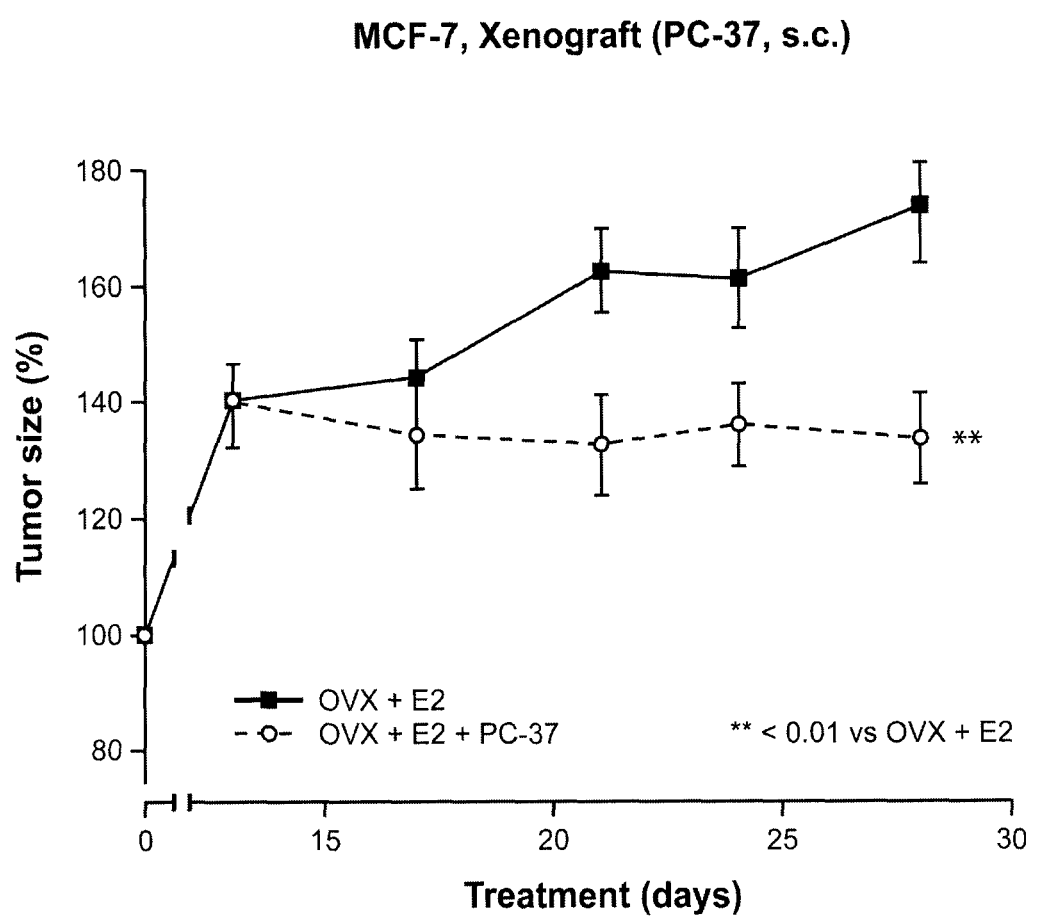

2-(N-SUBSTITUTED PIPERAZINYL) STEROID DERIVATIVES

The present application is a U.S. National Phase Application of International Application No. PCT/CA2009/001726, filed Nov. 25, 2009, which claims the benefit of U.S. Provisional Application 61/117,837, filed Nov. 25, 2008, both of which are hereby incorporated by reference in their entirety.

FIELD

The present disclosure relates to 2-(N-substituted piperazinyl) steroid derivatives. More specifically, but not exclusively, the present disclosure relates to 2-(N-substituted piperazinyl) steroid derivatives, their preparation and their use as pharmaceutical agents.

BACKGROUND

Cancer is a disease state characterized by the uncontrolled proliferation of genetically altered tissue cells. There have been several chemotherapeutic approaches developed to target cancer. These include alkylating and anti-mitotic agents, anti-metabolites and anti-tumor antibiotics. Such therapeutic agents act preferentially on rapidly proliferating cells such as cancer cells.

The utility of most of the anti-tumor agents currently in clinical use is limited by their inherent toxicity on normal healthy cells. Moreover, these agents often exhibit a low therapeutic index which further limits their medical utility. Furthermore, in view of their low therapeutic index, such agents are frequently administered at dosages encroaching the patient tolerable limit in order to achieve any significant therapeutic effect.

Breast and Prostate Cancer

Steroidal hormones play an important role in the growth of androgen and estrogen sensitive cancers, both of which account for about 35% of all cancers on men and women in Canada [1-3]. Inhibiting the action of these steroids by blocking their respective receptors has led to the development of numerous candidate therapies. The implementation of some these therapies has led to promising results, particularly in the treatment of prostate cancer (use of an anti-androgen in combination with a LHRH agonist) and breast cancer (anti-estrogen) [4]. However, drug resistance is observed following prolonged periods of exposure to such therapies, such that an evolution toward hormone independence is observed [5]. In such cases, classical chemotherapy (e.g. Doxorubicin) with its numerous side-effects becomes the treatment of choice in order to halt the evolution of the disease [6].

Ovarian Cancer

Ovarian cancer affects more than 200,000 women around the world, making it the $7^{th}$ most common type of cancer [7]. In North America alone, more than 25,000 women are diagnosed annually with ovarian cancer, of which about 65% will succumb to the disease [8]. Notwithstanding the considerable amount of progress achieved in the 80's with the advent of platinum-based chemotherapeutic agents (induce cross-linking of subunits of DNA), little positive impact was observed on the mortality rate [9]. The most frequently used chemotherapeutic agents, paclitaxel (mitotic inhibitor) and cisplatin, have shown an average survival rate ranging from 26 to 40 months [10]. However, these agents were also shown to exhibit considerable side effects which are mainly due to their inherent general toxicity [11].

Leukemia

Leukemia remains the most frequently encountered type of cancer in Canadian children ranging in age from 0 to 14 years, with a mortality rate of 36% [12]. Even though its impact is less on the population at large, it remains one of the cancers having the highest mortality rate. Depending on which kind of blood cell is affected, leukemia can be divided into lymphoblastic or lymphocytic leukemias and myeloid or myelogenous leukemias [13]. Notwithstanding the efficacy of some of the classical anticancer agents, most display a cytotoxicity that extends to normal healthy cells, in addition to being subject to the development of some form of chemoresistance following prolonged periods of exposure [14-16].

British Patent 1,398,050 issued to Tuba Z. et al. on Jun. 18, 1975 discloses 2β,16β-bis-piperazino-androstane derivatives and salts thereof having the general formulas I and II respectively:

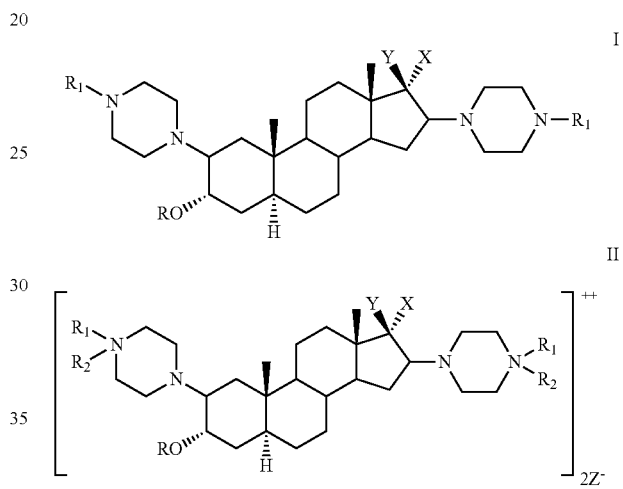

wherein R represents hydrogen or a $C_{1-7}$ acyl group; $R_1$ represents a $C_{1-6}$ alkyl group, acetoxyethyl group, allyl group, or hydroxyethyl group; $R_2$ represents hydrogen, a $C_{1-6}$ alkyl group, allyl group or benzyl group; X stands for hydrogen; Y represents hydroxy or a $C_{1-7}$ acyloxy group; or X and Y together may form an oxo group; and Z represents a chloride, bromide, iodide, hydroxy, mesyloxy or tosyloxy anion. These compounds were disclosed as possessing neuromuscular blocking activity.

The present disclosure refers to a number of documents, the content of which is herein incorporated by reference in their entirety.

SUMMARY

The present disclosure broadly relates to anti-cancer agents. More specifically, but not exclusively, the present disclosure relates to anti-cancer agents exhibiting a strong cytotoxic effect on cancer cells while concomitantly exhibiting low cytotoxicity with respect to normal cells.

In an embodiment, the present disclosure relates to 2-(N-substituted piperazinyl) steroid derivatives. In a further embodiment, the present disclosure relates to 2-(N-substituted piperazinyl) steroid derivatives exhibiting cytotoxicity on a variety of cancer cell lines.

In an embodiment, the present disclosure relates to 2-(N-substituted piperazinyl) pregnane derivatives exhibiting cytotoxicity on a variety of cancer cell lines.

In an embodiment, the present disclosure relates to 2-(N-substituted piperazinyl) androstane derivatives exhibiting cytotoxicity on a variety of cancer cell lines.

In an embodiment, the present disclosure relates to 2-(N-substituted piperazinyl) steroid derivatives of general Formula I:

Formula I wherein:

Y and $Y^1$ are independently selected from the group consisting of $OR_1$, $CHOHR_1$, $OCOR_1$, $OCOCH_2C(CH_2)COOH$; $OCOC(CH_3)_3$; $OCONHC(CH3)_3$, $NHR$, $N(R)_2$, $OSO_2NHR_1$; and $OCOR_2$;

Z is selected from the group consisting of H, alkyl; and $C\equiv CR_1$;

R is selected from the group consisting of H and alkyl;

$R_1$ is selected from the group consisting of H and alkyl;

$R_2$ is $R_3$ is selected from the group consisting of Cl, Br, $NH_2$, $CO_2H$ and $CO_2R$;

Y and Z on the same carbon atom may be a double bonded oxygen (=O);

V is an amino acid;

W is selected from the group consisting of CO, $SO_2$, $CH_2$, CONH and CSNH; and X is selected from the group consisting of alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy, thioalkoxy;

or a pharmaceutically acceptable salt thereof, an N-oxide thereof, or a solvate thereof.

In an embodiment, the present disclosure relates to 2-(N-substituted piperazinyl) steroid derivatives of general Formula I:

Formula I wherein:

Y and $Y^1$ are independently selected from the group consisting of OH, CHOHMe, OMe, OCOMe, $OCOCH_2C(CH_2)COOH$; $OCOC(CH_3)_3$; $OSO_2NH_2$; and $OCOR_2$;

Z is selected from the group consisting of H, $CH_3$; and $C\equiv CH$;

R is H;

$R_2$ is $R_3$ is $CO_2H$ and $CO_2Me$;

V is proline, phenylalanine or tetrahydroisoquinolone;

W is selected from the group consisting of CO, $SO_2$, $CH_2$, CONH and CSNH; and X is selected from the group consisting of alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy, thioalkoxy;

or a pharmaceutically acceptable salt thereof, an N-oxide thereof, or a solvate thereof.

In an embodiment, the present disclosure relates to 2-(N-substituted piperazinyl) steroid derivatives of general Formula I:

Formula I wherein:

Y and $Y^1$ are OH;

Z is H;

R is H;

V is proline, phenylalanine or tetrahydroisoquinolone; and wherein the variables W and X are linked to form the linkage W—X, wherein W—X is selected from the group consisting of

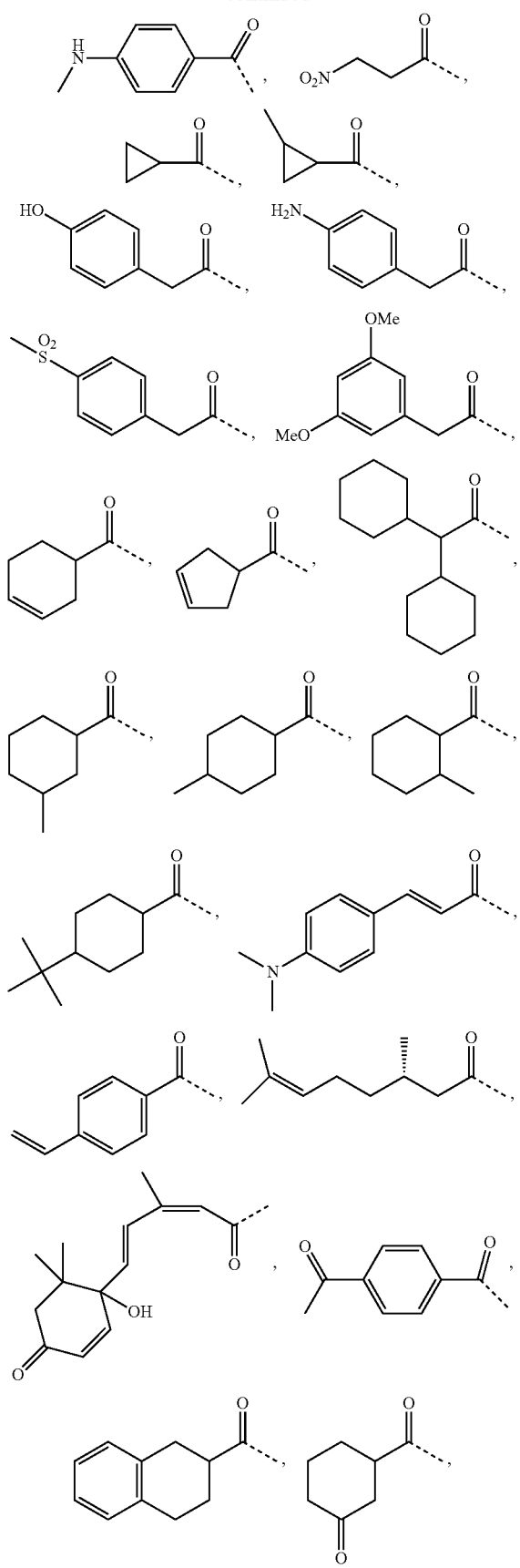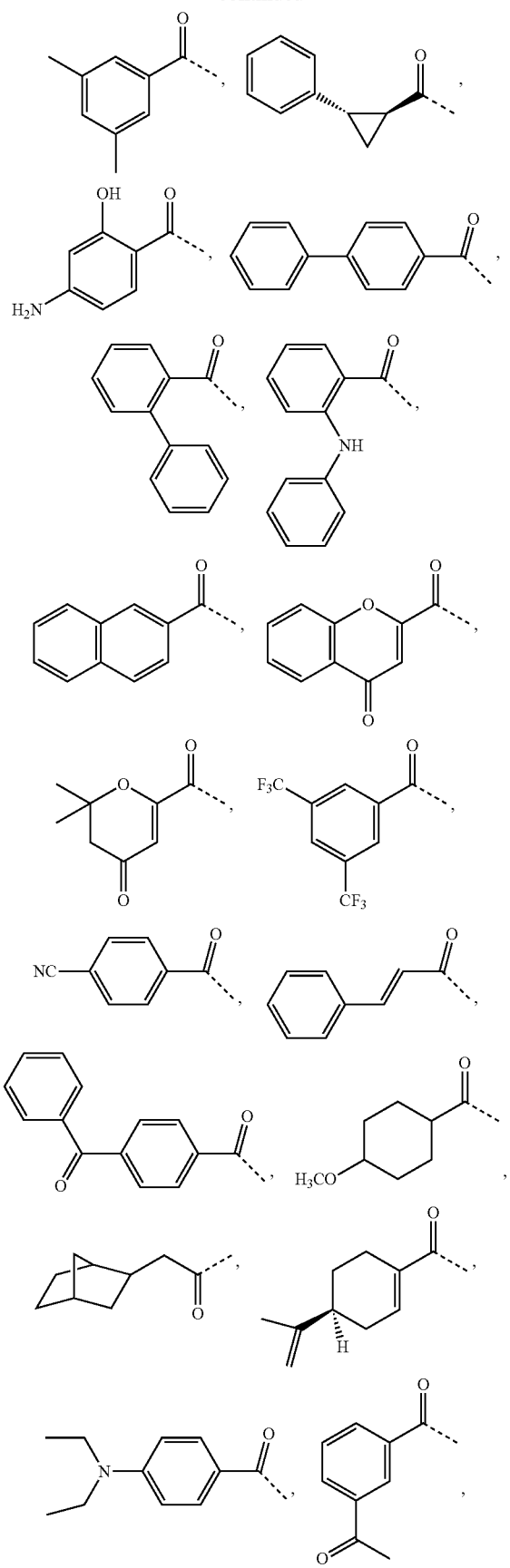

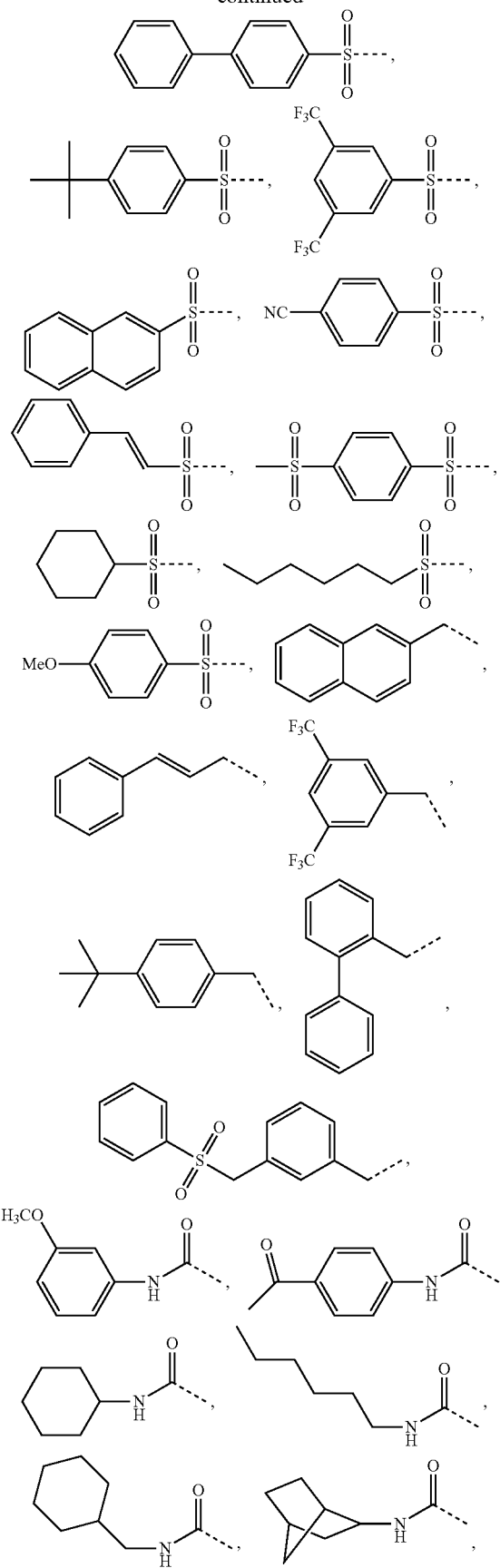

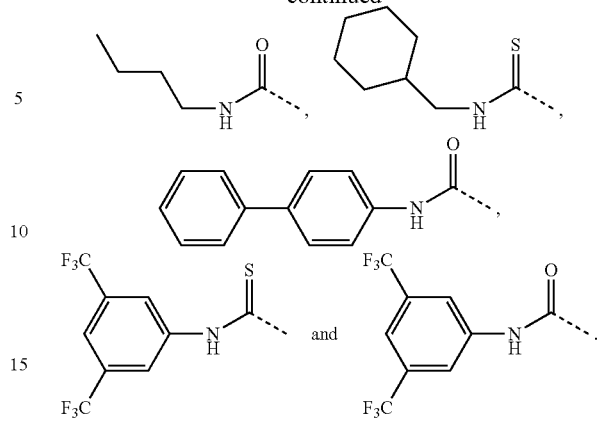

In an embodiment, the present disclosure relates to 2-(N-substituted piperazinyl) steroid derivatives of general Formula I:

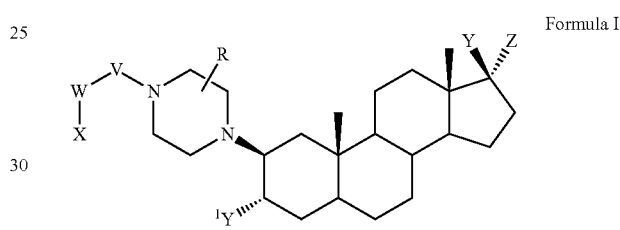

wherein:
Y and $Y^1$ are OH and CHOHMe respectively;
Z is H;
R is H;
V is selected from the group consisting of L-proline, L-phenylalanine D-proline and D-phenylalanine; and
wherein the variables W and X are linked to form the linkage W—X, wherein
W—X is selected from the group consisting of

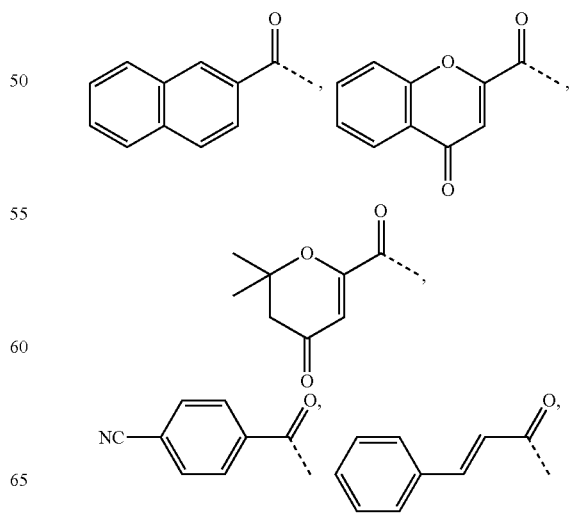

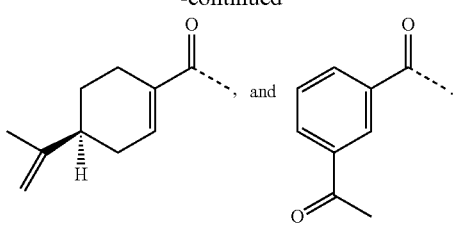, and 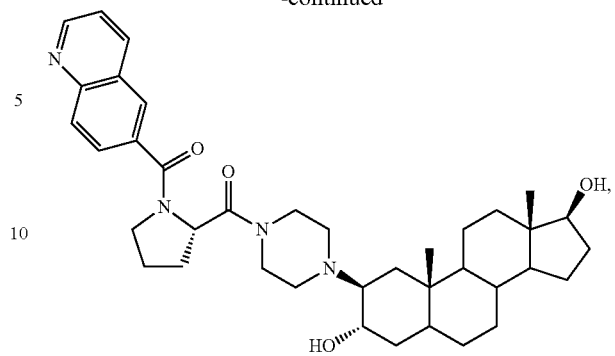
In an embodiment, the present disclosure relates to 2-(N-substituted piperazinyl) steroid derivatives comprising:
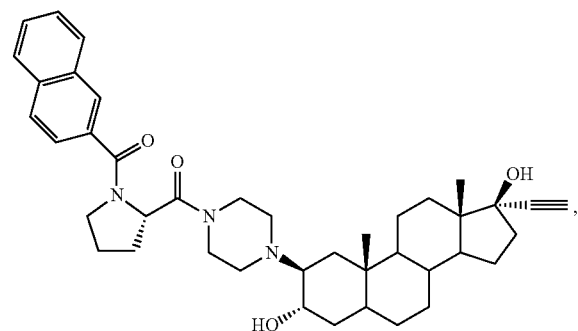
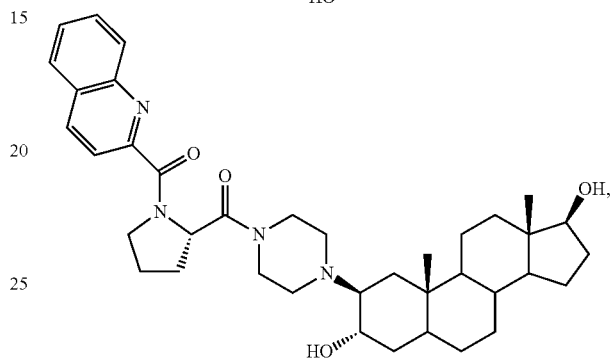
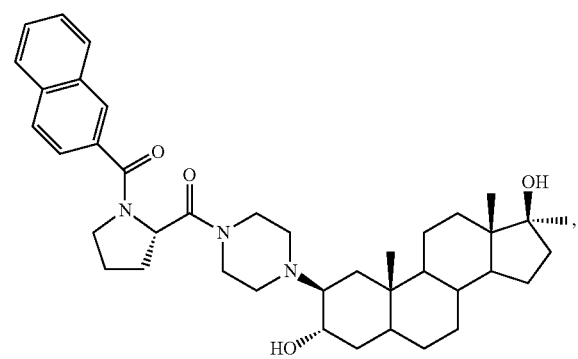
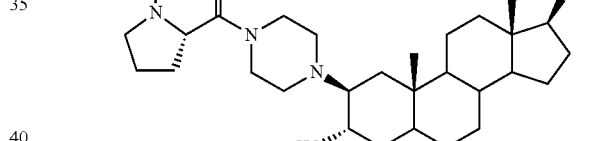
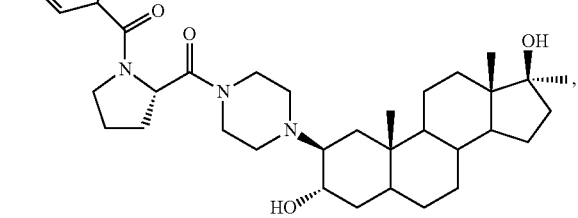
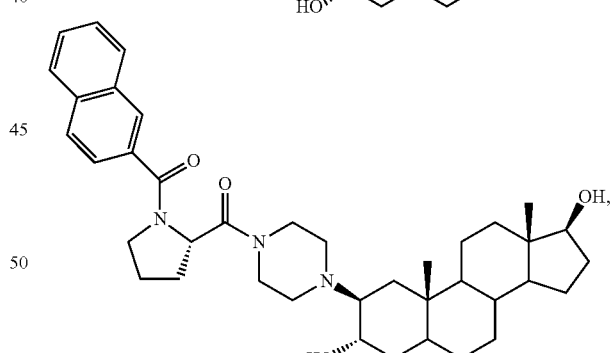
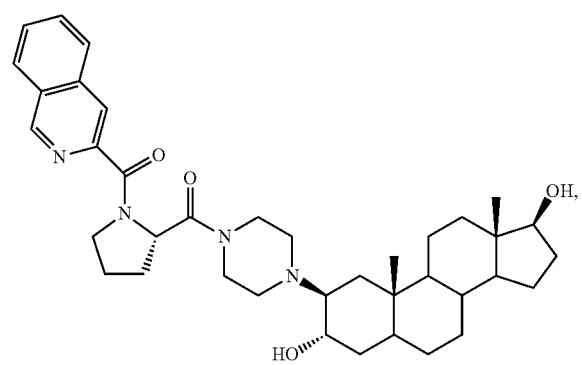
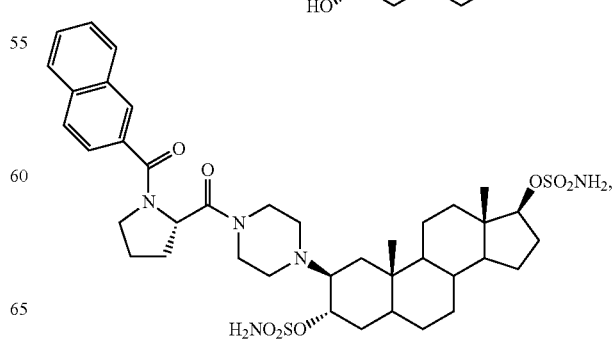

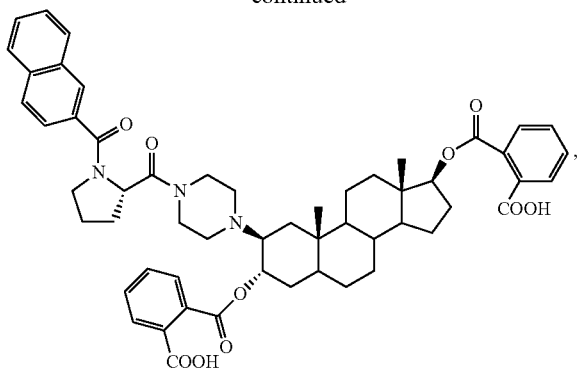

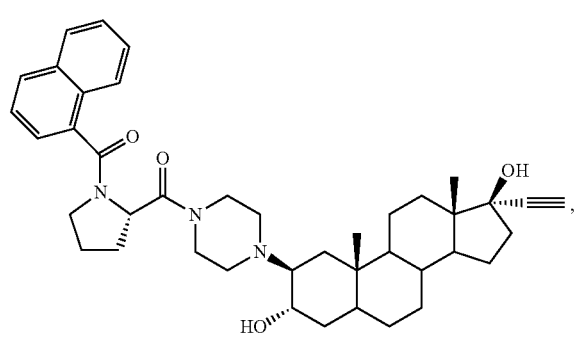

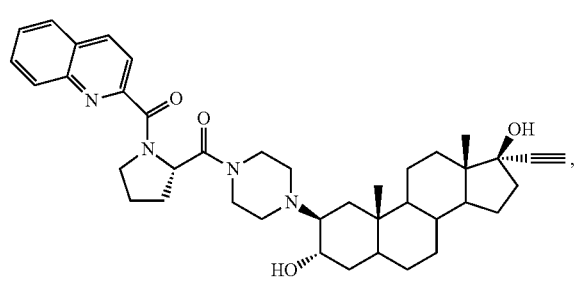

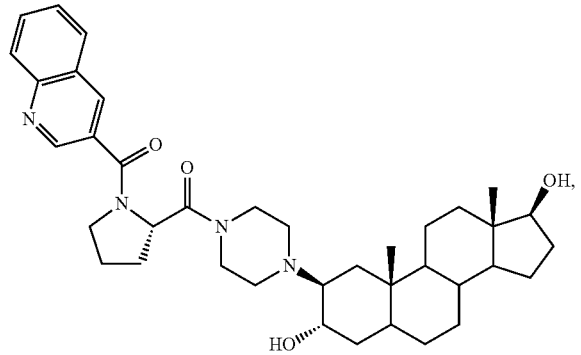

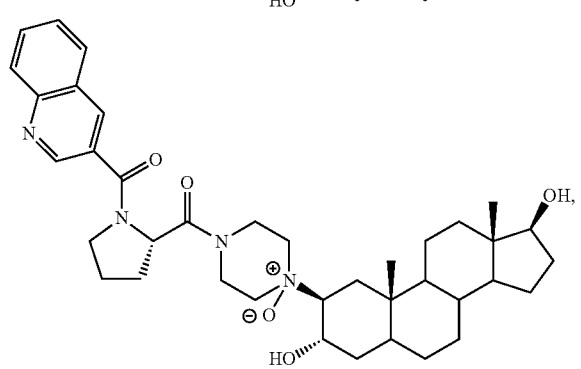

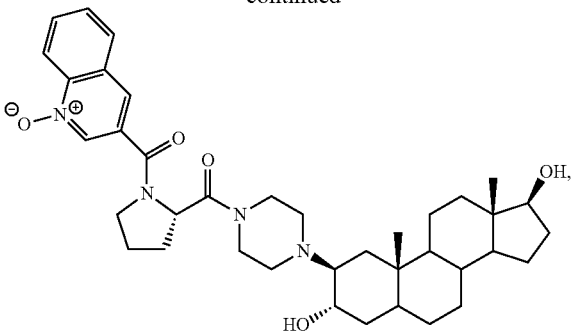

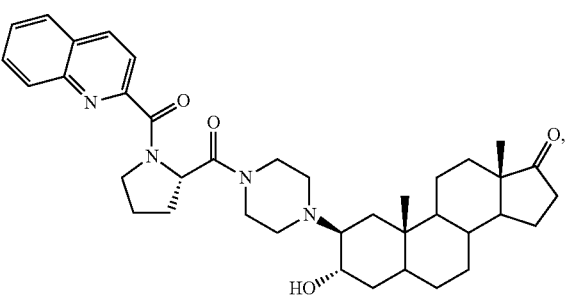

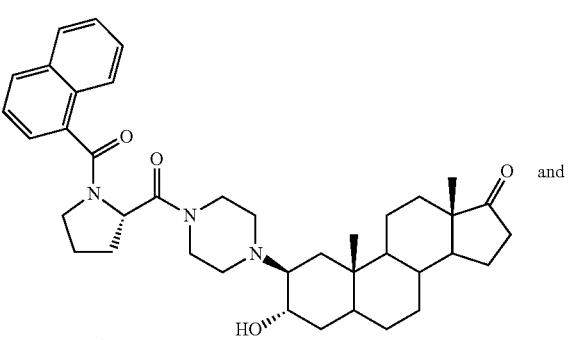

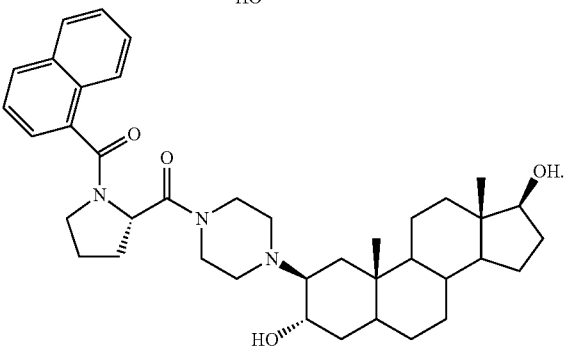

In an embodiment, the present disclosure relates to a method of treating a patient afflicted by cancer, comprising administering to the patient a therapeutically effective amount of one or more of the 2-(N-substituted piperazinyl) steroid derivatives as disclosed herein.

In an embodiment, the present disclosure relates to a method of reducing proliferation of/or inducing cell death of neoplastic cells comprising, contacting the neoplastic cells with one or more of the 2-(N-substituted piperazinyl) steroid derivatives as disclosed herein.

In an embodiment, the present disclosure relates to the use of one or more of the 2-(N-substituted piperazinyl) steroid derivatives as disclosed herein, in the manufacture of a medicament for the treatment of cancer.

In an embodiment, the present disclosure relates to a pharmaceutical composition comprising an effective amount of one or more of the 2-(N-substituted piperazinyl) steroid derivatives as disclosed herein, in association with one or more pharmaceutically acceptable carriers, excipients or diluents.

In an embodiment, the present disclosure relates to an admixture comprising an effective amount of one or more of the 2-(N-substituted piperazinyl) steroid derivatives as disclosed herein, in association with one or more pharmaceutically acceptable carriers, excipients or diluents.

The foregoing and other objects, advantages and features of the present disclosure will become more apparent upon reading of the following non restrictive description of illustrative embodiments thereof, given by way of example only.

BRIEF DESCRIPTION OF THE DRAWINGS

In the appended drawings:

FIG. 1 illustrates the efficacy of PC-37 to reduce the growth of human MCF-7 breast cancer xenografts in ovariectomized (OVX) nude mice. The aminosteroid PC-37 (60 mg/kg in PPG containing 8% of EtOH) was injected subcutaneously 3 times a week. MCF-7 breast cancer cells are sensitive to estrogen estradiol (E2).

DETAILED DESCRIPTION

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups comprise from 2 to 10 carbons.

The term "alkyl" or "alk" as used herein, represents a monovalent group derived from a straight or branched chain saturated hydrocarbon comprising, unless otherwise specified, from 1 to 15 carbon atoms and is exemplified by methyl, ethyl, n- and iso-propyl, n-, sec-, iso- and tert-butyl, neopentyl and the like and may be optionally substituted with one, two, three or, in the case of alkyl groups comprising two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) OC(O)$R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) C(O)$R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) C(O)$NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) S(O)$R^E$, where $R^E$ is selected from the group consisting of (a) alkyl, (b) aryl, (c) arylalkyl, where the alkylene group comprises one to six carbon atoms, and (d) hydroxyl; (29) $S(O)_2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) —$NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The terms "alkoxy" or "alkyloxy," as used interchangeably herein, represent an alkyl group attached to the parent molecular group through an oxygen atom.

The term "alkylsulfinyl" as used herein, represents an alkyl group attached to the parent molecular group through an S(O) group.

The term "alkylsulfonyl," as used herein, represents an alkyl group attached to the parent molecular group through a $S(O)_2$ group.

The term "alkylthio" as used herein, represents an alkyl group attached to the parent molecular group through a sulfur atom.

The term "alkylene" as used herein, represents a saturated divalent hydrocarbon group derived from a straight or branched chain saturated hydrocarbon by the removal of two hydrogen atoms, and is exemplified by methylene, ethylene, isopropylene and the like.

The term "alkenyl," as used herein, represents monovalent straight or branched chain groups of, unless otherwise specified, from 2 to 15 carbons, such as, for example, 2 to 6 carbon atoms or 2 to 4 carbon atoms, containing one or more carbon-carbon double bonds and is exemplified by ethenyl, 1-propenyl, 2-propenyl, 2-methyl-1-propenyl, 1-butenyl, 2-butenyl and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) $OC(O)R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) $C(O)NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) $S(O)R^E$, where $R^E$ is selected from the group consisting of (a) alkyl, (b) aryl, (c) arylalkyl, where the alkylene group comprises one to six carbon atoms, and (d) hydroxyl; (29) $S(O)_2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) —$NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms; (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "alkynyl" as used herein, represents monovalent straight or branched chain groups of from two to six carbon atoms comprising a carbon-carbon triple bond and is exemplified by ethynyl, 1-propynyl, and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) $OC(O)R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) $C(O)NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) $S(O)R^E$, where $R^E$ is selected from the group consisting of (a) alkyl, (b) aryl, (c) arylalkyl, where the alkylene group comprises one to six carbon atoms, and (d) hydroxyl; (29) $S(O)_2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) —$NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "aryl" as used herein, represents mono- and/or bicyclic carbocyclic ring systems and/or multiple rings fused together and is exemplified by phenyl, naphthyl, 1,2-dihydronaphthyl, 1,2,3,4-tetrahydronaphthyl, fluorenyl, indanyl, indenyl and the like and may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups are independently comprised of one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) $(CH_2)_qCO_2R^A$, where q is an integer ranging from zero to four and $R^A$ is selected from the group consisting of (a) alkyl, (b) aryl, and (c) arylalkyl, where the alkylene group comprises one to six carbon atoms; (37) $(CH_2)_qC(O)NR^BR^C$, where $R^B$ and $R^C$ are independently selected from the group consisting of (a) hydrogen, (b) alkyl, (c) aryl, and (d) arylalkyl, where the alkylene group comprises one to six carbon atoms; (38) $(CH_2)_qS(O)_2R^D$, where $R^D$ is selected from the group consisting of (a) alkyl, (b) aryl, and (c) arylalkyl, where the alkylene group comprises one to six carbon atoms; (39) $(CH_2)_qS(O)_2NR^ER^F$, where each of $R^E$ and $R^F$ is independently selected from the group consisting of (a) hydrogen, (b) alkyl, (c) aryl, and (d) arylalkyl, where the alkylene group comprises one to six carbon atoms; (40) $(CH_2)_qNR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, and (i) alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "alkaryl" represents an aryl group attached to the parent molecular group through an alkyl group.

The term "alkheterocyclyl" represents a heterocyclic group attached to the parent molecular group through an alkyl group.

The term "aryloxy" as used herein, represents an aryl group that is attached to the parent molecular group through an oxygen atom.

The term "alkoxyalkyl" as used herein means alkyl-O-alkyl-, wherein alkyl is defined above.

The term "alkoxyaryl" as used herein means alkyl-O-aryl-, wherein alkyl is defined above.

The term "alkthioalkyl" as used herein means alkyl-S-alkyl-, wherein alkyl is defined above.

The term "alkthioaryl" as used herein means alkyl-S-aryl-, wherein alkyl is defined above.

The terms "aryloyl" or "aroyl" as used interchangeably herein, represent an aryl group that is attached to the parent molecular group through a carbonyl group.

The term "carbonyl" as used herein, represents a C(O) group, which can also be represented as C=O.

The terms "carboxy" or "carboxyl," as used interchangeably herein, represents a $CO_2H$ group.

The term "cycloalkyl" as used herein, represents a monovalent saturated or unsaturated non-aromatic cyclic hydrocarbon group of three to eight carbon atoms, unless otherwise specified, and is exemplified by cyclopropyl, cyclobutyl, cyclopentyl, cyclohexyl, cycloheptyl, bicyclo [2.2.1.]heptyl and the like. The cycloalkyl groups of the present disclosure can be optionally substituted with: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups independently comprise from one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; 20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) $(CH_2)_qCO_2R^A$, where q is an integer ranging from zero to four and $R^A$ is selected from the group consisting of (a) alkyl, (b) aryl, and (c) arylalkyl, where the alkylene group comprises one to six carbon atoms; (37) $(CH_2)_qC(O)NR^BR^C$, where each of $R^B$ and $R^C$ is independently selected from the group consisting of (a) hydrogen, (b) alkyl, (c) aryl, and (d) arylalkyl, where the alkylene group comprises one to six carbon atoms; (38) $(CH_2)_qS(O)_2R^D$, where $R^D$ is selected from the group consisting of (a) alkyl, (b) aryl, and (c) arylalkyl, where the alkylene group comprises one to six carbon atoms; (39) $(CH_2)_qS(O)_2NR^ER^F$, where each of $R^E$ and $R^F$ is independently, selected from the group consisting of (a) hydrogen, (b) alkyl, (c) aryl, and (d) arylalkyl, where the alkylene group comprises one to six carbon atoms; (40) $(CH_2)_qNR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms and (i) alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "halogen" or "halo" as used interchangeably herein, represents F, Cl, Br and I.

The term "heteroaryl" as used herein, represents that subset of heterocycles, as defined herein, which is aromatic: (i.e., containing 4n+2 pi electrons within a mono- or multicyclic ring system).

The terms "heterocycle" or "heterocyclyl" as used interchangeably herein represent a 5-, 6- or 7-membered ring, unless otherwise specified, comprising one, two, three, or four heteroatoms independently selected from the group consisting of nitrogen, oxygen, and sulfur. The 5-membered ring has from zero to two double bonds and the 6- and 7-membered rings have from zero to three double bonds. The term "heterocycle" also includes bicyclic, tricyclic, and tetracyclic groups in which any of the above heterocyclic rings is fused to one or two rings independently selected from the group consisting of an aryl ring, a cyclohexane ring, a cyclohexene ring, a cyclopentane ring, a cyclopentene ring and another monocyclic heterocyclic ring such as indolyl, quinolyl, isoquinolyl, tetrahydroquinolyl, benzofuryl, benzothienyl and the like. Heterocycles include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroinidolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

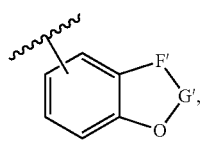

where F' is selected from the group consisting of $CH_2$, $CH_2O$ and O, and G' is selected from the group consisting of C(O) and $(C(R')(R''))_v$, where each of R' and R'' is independently selected from the group consisting of hydrogen and alkyl of one to four carbon atoms, and v is an integer ranging from one to three, and includes groups such as 1,3-benzodioxolyl, 1,4-benzodioxanyl and the like. Any of the heterocyclic groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups independently comprise from one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises from three to eight carbon atoms and the alkylene group comprises from one to ten carbon atoms; (22) halo; (23) haloalkyl of one to six carbon atoms; (24) heterocycle; (25) (heterocycle)oxy; (26) (heterocycle)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises from one to six carbon atoms; (33) oxo; (34) thioalkoxy of one to six carbon atoms; (35) thioalkoxyalkyl, where the alkyl and alkylene groups independently comprise from one to six carbon atoms; (36) $(CH_2)_qCO_2R^A$, where q is an integer ranging from zero to four and $R^A$ is selected from the group consisting of (a) alkyl, (b) aryl, and (c) arylalkyl, where the alkylene group comprises from one to six carbon atoms; (37) $(CH_2)_qC(O)NR^BR^C$, where each of $R^B$ and $R^C$ is independently selected from the group consisting of (a) hydrogen, (b) alkyl, (c) aryl, and (d) arylalkyl, where the alkylene group comprises from one to six carbon atoms; (38) $(CH_2)_qS(O)_2R^D$, where $R^D$ is selected from the group consisting of (a) alkyl, (b) aryl, and (c) arylalkyl, where the alkylene group comprises from one to six carbon atoms; (39) $(CH_2)_qS(O)_2NR^ER^F$, where each of $R^E$ and $R^F$ is independently selected from the group consisting of (a) hydrogen, (b) alkyl, (c) aryl, and (d) arylalkyl, where the alkylene group comprises from one to six carbon atoms; (40) $(CH_2)_qNR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises from one to six carbon atoms; (h) cycloalkyl of three to eight carbon atoms, and (i) alkcycloalkyl, where the cycloalkyl group comprises from three to eight carbon atoms, and the alkylene group comprises from one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The terms "heterocyclyloxy" or "(heterocycle)oxy" as used interchangeably herein, represents a heterocyclic group, as defined herein, attached to the parent molecular group through an oxygen atom.

The term "heterocyclyloyl" or "(heterocycle)oyl" as used interchangeably herein, represents a heterocyclic group, as defined herein, attached to the parent molecular group through a carbonyl group.

The term "amino acid", as used herein, is understood as including both the L and D isomers of the naturally occurring amino acids, as well as other non-proteinaceous amino acids used in peptide chemistry to prepare synthetic analogs of peptides. Examples of naturally-occurring amino acids include, but are not limited to glycine, alanine, valine, leucine, isoleucine, serine, and threonine. Examples of non-proteinaceous amino acids include, but are not limited to norleucine, norvaline, cyclohexyl alanine, biphenyl alanine, homophenyl alanine, naphthyl alanine, pyridyl alanine, and substituted phenyl alanines (substituted with a or more substituents including but not limited to alkoxy, halogen and nitro groups). Beta and gamma amino acids are also within the scope of the term "amino acid". Amino acids protected by standard protecting groups commonly used in peptide synthesis are also within the scope of the term "amino acid". These compounds are known to persons skilled in the art of peptide chemistry.

The term "oxo" as used herein, represents =O.

The term "perfluoroalkyl" as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "heteroatom", as used herein, is understood as being oxygen, sulfur or nitrogen.

The term "sulfonyl" as used herein, represents an $S(O)_2$ group.

The term "thioalkoxy" as used herein, represents an alkyl group attached to the parent molecular group through a sulfur atom. Exemplary unsubstituted thioalkoxy groups comprise from 1 to 6 carbon atoms.

The term "thiocarbonyl" as used herein, represents a C(S) group, which can also be represented as C=S.

The term "patient", as used herein, is understood as being any individual treated with the 2-(N-substituted piperazinyl) steroid derivatives of the present disclosure.

Prodrugs and solvates of the 2-(N-substituted piperazinyl) steroid derivatives of the present disclosure are also contemplated herein. The term "prodrug", as used herein, is understood as being a compound which, upon administration to a subject, undergoes chemical conversion by metabolic or chemical processes to yield a compound of the Formula I, or a salt and/or solvate thereof. Solvates of the compounds of Formula I are preferably hydrates.

The term "derivative" as used herein, is understood as being a substance which comprises the same basic carbon skeleton and carbon functionality in its structure as a given compound, but can also bear one or more substituents or rings.

The term "analogue" as used herein, is understood as being a substance similar in structure to another compound but differing in some slight structural detail.

The term "salt(s)" as used herein, is understood as being acidic and/or basic salts formed with inorganic and/or organic acids or bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps.

The variable "U" (Tables 1 and 2) as used herein is understood as referring to the linkage composed of variables W and X. The linkage W—X is further illustrated in Formula I.

Examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, phosphoric, 2-hydroxyethanesulfonate, lactate, maleate, mandelate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

Examples of base addition salts include but are not limited to alkali metal salts and alkaline earth metal salts. Non limiting examples of alkali metal salts include lithium, sodium and potassium salts. Non-limiting examples of alkaline earth metal salts include magnesium and calcium salts.

It is contemplated that any embodiment discussed in this disclosure can be implemented with respect to any method or composition of the disclosure, and vice versa. Furthermore, compositions of the disclosure can be used to achieve the methods of the disclosure.

In an embodiment, the present disclosure relates to 2-(N-substituted piperazinyl) steroid derivatives of general Formula I:

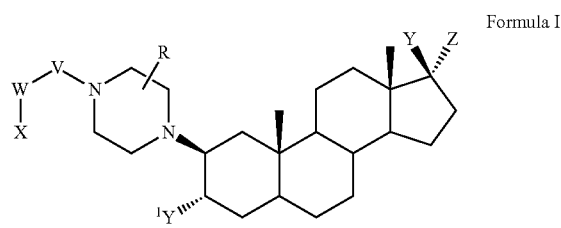

Formula I wherein:

Y and $Y^1$ are independently selected from the group consisting of $OR_1$, $CHOHR_1$, $OCOR_1$, $OCOCH_2C(CH_2)COOH$; $OCOC(CH_3)_3$; $OCONHC(CH3)_3$, $NHR$, $N(R)_2$, $OSO_2NHR_1$; and $OCOR_2$;

Z is selected from the group consisting of H, alkyl; and C≡$CR_1$;

R is selected from the group consisting of H and alkyl;

$R_1$ is selected from the group consisting of H and alkyl;

$R_2$ is

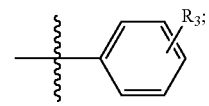

$R_3$ is selected from the group consisting of Cl, Br, $NH_2$, $CO_2H$ and $CO_2R$;

Y and Z on the same carbon atom may be a double bonded oxygen (=O);

V is an amino acid;

W is selected from the group consisting of CO, $SO_2$, $CH_2$, CONH and CSNH; and X is selected from the group consisting of alkyl, alkylsulfinyl, alkylthio, alkylsulfonyl, alkoxy, alkenyl, alkynyl, aryl, alkaryl, alkheterocyclyl, aryloxy, alkoxyalkyl, alkoxyaryl, alkthioalkyl, alkthioaryl, cycloalkyl, heteroaryl, heterocyclyl, heterocyclyloxy, thioalkoxy;

or a pharmaceutically acceptable salt thereof, an N-oxide thereof, or a solvate thereof.

In yet a further embodiment, the present disclosure relates to pharmaceutical compositions comprising a therapeutically effective amount of one or more of the 2-(N-substituted piperazinyl) steroid derivatives or pharmaceutically acceptable salts or N-oxides thereof as disclosed herein, and at least one pharmaceutically acceptable excipient, non-limiting examples of which are carriers and diluents. The term "therapeutically effective amount" is understood as being an amount of 2-(N-substituted piperazinyl) steroid derivative or a pharmaceutically acceptable salt or N-oxide thereof as disclosed herein, required upon administration to a patient in order to treat a condition characterized by the uncontrolled proliferation of genetically altered tissue cells. Therapeutic methods comprise the step of treating patients in a pharmaceutically acceptable manner with the 2-(N-substituted piperazinyl) steroid derivatives or pharmaceutically acceptable salts or N-oxides thereof as disclosed herein, or with compositions comprising such 2-(N-substituted piperazinyl) steroid derivatives or pharmaceutically acceptable salts or N-oxides thereof Such compositions may be in the form of tablets, coated tablets, capsules, caplets, powders, granules, lozenges, suppositories, reconstitutable powders, syrups, liquid preparations such as oral or sterile parenteral solutions or suspensions, as well as injectable formulations and transdermal formulations.

The 2-(N-substituted piperazinyl) steroid derivatives or pharmaceutically acceptable salts or N-oxides thereof of the present disclosure may be administered alone or in combination with pharmaceutically acceptable carriers. The proportion of each carrier is determined by the solubility and chemical nature of the compound, the route of administration, and standard pharmaceutical practice. In order to ensure consistency of administration, in an embodiment of the present disclosure, the pharmaceutical composition is in the form of a unit dose. The unit dose presentation forms for oral administration may be tablets, coated tablets and capsules and may contain conventional excipients. Non-limiting examples of conventional excipients include binding agents such as acacia, gelatin, sorbitol, or polyvinylpyrrolidone; fillers such as lactose, dextrose, saccharose, sugar, maize-starch, calcium phosphate, sorbitol or glycine; tabletting lubricants such as talc, stearic acid, calcium or magnesium stearate, polyethylene glycols, gums, gels; disintegrants such as starch, polyvinylpyrrolidone, sodium starch glycollate or microcrystalline cellulose; or pharmaceutically acceptable wetting agents such as sodium lauryl sulphate.

The 2-(N-substituted piperazinyl) steroid derivatives or pharmaceutically acceptable salts or N-oxides thereof of the present disclosure may be injected parenterally; this being intramuscularly, intravenously, or subcutaneously. For parenteral administration, the 2-(N-substituted piperazinyl) steroid derivatives or pharmaceutically acceptable salts or N-oxides thereof may be used in the form of sterile solutions containing solutes for example, sufficient saline or glucose to make the solution isotonic.

The 2-(N-substituted piperazinyl) steroid derivatives or pharmaceutically acceptable salts or N-oxides thereof of the present disclosure may also be administered via transdermal routes using dermal or skin patches.

The 2-(N-substituted piperazinyl) steroid derivatives or pharmaceutically acceptable salts or N-oxides thereof may be administered orally in the form of tablets, coated tablets, capsules, or granules, containing suitable excipients non-limiting examples of which are starch, lactose, white sugar and the like. The 2-(N-substituted piperazinyl) steroid derivatives or pharmaceutically acceptable salts or N-oxides thereof may be administered orally in the form of solutions which may contain coloring and/or flavoring agents. The 2-(N-substituted piperazinyl) steroid derivatives or pharmaceutically acceptable salts or N-oxides thereof may also be administered sublingually in the form of tracheas or lozenges in which the active ingredient(s) is/are mixed with sugar or corn syrups, flavoring agents and dyes, and then dehydrated sufficiently to make the mixture suitable for pressing into solid form.

The solid oral compositions may be prepared by conventional methods of blending, granulation, compression, coating, filling, tabletting, or the like. Repeated blending operations may be used to distribute the active agent throughout those compositions employing large quantities of fillers. Such operations are, of course, conventional in the art. The tablets may be coated according to methods well known in normal pharmaceutical practice, in particular with an enteric coating.

Oral liquid preparations may be in the form of emulsions, suspensions, syrups, or elixirs, or may be presented as a dry product for reconstitution with water or other suitable vehicle before use. Such liquid preparations may or may not contain conventional additives. Non limiting examples of conventional additives include suspending agents such as sorbitol, syrup, natural gums, agar, methyl cellulose, gelatin, pectin, sodium alginate, hydroxyethylcellulose, carboxymethylcellulose, aluminum stearate gel, or hydrogenated edible fats; emulsifying agents such as sorbitan monooleate or acaci; non-aqueous vehicles (which may include edible oils) such as almond oil, fractionated coconut oil, oily esters selected from the group consisting of glycerine, propylene glycol, ethylene glycol, and ethyl alcohol; preservatives such as for instance methyl para-hydroxybenzoate, ethyl para-hydroxybenzoate, n-propyl parahydroxybenzoate, n-butyl parahydroxybenzoate or sorbic acid; and, if desired conventional flavoring such as saccharose, glycerol, mannitol, sorbitol, or coloring agents.

For parenteral administration, fluid unit dosage forms may be prepared by utilizing the 2-(N-substituted piperazinyl) steroid derivatives or pharmaceutically acceptable salts or N-oxides thereof and a sterile vehicle (i.e. sterile water) and, depending on the concentration employed, the 2-(N-substituted piperazinyl) steroid derivatives or pharmaceutically acceptable salts or N-oxides thereof may be either suspended or dissolved in the vehicle. Other suitable vehicles may include olive oil, ethyl oleate, and glycols. If needed, a suitable quantity of lidocaine hydrochloride may also be included. Once in solution, the 2-(N-substituted piperazinyl) steroid derivatives or pharmaceutically acceptable salts or N-oxides thereof may be injected and filter sterilized before filling a suitable vial or ampoule followed by subsequently sealing the carrier or storage package. Adjuvants, such as a local anesthetic, a preservative or a buffering agent, may be dissolved in the vehicle prior to use. Stability of the pharmaceutical composition may be enhanced by freezing the composition after filling the vial and removing the water under vacuum, (e.g., freeze drying). Parenteral suspensions may be prepared in substantially the same manner, except that the 2-(N-substituted piperazinyl) steroid derivatives or pharmaceutically acceptable salts or N-oxides thereof should be suspended in the vehicle rather than being dissolved, and, further, sterilization is not achievable by filtration. The 2-(N-substituted piperazinyl) steroid derivatives or pharmaceutically acceptable salts or N-oxides thereof may be sterilized, however, by exposing it to ethylene oxide before suspending it in the sterile vehicle. A surfactant or wetting solution may be advantageously included in the composition to facilitate uniform distribution of the 2-(N-substituted piperazinyl) steroid derivatives or pharmaceutically acceptable salts or N-oxides thereof.

The 2-(N-substituted piperazinyl) steroid derivatives or pharmaceutically acceptable salts or N-oxides thereof may be administered in the form of suppositories. Suppositories may contain pharmaceutically acceptable vehicles such as cocoa butter, polyethylene glycol, sorbitan, esters of fatty acids, lecithin and the like.

The pharmaceutical compositions of the present disclosure comprise a pharmaceutically effective amount of at least one 2-(N-substituted piperazinyl) steroid derivative or pharmaceutically acceptable salt or N-oxide thereof as disclosed herein and one or more pharmaceutically acceptable carriers, excipients or diluents. In an embodiment of the present disclosure, the pharmaceutical compositions contain from about 0.1% to about 99% by weight of a 2-(N-substituted piperazinyl) steroid derivative or pharmaceutically acceptable salt or N-oxide thereof as disclosed herein. In a further embodiment of the present disclosure, the pharmaceutical compositions contain from about 10% to about 60% by weight of a 2-(N-substituted piperazinyl) steroid derivative or pharmaceutically acceptable salt or N-oxide thereof as disclosed herein, depending on which method of administration is employed. Physicians will determine the most-suitable dosage of the present therapeutic agents (the 2-(N-substituted piperazinyl) steroid derivatives or pharmaceutically acceptable salts or N-oxides thereof). Dosages may vary with the mode of administration and the particular 2-(N-substituted piperazinyl) steroid derivative chosen. In addition, the dosage may vary with the particular patient under treatment. The dosage of the 2-(N-substituted piperazinyl) steroid derivative or pharmaceutically acceptable salt or N-oxide thereof used in the treatment may vary, depending on the relative efficacy of the compound and the judgment of the treating physician.

In a non-limiting embodiment, the 2-(N-substituted piperazinyl) steroid derivatives of the present disclosure are suitable for oral administration.

In an embodiment of the present disclosure the pharmaceutical compositions comprise a therapeutically effective amount of one or more of the 2-(N-substituted piperazinyl) steroid derivatives or pharmaceutically acceptable salts or N-oxides thereof as disclosed herein, and at least one pharmaceutically acceptable excipient, non-limiting examples of which are carriers and diluents.

The present disclosure refers to a number of chemical terms and abbreviations used by those skilled in the art. Nevertheless, definitions of selected terms are provided for clarity and consistency.

Abbreviations: NMR: Nuclear Magnetic Resonance; s, singlet; d, doublet; dd, doublet of doublet; t, triplet; q, quadruplet; and m, multiplet; LRMS: Low Resolution Mass Spectrometry; TLC: Thin Layer Chromatography; FCC: Flash Column Chromatography; EtOAc: Ethyl Acetate; $CH_2Cl_2$: Dichloromethane; $CDCl_3$: Chloroform-d; MeOH: Methanol; DMF: Dimethylformamide; THF: Tetrahydrofuran; TFA: Trifluoroacetic acid; DAST: Diethylaminosulfur trifluoride; DIBAL-H: Diisobutylaluminium Hydride; Fmoc-O-Suc: N-(9-Fluorenylmethoxycarbonyloxy) Succinimide; m-CPBA: 3-Chloroperbenzoic acid; PS-DES-Cl: Polystyrene Butyldiethylsilyl Chloride; Fmoc: 9-Fluorenylmethyloxycarbonyl; TEA: Triethylamine; PyBOP: Benzotriazole-yl-oxy-tris-pyrrolidinophosphonium hexafluorophosphate; HOBt: 1-Hydroxybenzotriazole; DIPEA: Diisopropylethylamine; AcCl: Acetyl chloride; $NaBH_4$: Sodium borohydride.

In an embodiment, the present disclosure relates to anti-cancer agents exhibiting strong cytotoxicity on cancer cells while concomitantly exhibiting low cytotoxicity with respect to normal cells. The improved therapeutic index observed with the agents of the present disclosure allows reducing the adverse side-effects typically associated with the administration of many of the currently used anti-tumor agents [17].

In an embodiment, the present disclosure relates to 2-(N-substituted piperazinyl) steroid derivatives exhibiting cytotoxicity on a variety of cancer cell lines. These derivatives were shown to exhibit substantially no adverse effect on normal healthy cells (Table 3).

In an embodiment, the present disclosure relates to 2-(N-substituted piperazinyl) steroid derivatives for use as therapeutic agents for the treatment of breast cancer and prostate cancer. The anti-cancer agents of the present disclosure were shown to display a strong cytotoxic effect on breast cancer cells (MCF-7 and Shionogi) and prostate cancer cells (LN-CaP and Shionogi). In an embodiment, the 2-(N-substituted piperazinyl) steroid derivatives of the present disclosure are suitable for use in cases where hormone independence is observed.

In an embodiment, the present disclosure relates to 2-(N-substituted piperazinyl) steroid derivatives for use as therapeutic agents for the treatment of ovarian cancer. The anti-cancer agents of the present disclosure were shown to display a cytotoxic effect on ovarian cancer cells (OVCAR-3; $IC_{50}$=0.7-1.5 µM) similar to the effect observed with the cytotoxic agent Doxorubicin ($IC_{50}$=0.9 µM). In an embodiment, the 2-(N-substituted piperazinyl) steroid derivatives of the present disclosure are suitable for use in cases where non-selective cytotoxic agents such as Doxorubicin constitute the main course of action in combating ovarian cancer.

In an embodiment, the present disclosure relates to 2-(N-substituted piperazinyl) steroid derivatives for use as therapeutic agents for the treatment of leukemia. The anti-cancer agents of the present disclosure were shown to display a strong cytotoxic effect on the promyeloid cancer cell line HL-60 ($IC_{50}$=1.2-30 µM) and the lymphoid cancer cell line K562 ($IC_{50}$>8 µM). Interestingly, some of the anti-cancer agents of the present disclosure (e.g. PC-37 and FC-48) display little or no toxicity on normal healthy lymphocytes, even at high concentrations (>10 µM).

Without being bound to any theory, it is believed that the mechanism of action of the 2-(N-substituted piperazinyl) steroid derivatives of the present disclosure is different from the mode of action of the classical chemotherapy agents (antimetabolites, alkylating agents, and intercalants) [18]. This is an important observation when considering alternative therapies for combating refractory cancers such as the breast cancer cell line MCF-7, known for its resistance to Doxorubicin (Table 3), as well as other refractory cancers having developed some form of chemoresistance.

In accordance with an embodiment of the present disclosure, the preparation of 2β-N-Fmoc-piperazino-5α-androstane-3α,17β-diol (6) is illustrated hereinbelow in Scheme 1.

Scheme 1:

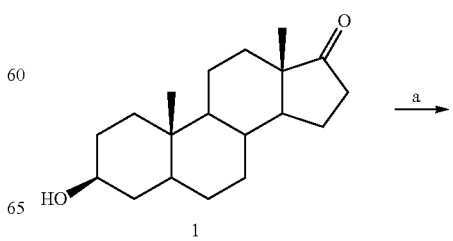

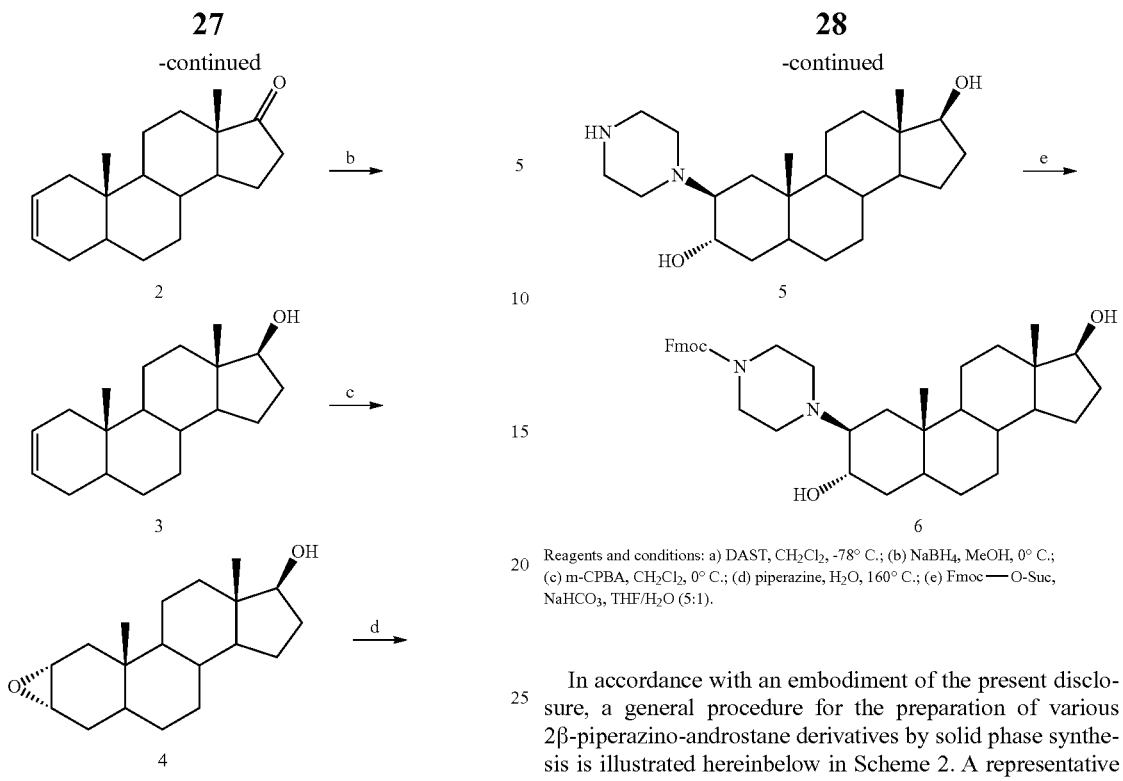

Reagents and conditions: a) DAST, CH$_2$Cl$_2$, -78° C.; (b) NaBH$_4$, MeOH, 0° C.; (c) m-CPBA, CH$_2$Cl$_2$, 0° C.; (d) piperazine, H$_2$O, 160° C.; (e) Fmoc—O-Suc, NaHCO$_3$, THF/H$_2$O (5:1).

In accordance with an embodiment of the present disclosure, a general procedure for the preparation of various 2β-piperazino-androstane derivatives by solid phase synthesis is illustrated hereinbelow in Scheme 2. A representative number of derivatives are illustrated in Table 1.

Scheme 2:
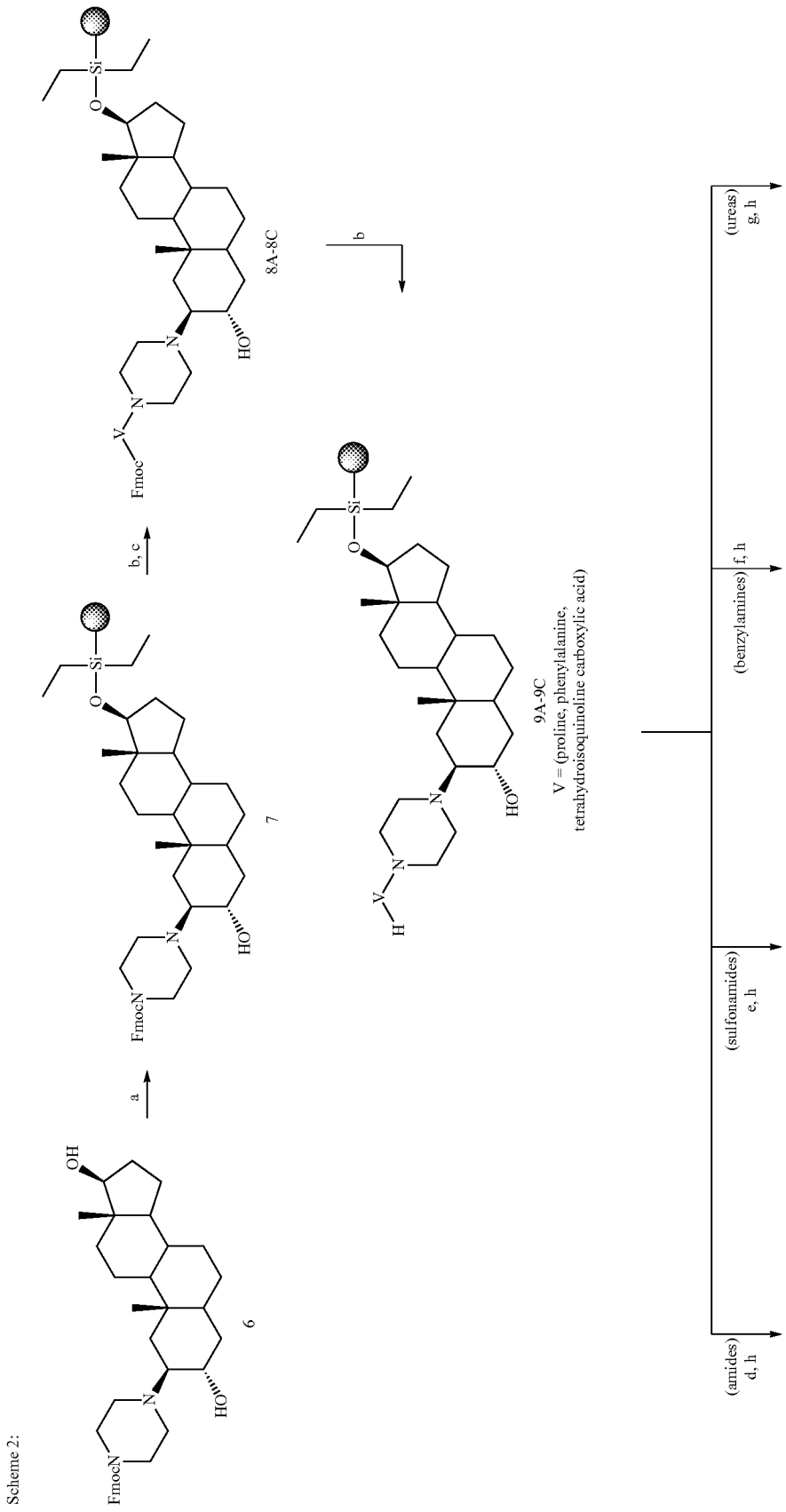

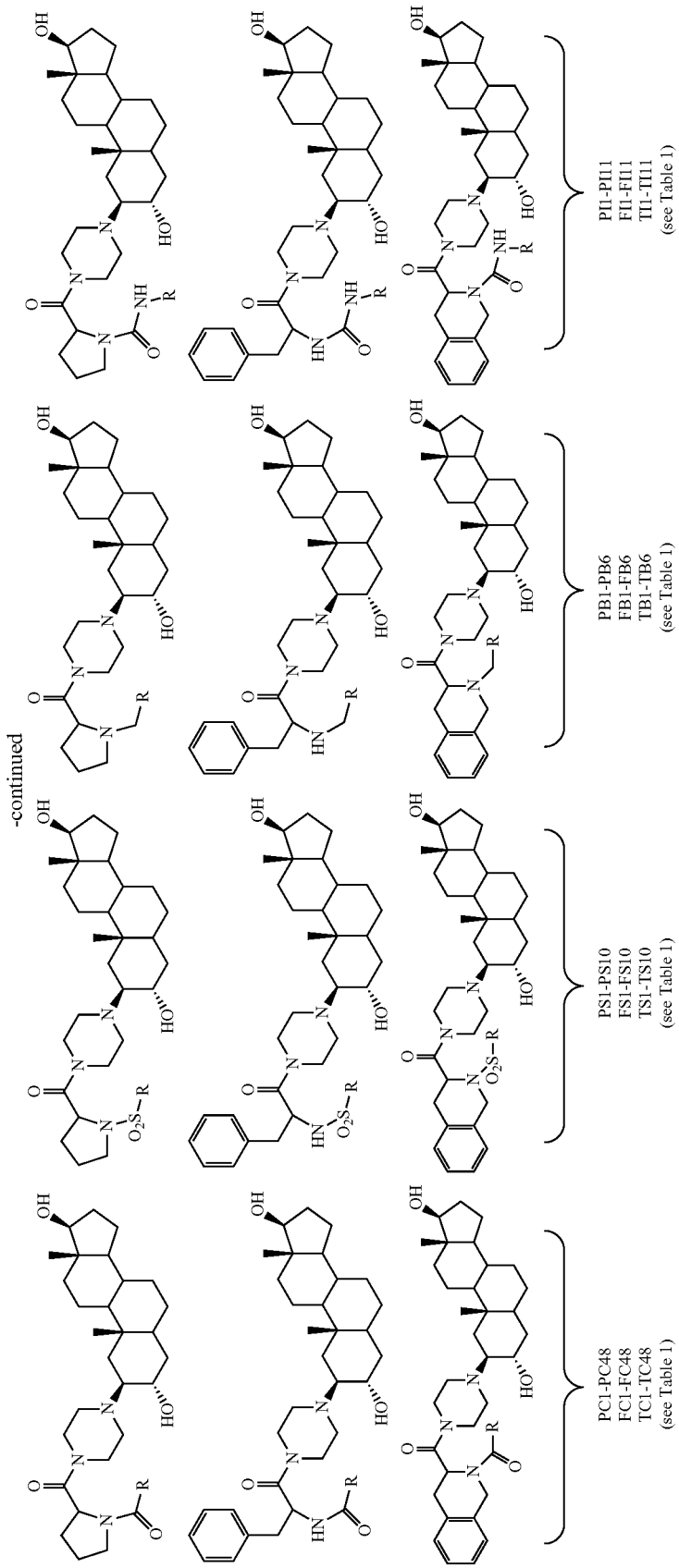

-continued

PI1-PII1
FI1-FII1
TI1-TII1
(see Table 1)

PB1-PB6
FB1-FB6
TB1-TB6
(see Table 1)

PS1-PS10
FS1-FS10
TS1-TS10
(see Table 1)

PC1-PC48
FC1-FC48
TC1-TC48
(see Table 1)

Reagents and conditions: (a) i) PS-DES-Cl resin, imidazole, $CH_2Cl_2$, rt; (b) 20% piperidine in $CH_2Cl_2$ (v/v), rt; (c) N-Fmoc-amino acid (Fmoc-PRO-OH, Fmoc-PHE-OH or Fmoc-TIC-OH), PyBOP, HOBt, DIPEA, DMF, rt; (d) Carboxylic acid (RCOOH), PyBOP, HOBt, DIPEA, DMF, rt; (e) Sulfonyl chloride ($RSO_2Cl$), TEA, $CH_2Cl_2$, rt; (f) Arylbromide ($ArCH_2Br$), TEA, $CH_2Cl_2$, rt; (g) Isocyanate (RCNO), TEA, $CH_2Cl_2$, rt; (h) i) HCl (2M)/MeOH (AcCl + MeOH) in $CH_2Cl_2$ (20:80, v/v); ii. 10% $NaHCO_3$.

TABLE 1
Structures of 2β-piperazino-androstane derivatives.
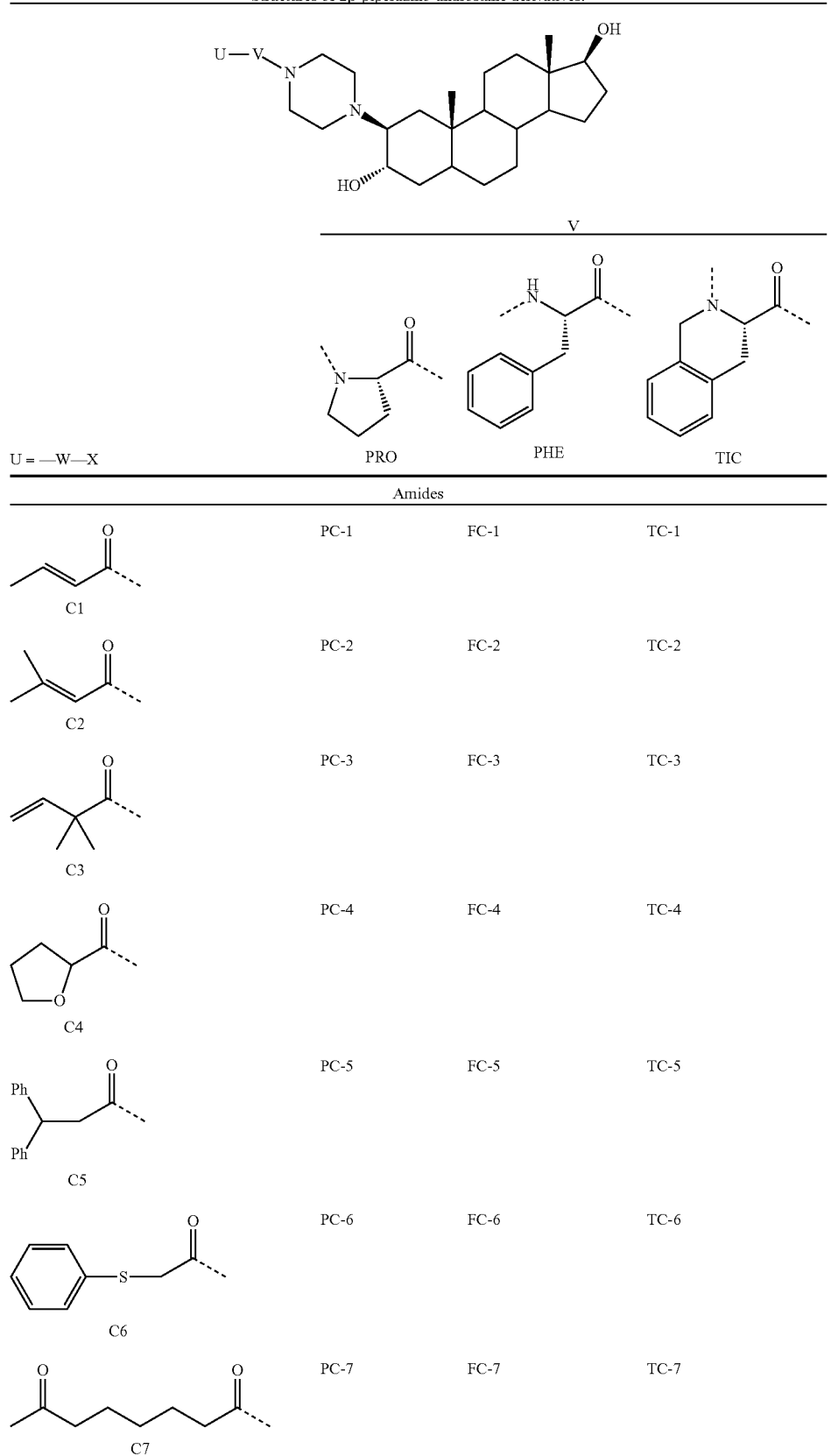

TABLE 1-continued
Structures of 2β-piperazino-androstane derivatives.
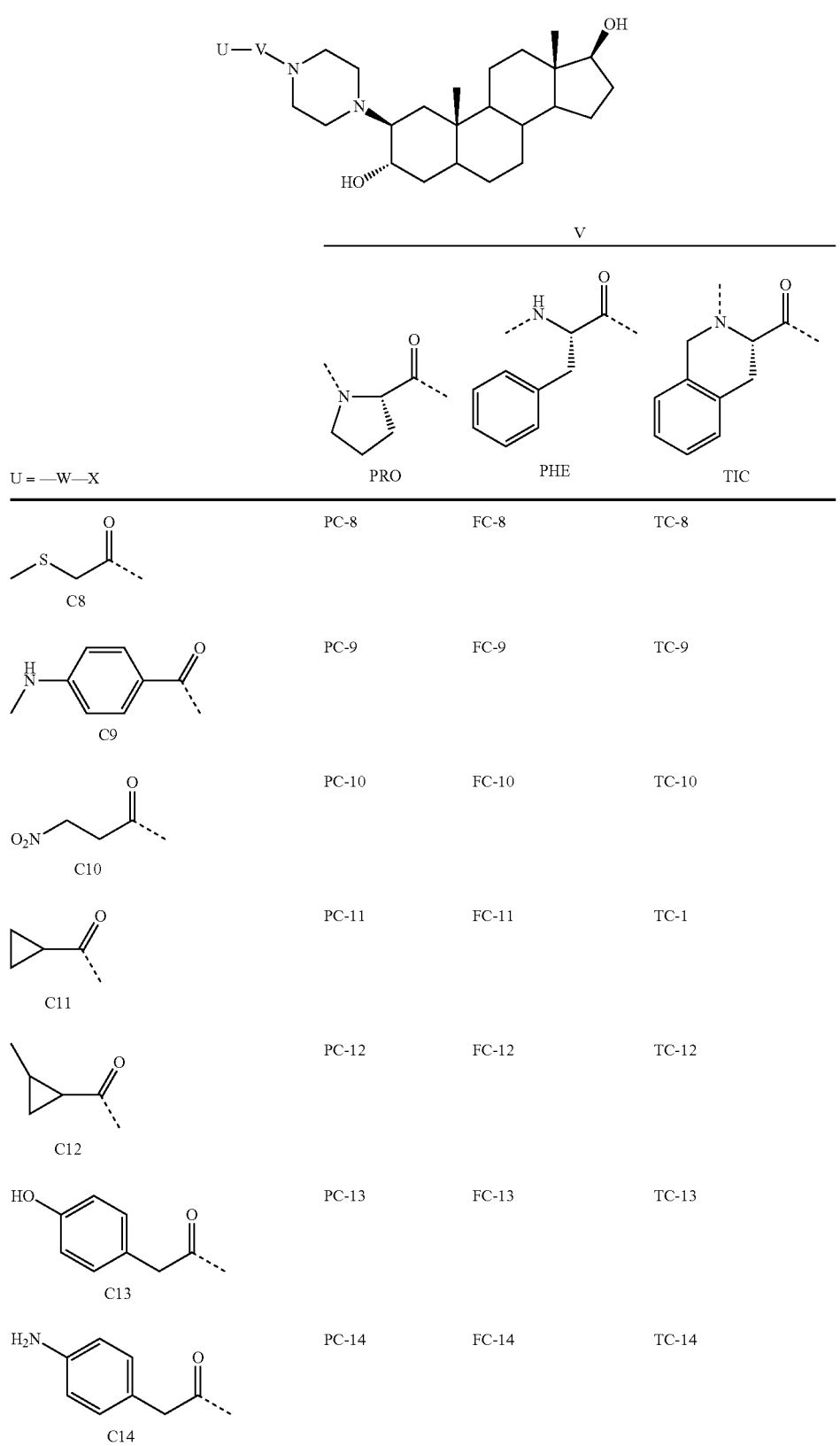

TABLE 1-continued
Structures of 2β-piperazino-androstane derivatives.
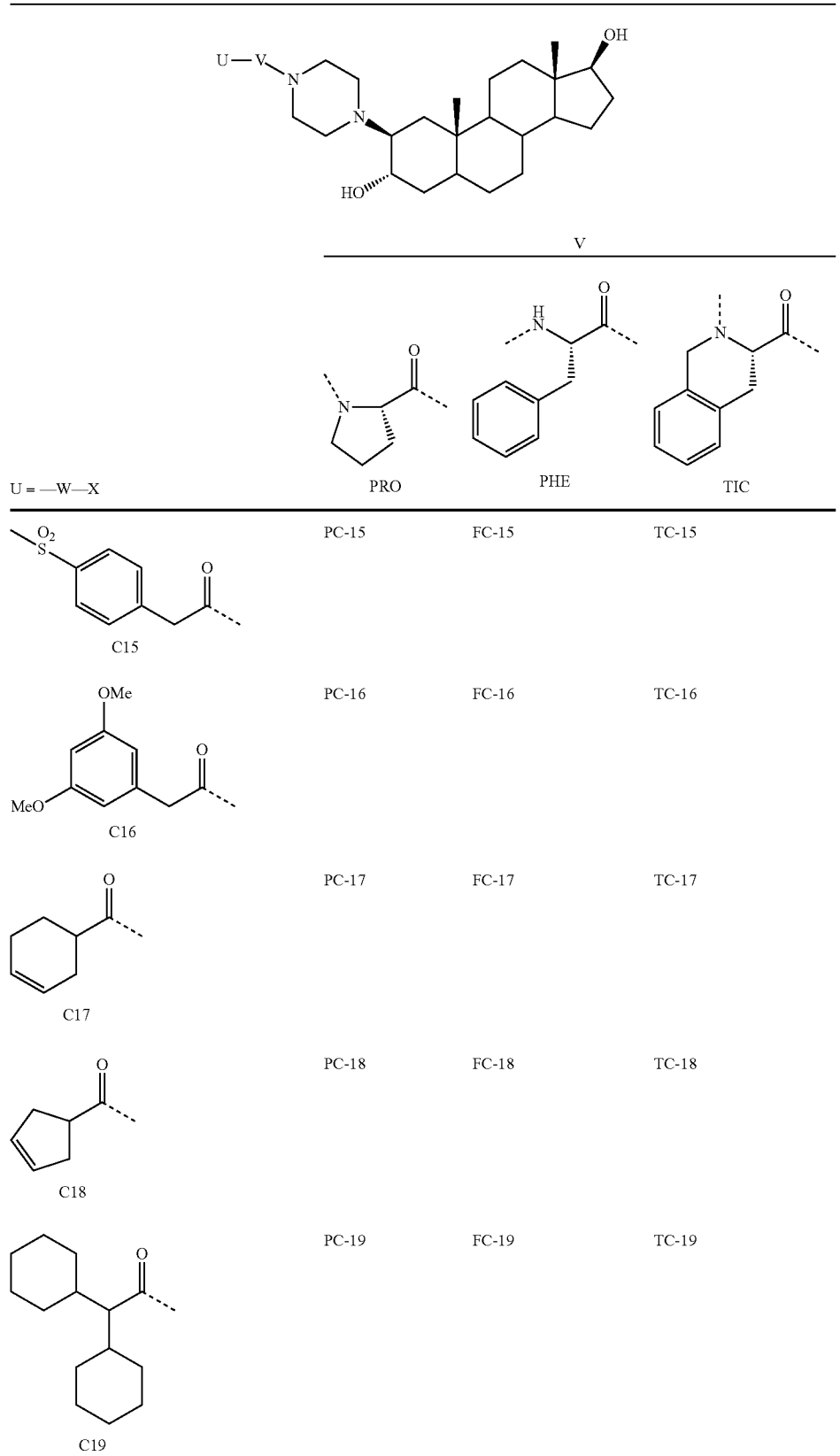

TABLE 1-continued
Structures of 2β-piperazino-androstane derivatives.
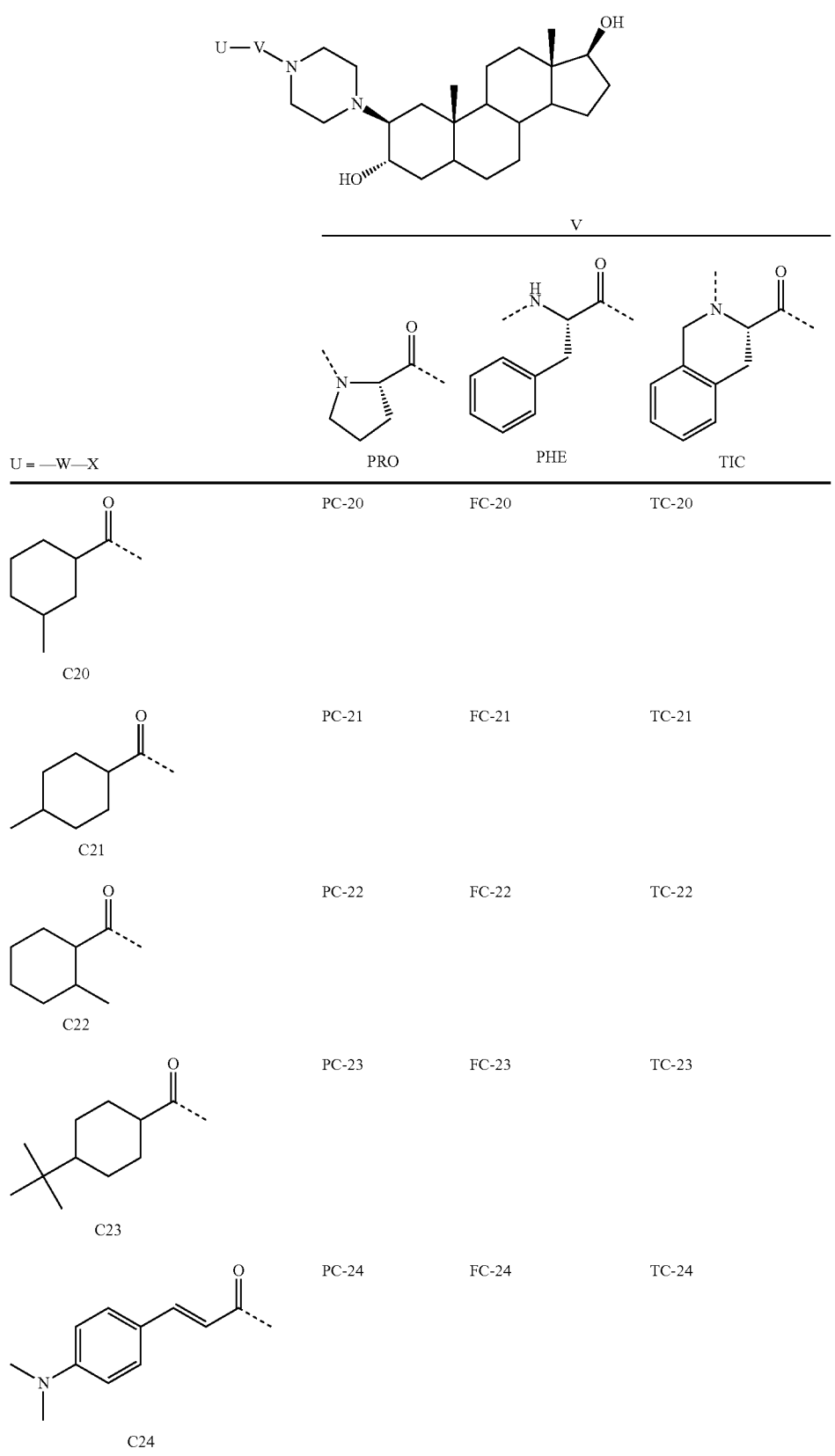
| U = —W—X | PRO | PHE | TIC |
|---|---|---|---|
| C20 | PC-20 | FC-20 | TC-20 |
| C21 | PC-21 | FC-21 | TC-21 |
| C22 | PC-22 | FC-22 | TC-22 |
| C23 | PC-23 | FC-23 | TC-23 |
| C24 | PC-24 | FC-24 | TC-24 |

TABLE 1-continued
Structures of 2β-piperazino-androstane derivatives.
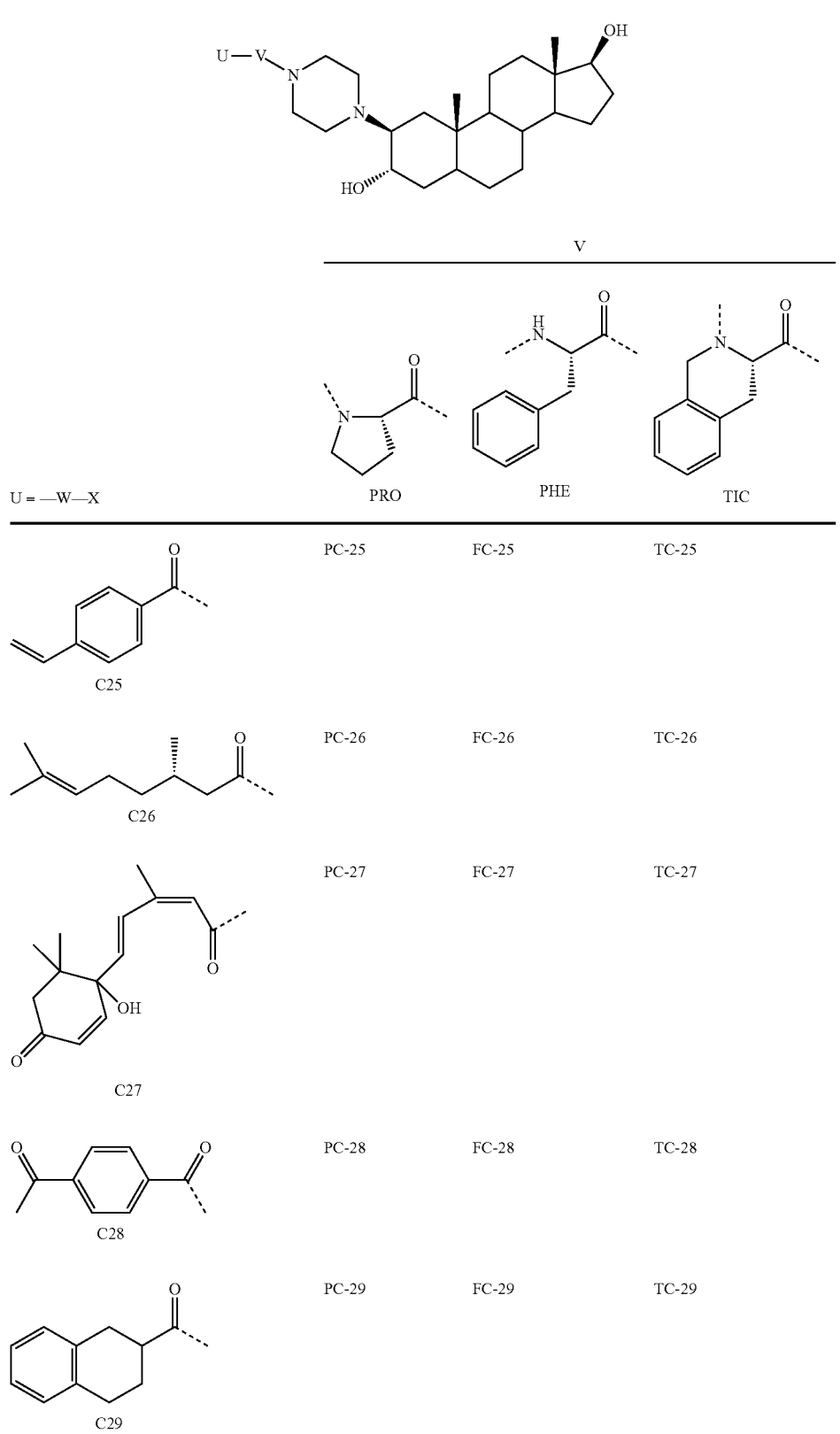

TABLE 1-continued
Structures of 2β-piperazino-androstane derivatives.
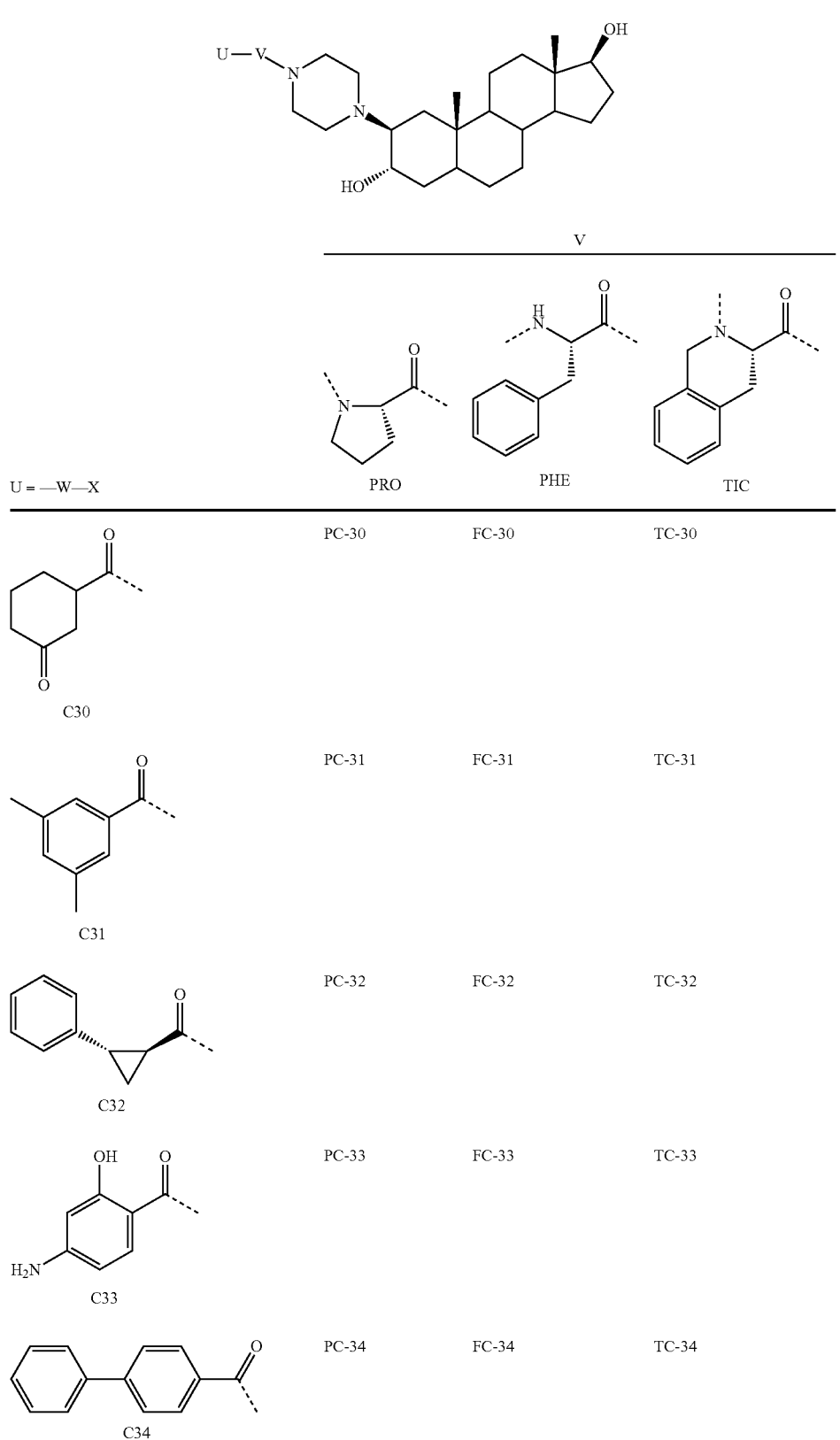

TABLE 1-continued
Structures of 2β-piperazino-androstane derivatives.
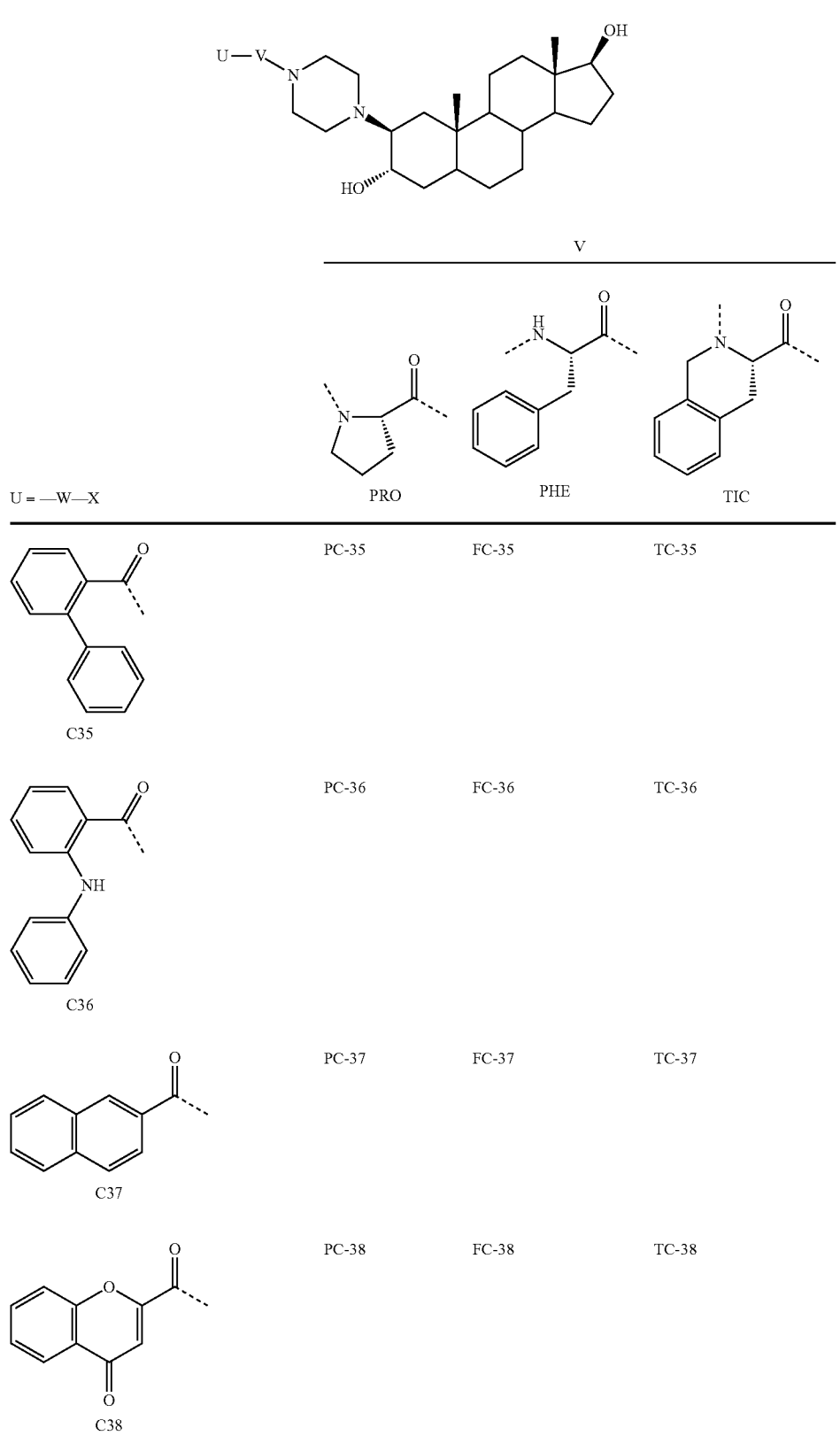

TABLE 1-continued
Structures of 2β-piperazino-androstane derivatives.
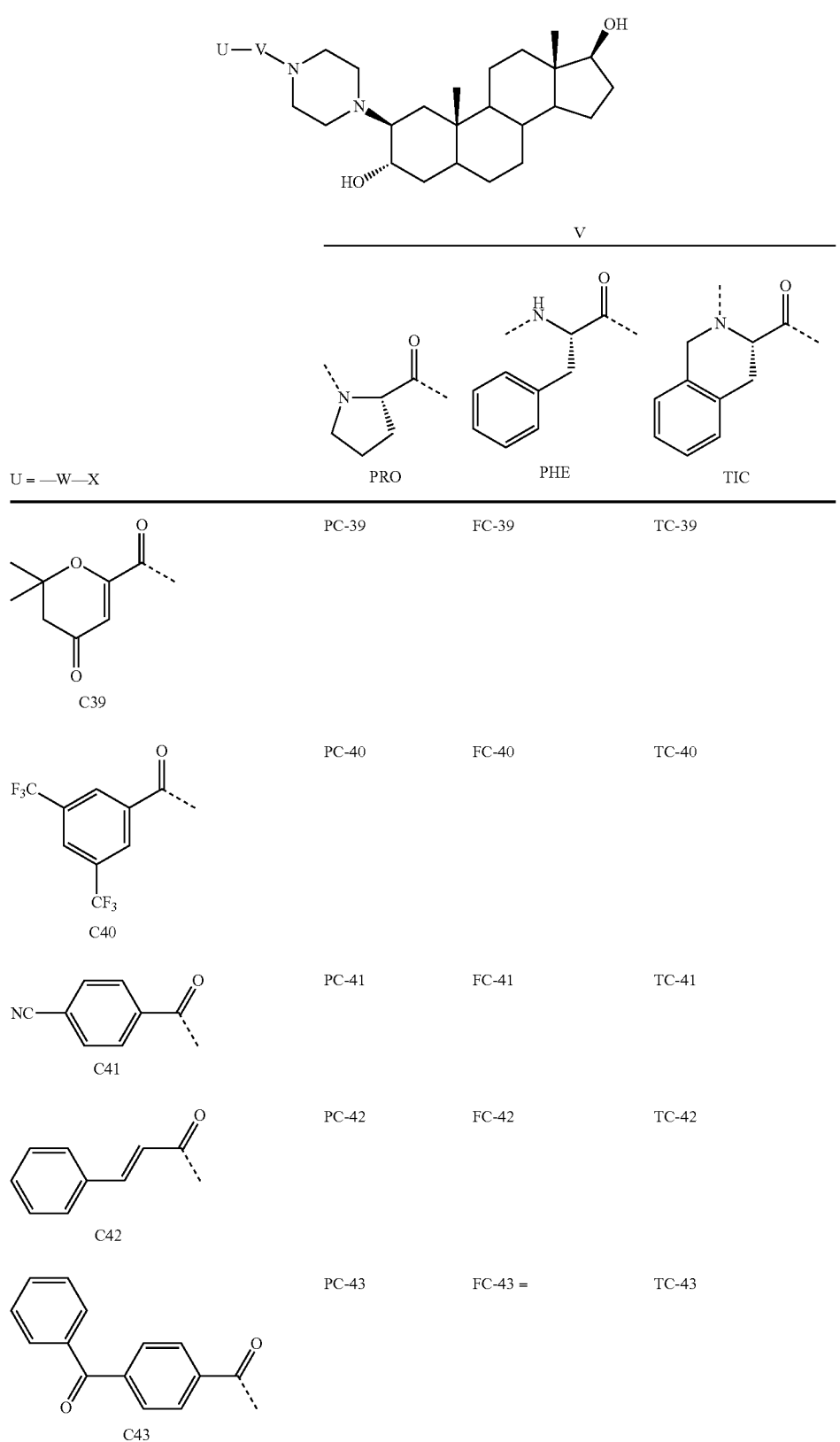
| U = —W—X | PRO | PHE | TIC |
|---|---|---|---|
| C39 | PC-39 | FC-39 | TC-39 |
| C40 | PC-40 | FC-40 | TC-40 |
| C41 | PC-41 | FC-41 | TC-41 |
| C42 | PC-42 | FC-42 | TC-42 |
| C43 | PC-43 | FC-43 = | TC-43 |

TABLE 1-continued
Structures of 2β-piperazino-androstane derivatives.
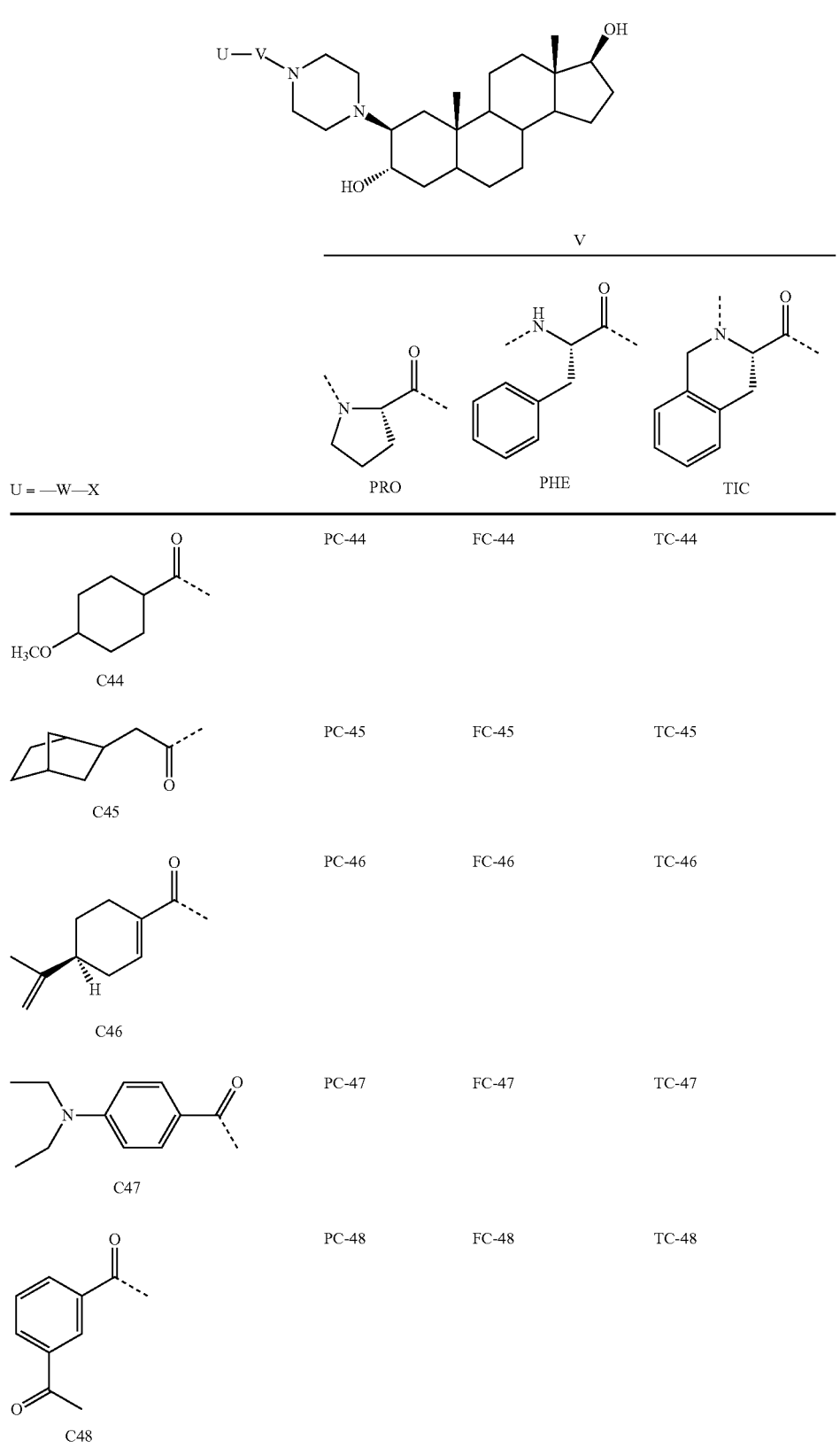
| U = —W—X | PRO | PHE | TIC |
|---|---|---|---|
| C44 | PC-44 | FC-44 | TC-44 |
| C45 | PC-45 | FC-45 | TC-45 |
| C46 | PC-46 | FC-46 | TC-46 |
| C47 | PC-47 | FC-47 | TC-47 |
| C48 | PC-48 | FC-48 | TC-48 |

TABLE 1-continued
Structures of 2β-piperazino-androstane derivatives.
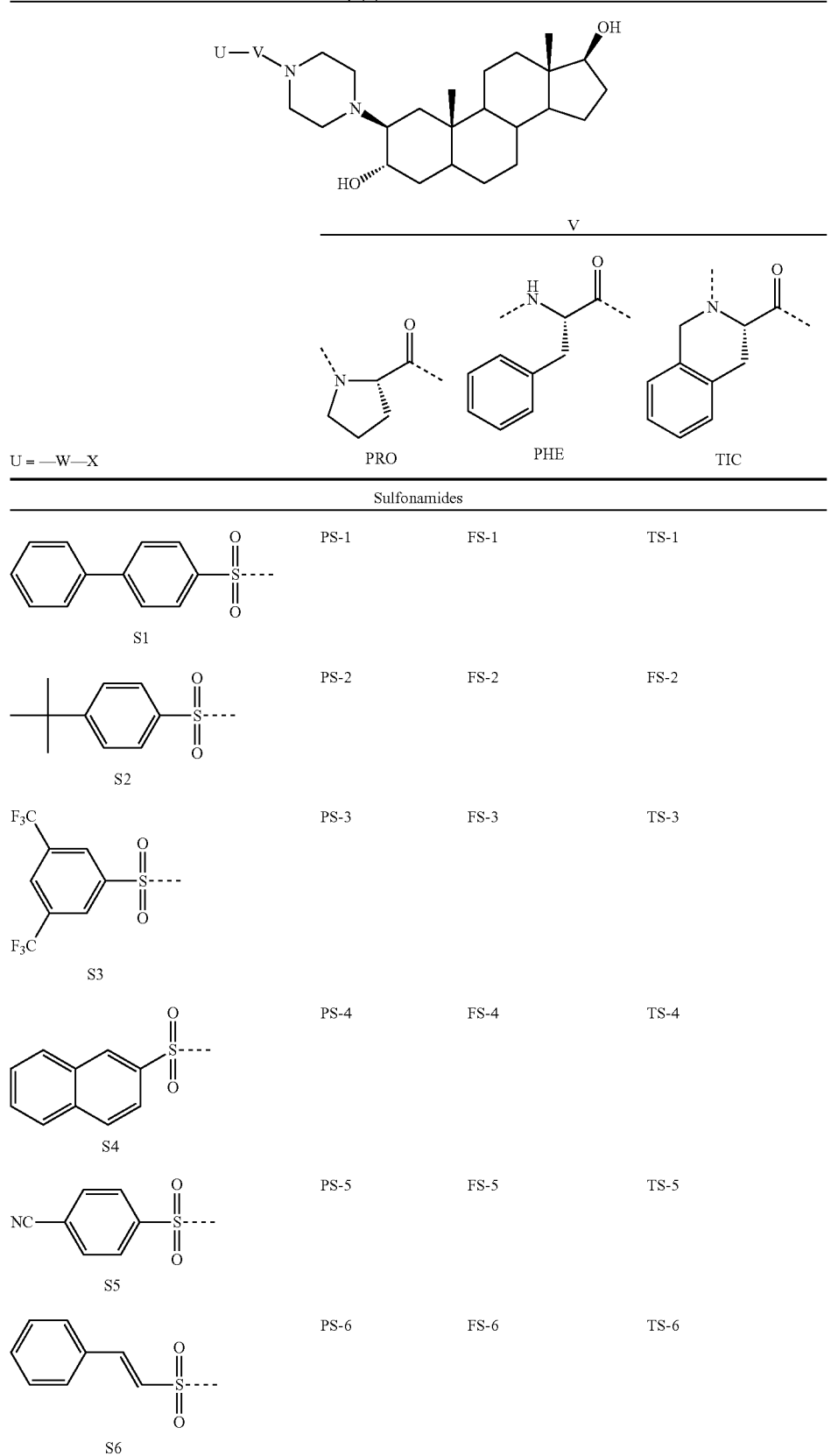
| U = —W—X | PRO | PHE | TIC |
|---|---|---|---|
| Sulfonamides | | | |
| S1 | PS-1 | FS-1 | TS-1 |
| S2 | PS-2 | FS-2 | FS-2 |
| S3 | PS-3 | FS-3 | TS-3 |
| S4 | PS-4 | FS-4 | TS-4 |
| S5 | PS-5 | FS-5 | TS-5 |
| S6 | PS-6 | FS-6 | TS-6 |

TABLE 1-continued
Structures of 2β-piperazino-androstane derivatives.
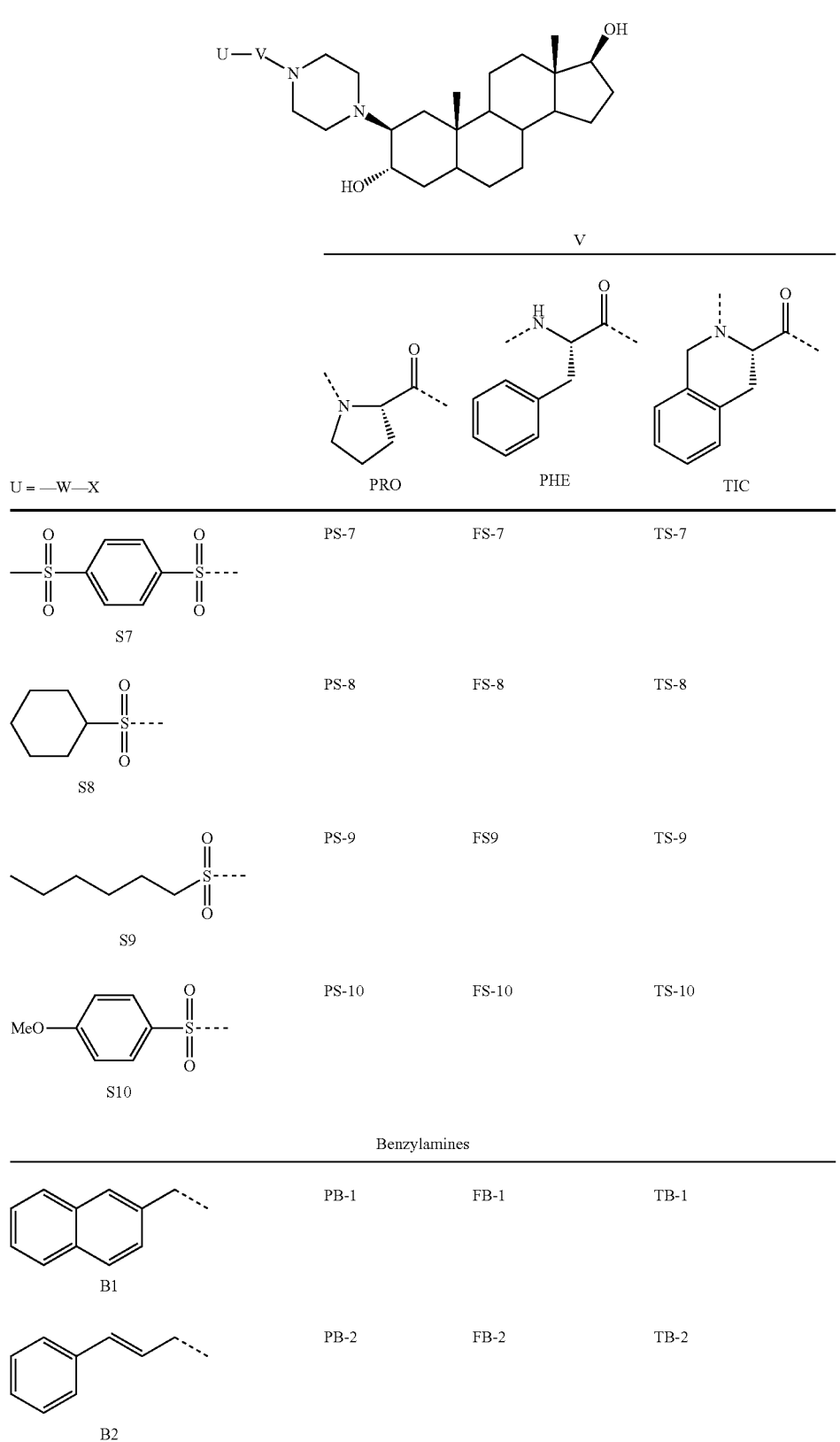
| U = —W—X | PRO | PHE | TIC |
|---|---|---|---|
| S7 | PS-7 | FS-7 | TS-7 |
| S8 | PS-8 | FS-8 | TS-8 |
| S9 | PS-9 | FS9 | TS-9 |
| S10 | PS-10 | FS-10 | TS-10 |
| Benzylamines | | | |
| B1 | PB-1 | FB-1 | TB-1 |
| B2 | PB-2 | FB-2 | TB-2 |

TABLE 1-continued
Structures of 2β-piperazino-androstane derivatives.
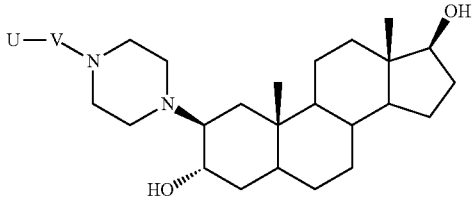
V
| U = —W—X | 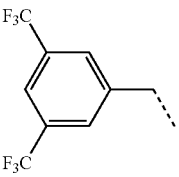<br>PRO | <br>PHE | <br>TIC |
|---|---|---|---|
| <br>B3 | PB-3 | FB-3 | TB-3 |
| 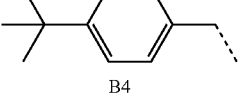<br>B4 | PB-4 | FB-4 | TB-4 |
| <br>B5 | PB-5 | FB-5 | TB-5 |
| <br>B6 | PB-6 | FB-6 | TB-6 |
Ureas
| <br>I1 | PI-1 | FI-1 | TI-1 |
|---|---|---|---|

TABLE 1-continued
Structures of 2β-piperazino-androstane derivatives.
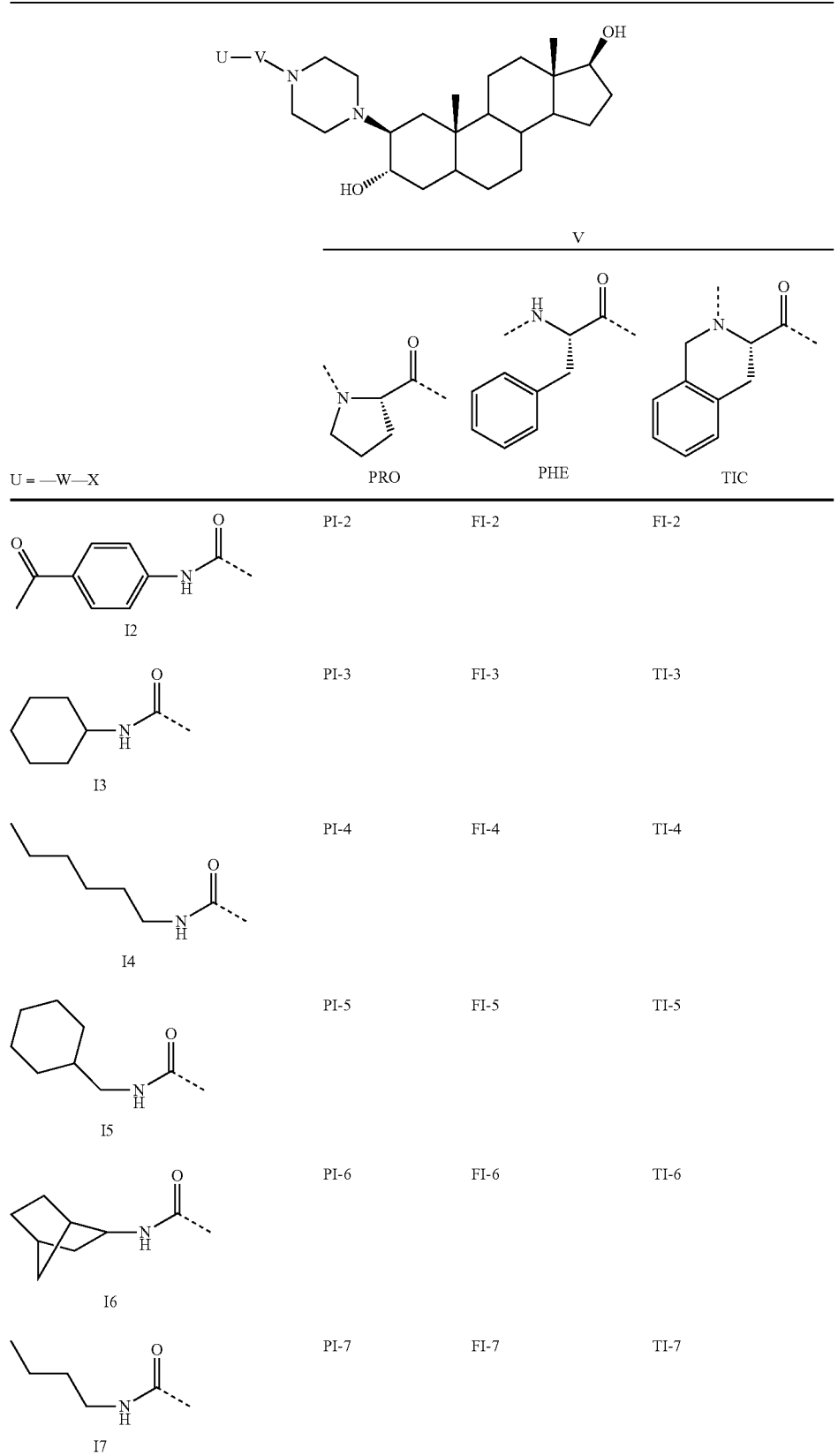

TABLE 1-continued
Structures of 2β-piperazino-androstane derivatives.
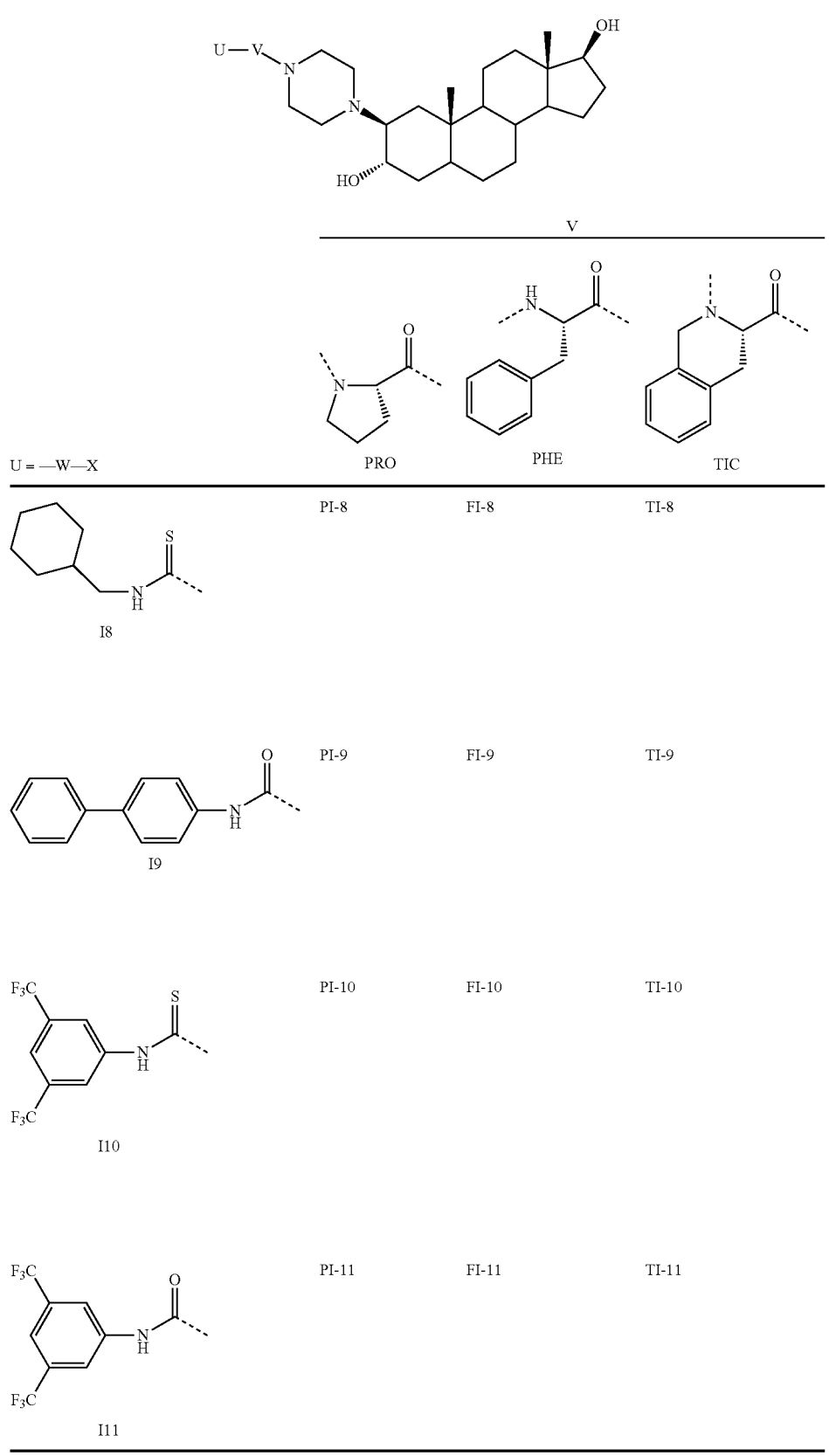

In accordance with an embodiment of the present disclosure, the preparation of 2β-N-Fmoc-piperazino-5α-pregnan-3α,17β-diol (15) is illustrated hereinbelow in Scheme 3.

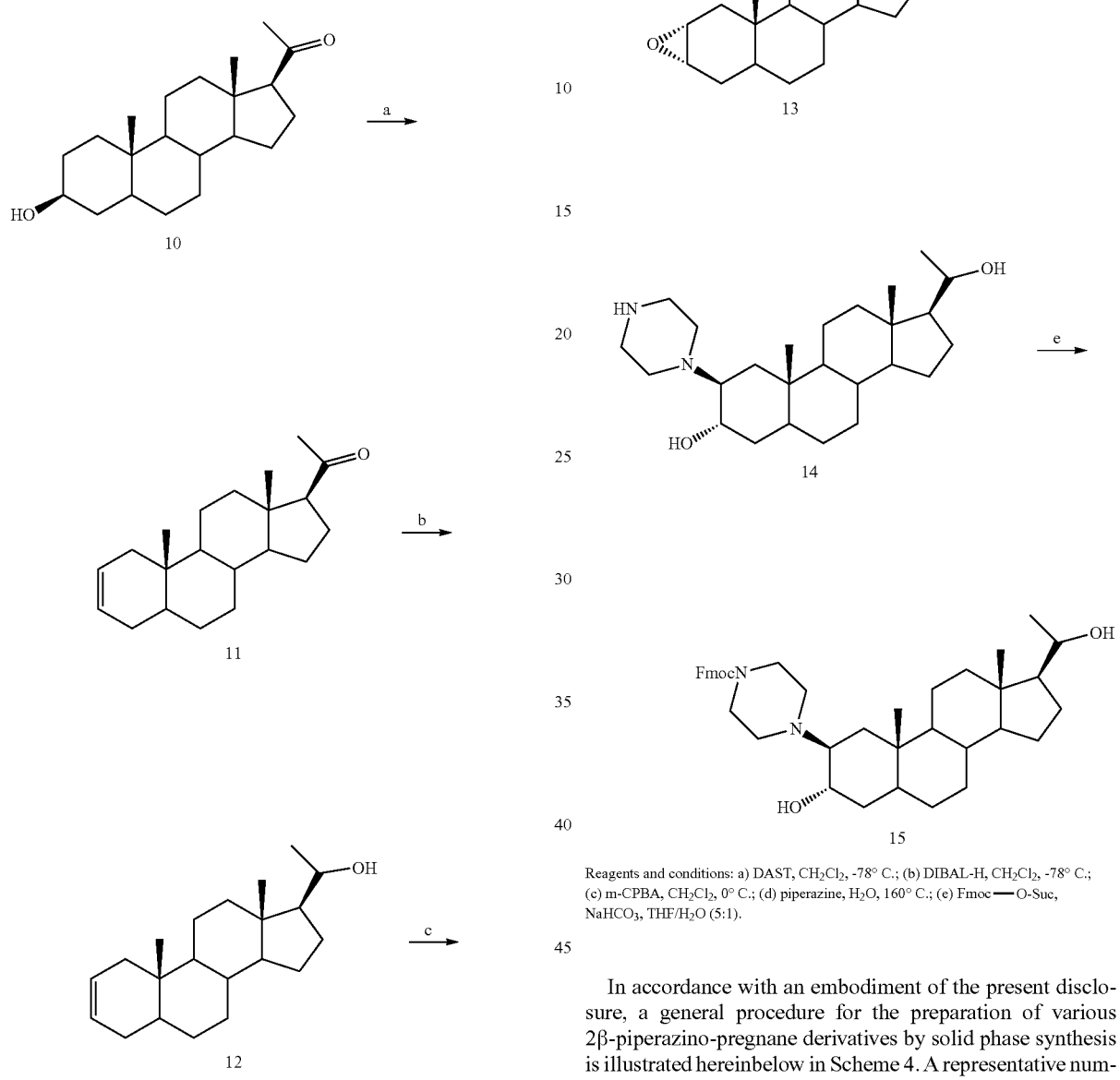

Reagents and conditions: a) DAST, CH$_2$Cl$_2$, -78° C.; (b) DIBAL-H, CH$_2$Cl$_2$, -78° C.; (c) m-CPBA, CH$_2$Cl$_2$, 0° C.; (d) piperazine, H$_2$O, 160° C.; (e) Fmoc—O-Suc, NaHCO$_3$, THF/H$_2$O (5:1).

In accordance with an embodiment of the present disclosure, a general procedure for the preparation of various 2β-piperazino-pregnane derivatives by solid phase synthesis is illustrated hereinbelow in Scheme 4. A representative number of derivatives are illustrated in Table 2.

Scheme 4:

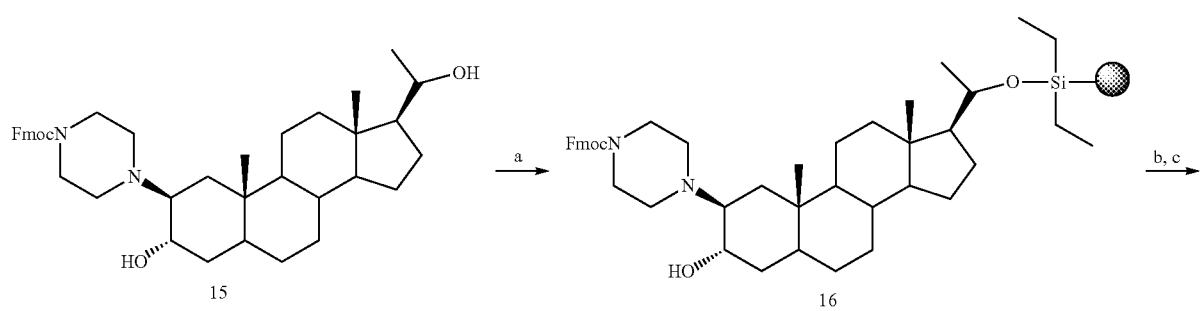

-continued

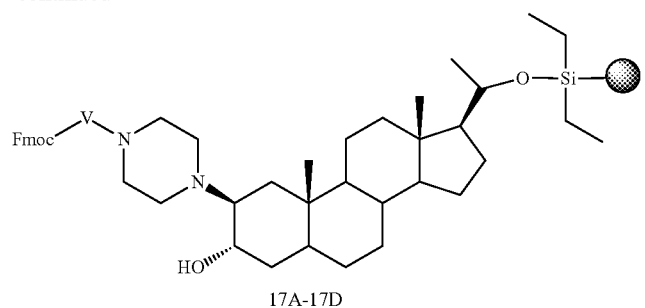

17A-17D

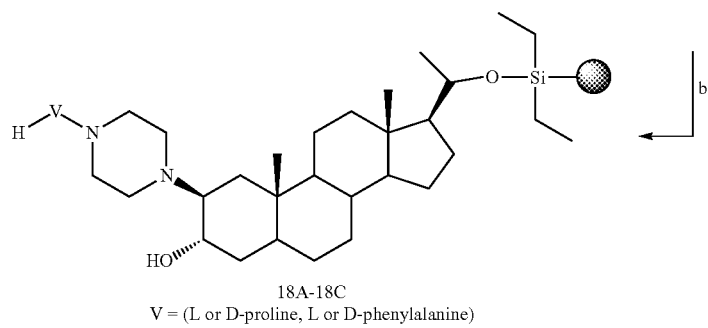

18A-18C
V = (L or D-proline, L or D-phenylalanine)

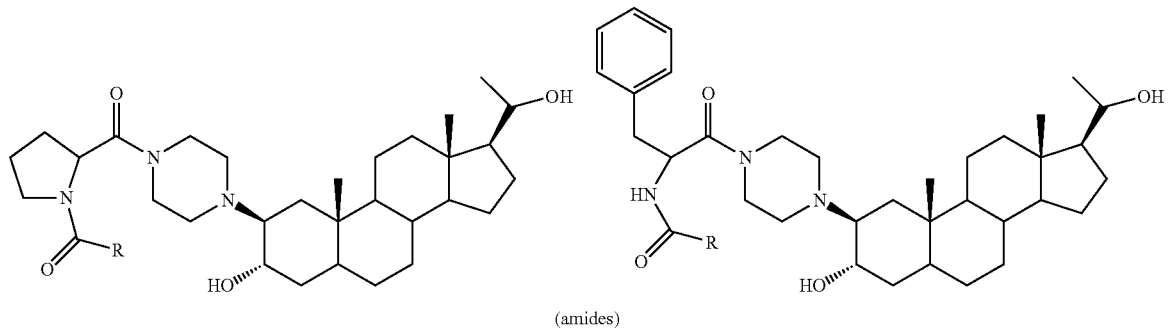

(amides)

LPC37; LPC38; LPC39; LPC41; LPC42; LPC46; LPC48
LFC37; LFC38, LFC39; LFC41; LFC42; LFC46; LFC48
DPC27; DPC38, DPC39; DPC41; DPC42; DPC46; DPC48
DFC37; DFC38; DFC39; DFC41; DFC42; DFC46; DFC48
(see Table 2)

Reagents and condition: (a) i) PS-DES-Cl resin, imidazole, $CH_2Cl_2$, rt.; (b) 20% piperidine in $CH_2Cl_2$, (v/v), rt; (c) N-Fmoc-amino acid (Fmoc-PRO-OH, Fmoc-PHE-OH), PyBOP, HOBt, DIPEA, DMF, rt; (d) carboxylic acid (RCOOH), PyBOP, HOBt, DIPEA, DMF, rt; (e) i) HCl (2M)/MeOH (AcCl + MeOH) in $CH_2Cl_2$ (20:80, v/v); ii) 10% $NaHCO_3$.

TABLE 2
Structures of 2β-piperazino-pregnane derivatives.
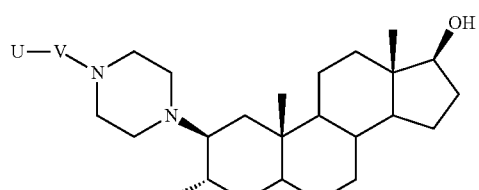
| U = —W—X | L-PRO | L-PHE | D-PRO | D-PHE |
|---|---|---|---|---|
| Amides | | | | |
| 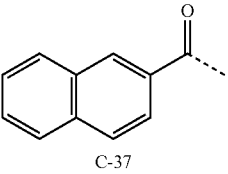<br>C-37 | LPC-37 | LFC-37 | DPC-37 | DFC-37 |
| 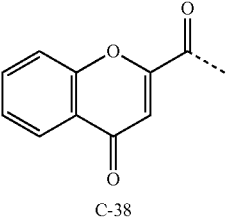<br>C-38 | LPC-38 | LFC-38 | DPC-38 | DFC-38 |
| 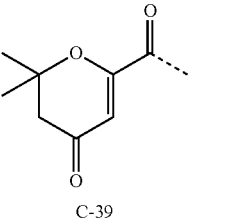<br>C-39 | LPC-39 | LFC-39 | DPC-39 | DFC-39 |
| 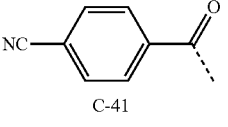<br>C-41 | LPC-41 | LFC-41 | DPC-41 | DFC-41 |
| 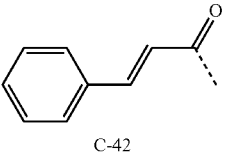<br>C-42 | LPC-42 | LFC-42 | DPC-42 | DFC-42 |

TABLE 2-continued

Structures of 2β-piperazino-pregnane derivatives.

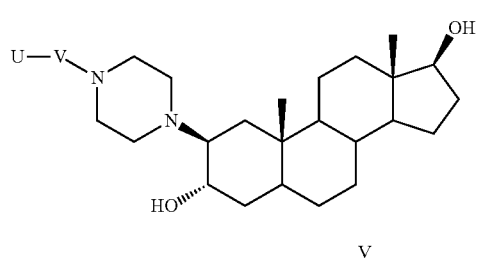

V

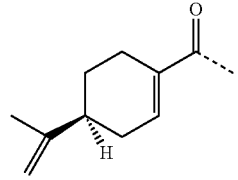

| U = —W—X | L-PRO | L-PHE | D-PRO | D-PHE |
|---|---|---|---|---|
| 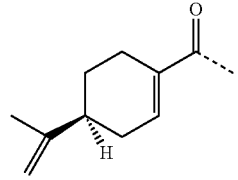<br>C-46 | LPC-46 | LFC-46 | DPC-46 | DFC-46 |
| 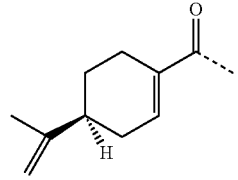<br>C-48 | LPC-48 | LFC-48 | DPC-48 | DFC-48 |

In accordance with an embodiment of the present disclosure, a general procedure for the preparation of various 2β-piperazino-andrstane and 2β-piperazino-pregnane derivatives by solution phase synthesis is illustrated hereinbelow in Scheme 5.

Scheme 5:

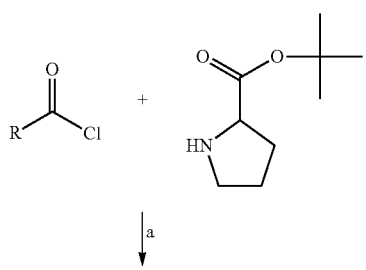

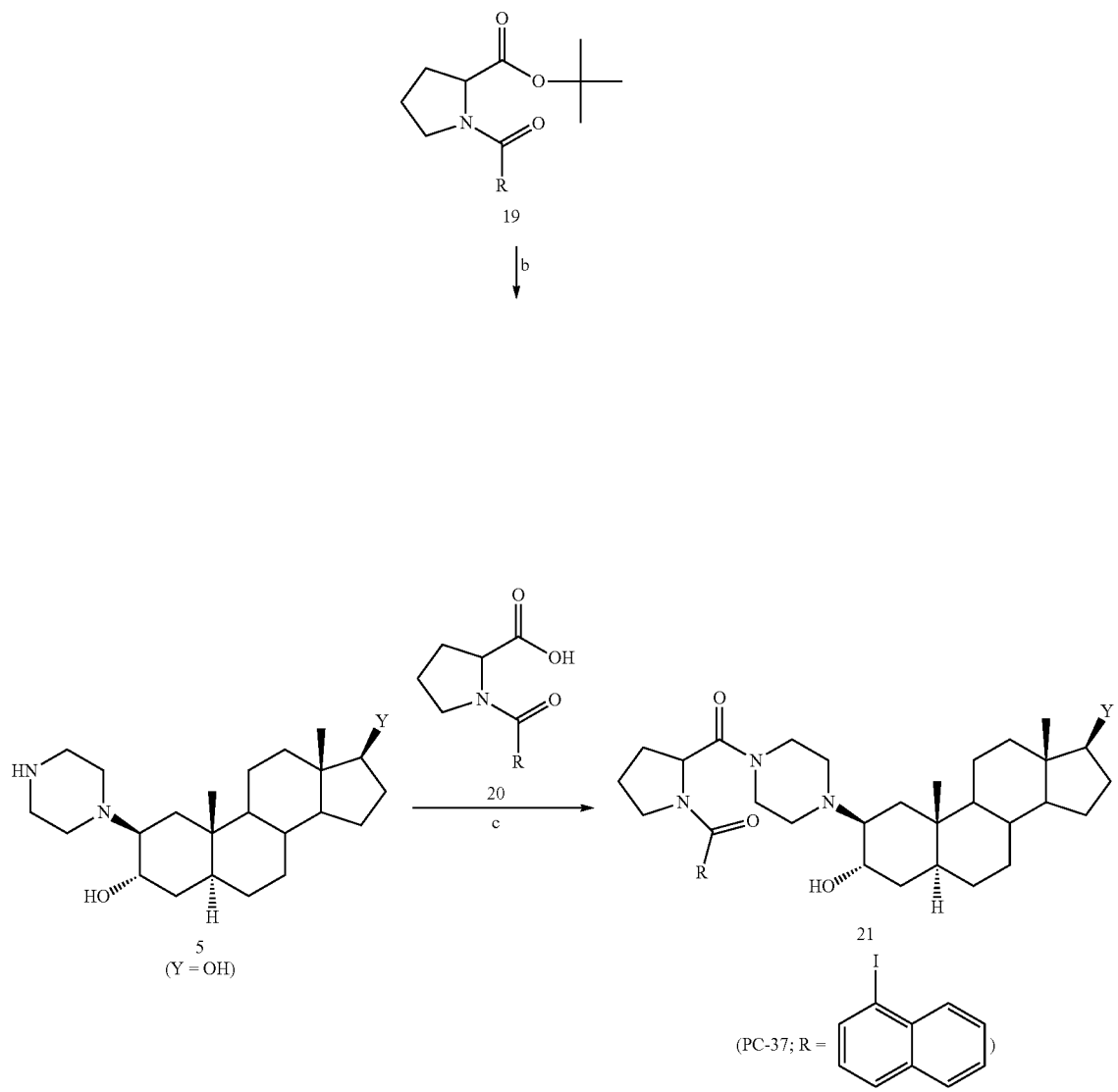
Reagents and conditions: (a) TEA, CH$_2$Cl$_2$; (b) TFA in CH$_2$Cl$_2$ (95:5); (c) 5, PyBOP, HOBt, DIPEA, DMF, rt.
In accordance with an embodiment of the present disclosure, the preparation of {4-[(2β,3α,5α,17α)-3,17-dihydroxypregn-20-yn-2-yl]piperazin-1-yl}[(2S)-1-(naphthalen-2-ylcarbonyl)pyrrolidin-2-yl]methanone (26) is illustrated hereinbelow in Scheme 6.
Scheme 6:
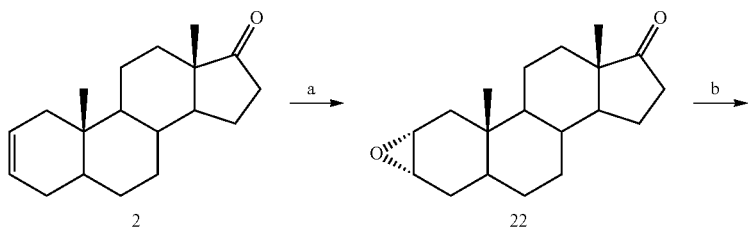

-continued
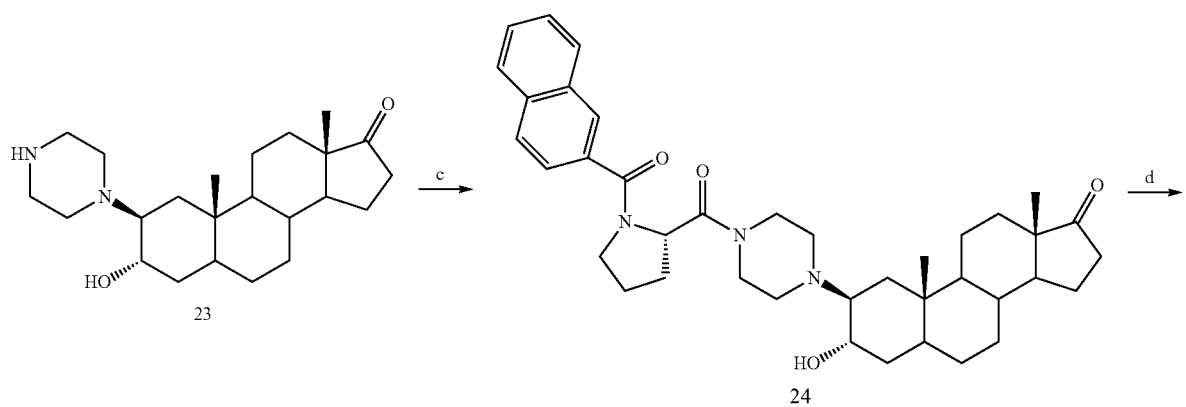
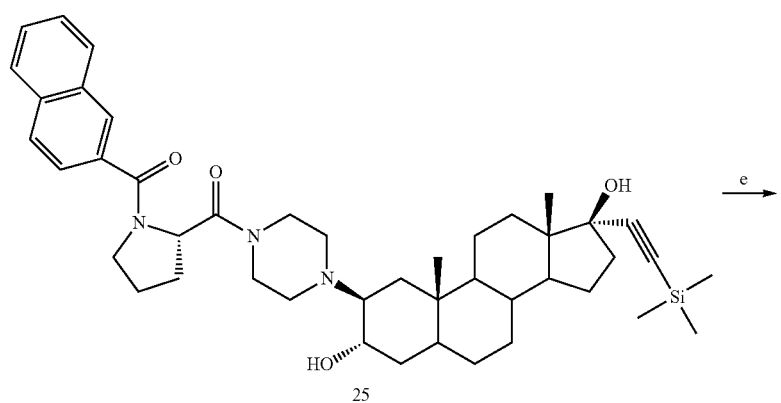
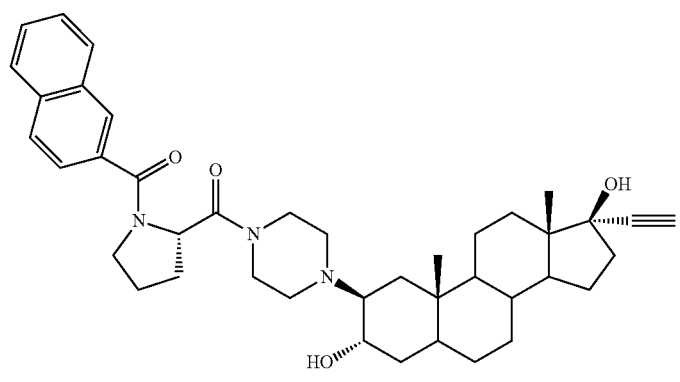
Reagents and conditions: (a) m-CPBA, DCM, 0° C.; (b) piperazine, H₂O, 150° C.; (c) 1-(naphtalen-2-ylcarbonyl)-L-proline, PyBOP, HOBt, DIPEA, DMF, rt; (d) trimethylsilylethinyl, MeLi, Ether/THF; (e) MeOH, K₂CO₃ (10%), rt.

In accordance with an embodiment of the present disclosure, the preparation of {4-[(2β,3α,17α)-3,17-dihydroxy-17-methylandrostan-2-yl]piperazin-1-yl}[(2S)-1-(naphthalen-2-ylcarbonyl)pyrrolidin-2-yl]methanone (30) is illustrated hereinbelow in Scheme 7.

Scheme 7:

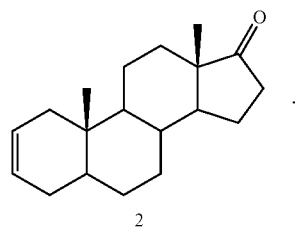

2

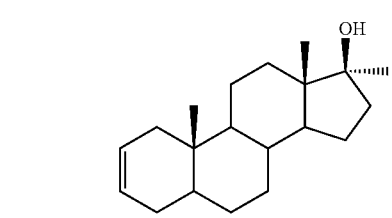

27

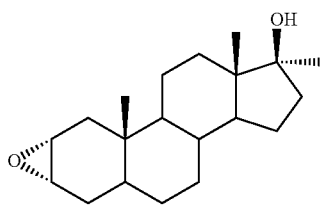

28

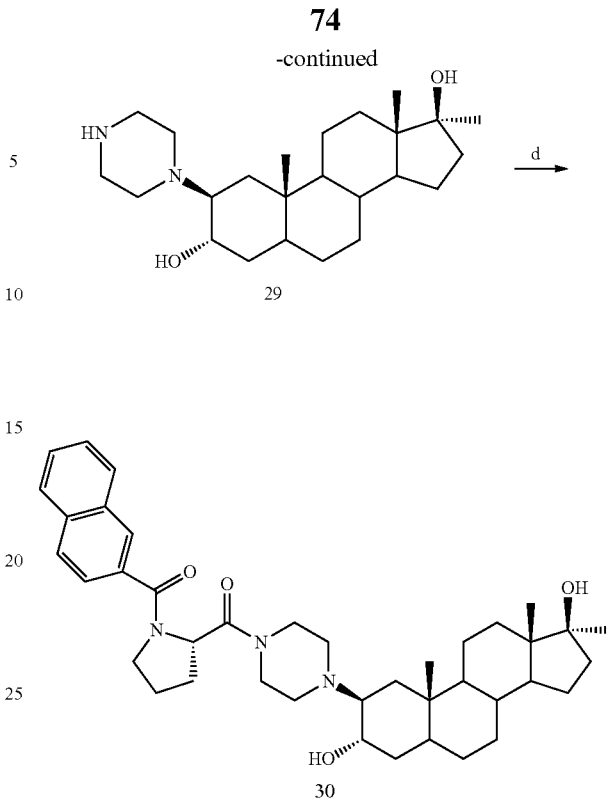

29

30

Reagents and conditions: (a) methylmagnesium bromide, THF, 0° C. to rt; (b) m-CPBA, DCM, rt; (c) piperazine, H₂O, 150° C.; (d) 1-(naphthalen-2-ylcarbonyl)-L-proline, PyBOP, HOBt, DIPEA, DMF, rt.

In accordance with an embodiment of the present disclosure, the preparation of {4-[(2β,3α,17β)-3,17-dihydroxyandrostan-2-yl]piperazin-1-yl}[(2S)-1-(isoquinolin-3-ylcarbonyl) pyrrolidin-2-yl]methanone (31); {4-[(2β,3α, 17β)-3,17-dihydroxyandrostan-2-yl]piperazin-1-yl}[(2S)-1-(quinolin-6-ylcarbonyl) pyrrolidin-2-yl]methanone (32); and {4-[(2β, 3α,17β)-3,17-dihydroxyandrostan-2-yl]piperazin-1-yl}[(2S)-1-(quinolin-2-ylcarbonyl)pyrrolidin-2-yl]methanone (33) is illustrated hereinbelow in Scheme 8.

Scheme 8:

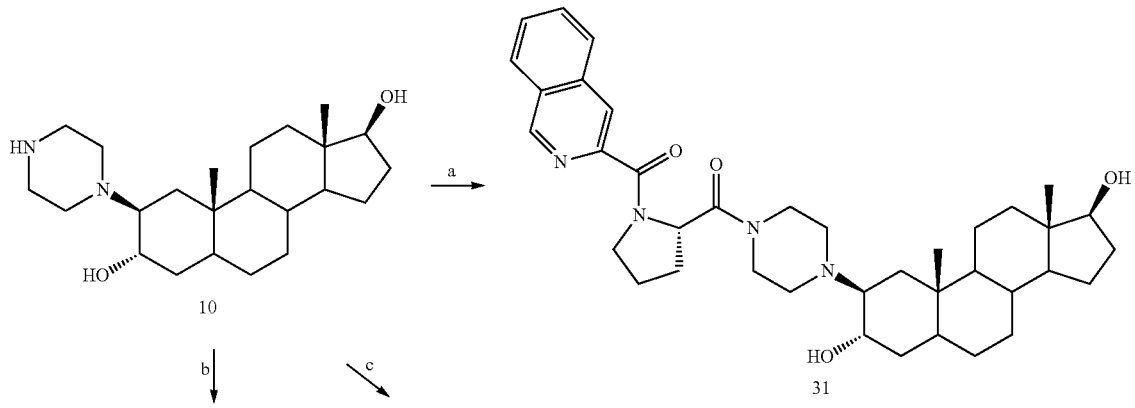

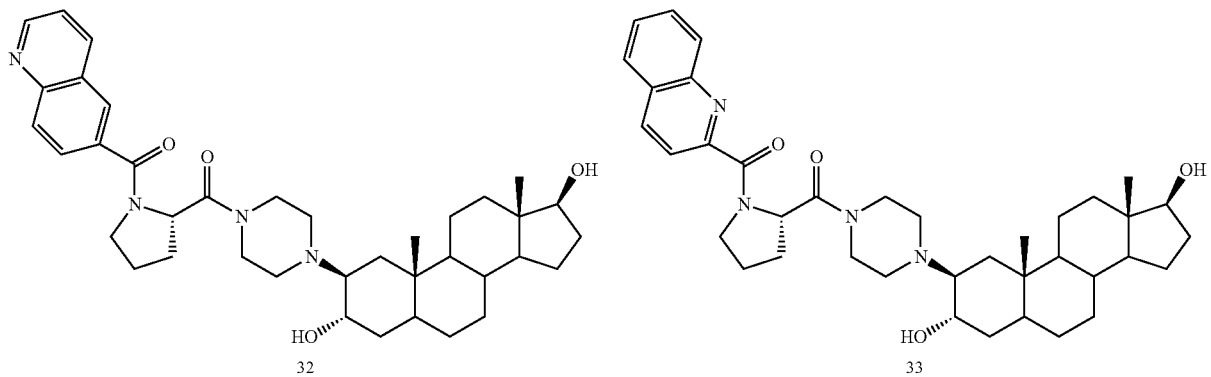

Reagents and conditions: (a) (a) 1-(isoquinolin-3-ylcarbonyl)-L-proline, PyBOP, HOBt, DIPEA, DMF, rt; (b) 1-(quinolin-6-ylcarbonyl)-L-proline, PyBOP, HOBt, DIPEA, DMF, rt; (c) 1-(quinolin-2-ylcarbonyl)-L-proline, PyBOP, HOBt, DIPEA, DMF, rt.

In accordance with an embodiment of the present disclosure, the preparation of {4-[(2β,3α,17β)-3-hydroxy-17-methoxyandrostan-2-yl]piperazin-1-yl}[(2S)-1-(naphthalen-2-ylcarbonyl)pyrrolidin-2-yl]methanone (37) is illustrated hereinbelow in Scheme 9.

Scheme 9:

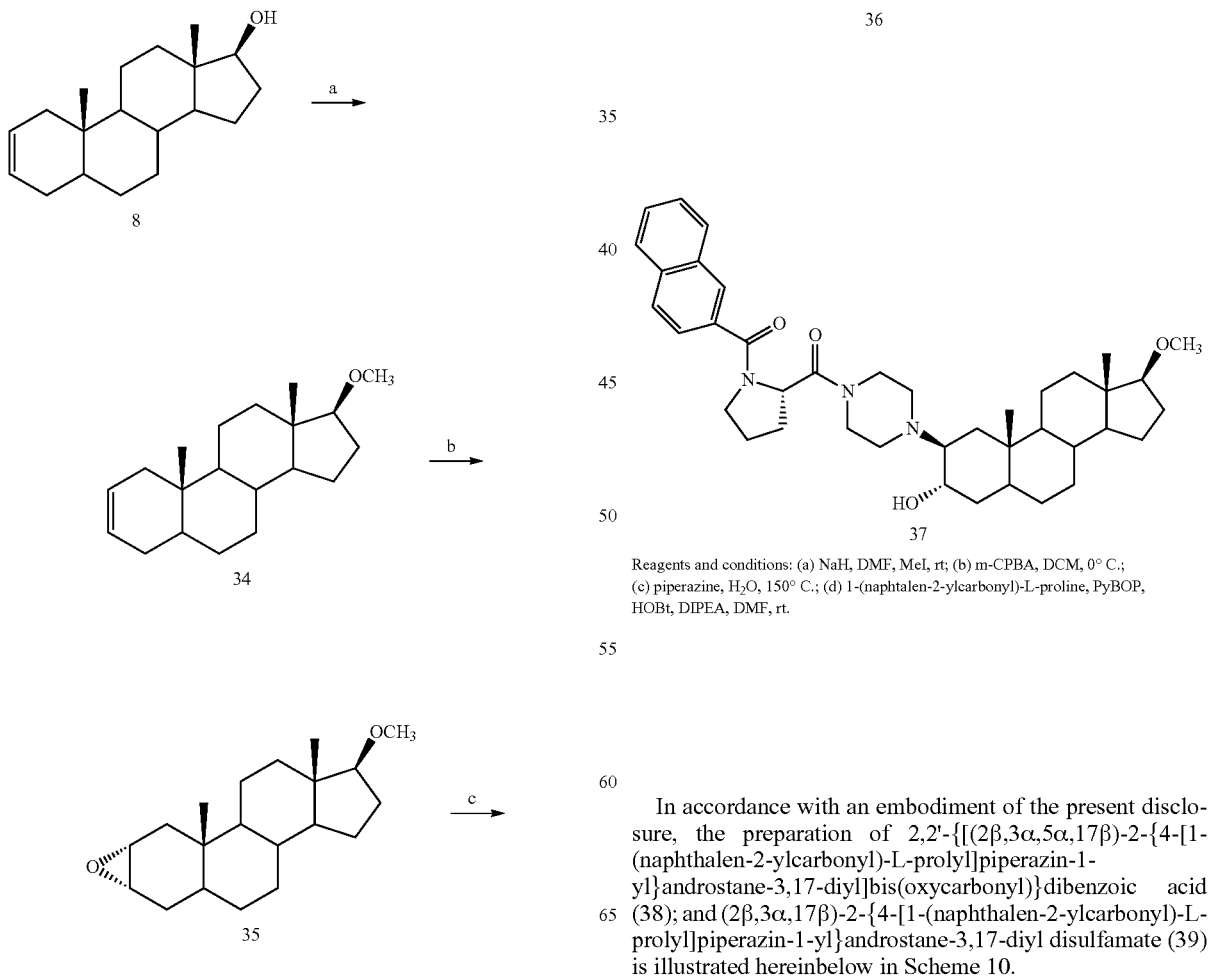

Reagents and conditions: (a) NaH, DMF, MeI, rt; (b) m-CPBA, DCM, 0° C.; (c) piperazine, H₂O, 150° C.; (d) 1-(naphtalen-2-ylcarbonyl)-L-proline, PyBOP, HOBt, DIPEA, DMF, rt.

In accordance with an embodiment of the present disclosure, the preparation of 2,2'-{[(2β,3α,5α,17β)-2-{4-[1-(naphthalen-2-ylcarbonyl)-L-prolyl]piperazin-1-yl}androstane-3,17-diyl]bis(oxycarbonyl)}dibenzoic acid (38); and (2β,3α,17β)-2-{4-[1-(naphthalen-2-ylcarbonyl)-L-prolyl]piperazin-1-yl}androstane-3,17-diyl disulfamate (39) is illustrated hereinbelow in Scheme 10.

Scheme 10:
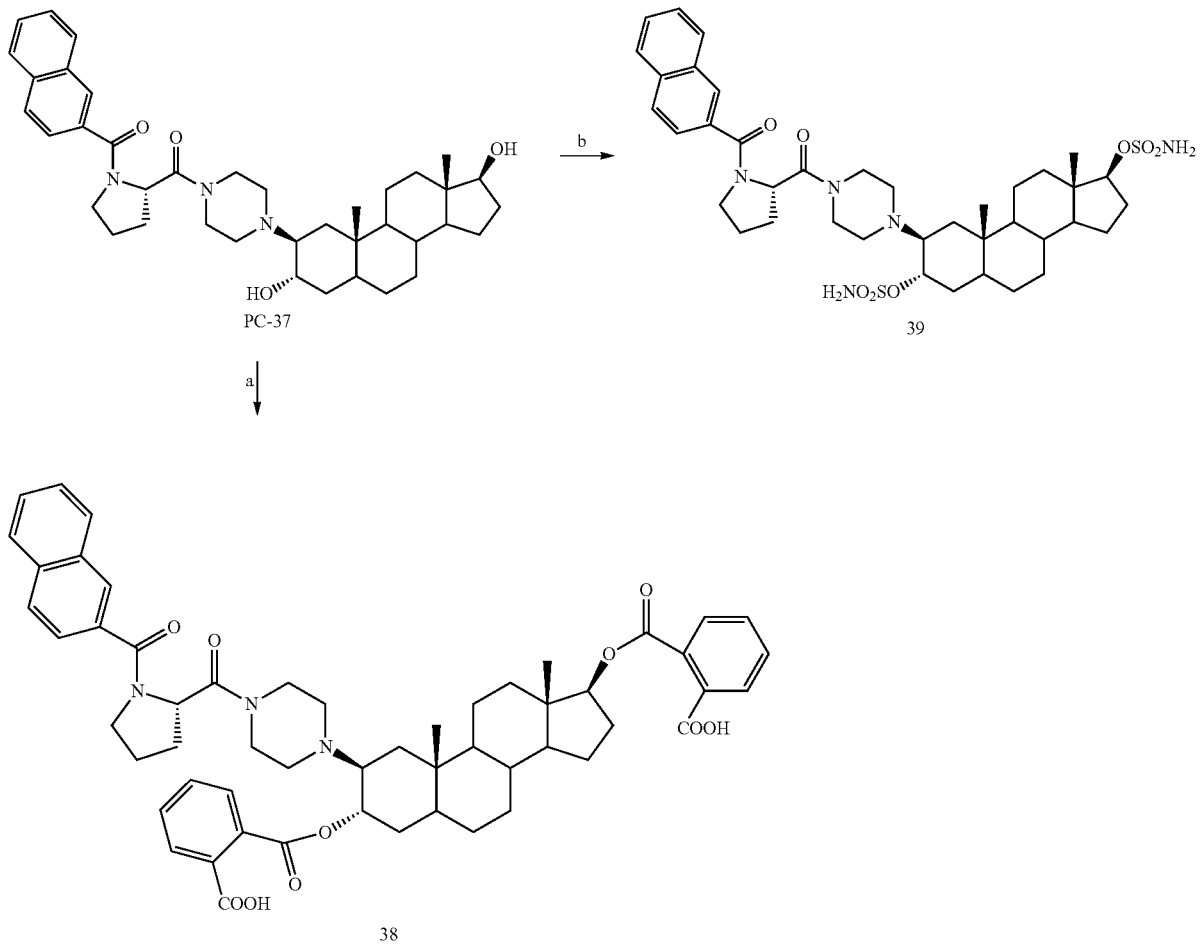
Reagents and conditions: (a) phthalic anhydride, DMAP, pyridine; (b) sulfamoyl chloride, 2,6-di-tert-butylmethylpyridine, DCM, rt.
In accordance with an embodiment of the present disclosure, the preparation of {4-[(2β,3α,5α,17α)-3,17-dihydroxypregn-20-yn-2-yl]piperazin-1-yl}[(2S)-1-(naphthalen-1-ylcarbonyl)pyrrolidin-2-yl]methanone (42) is illustrated hereinbelow in Scheme 11.
Scheme 11:
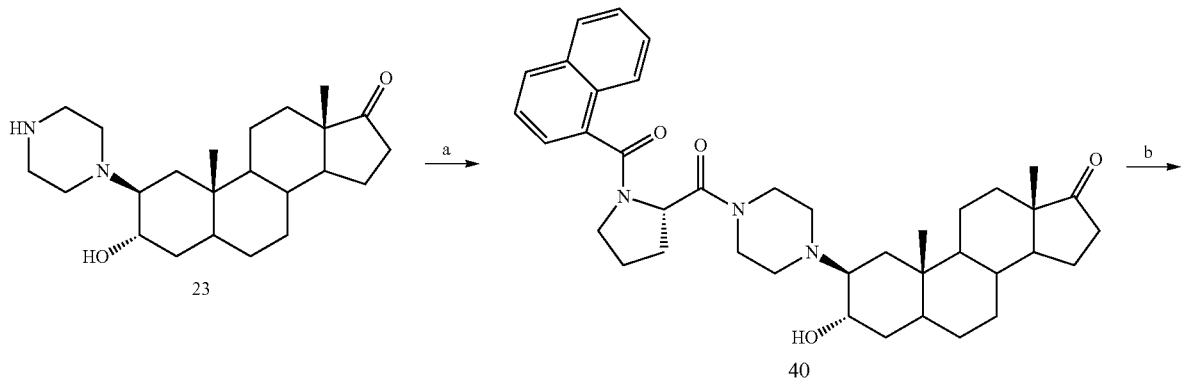

-continued

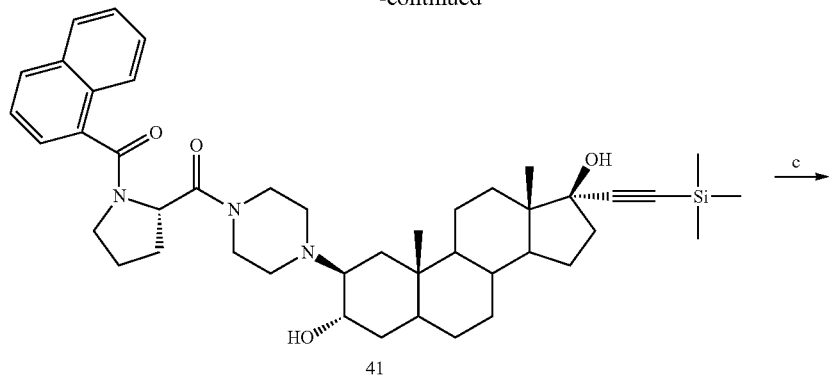
41

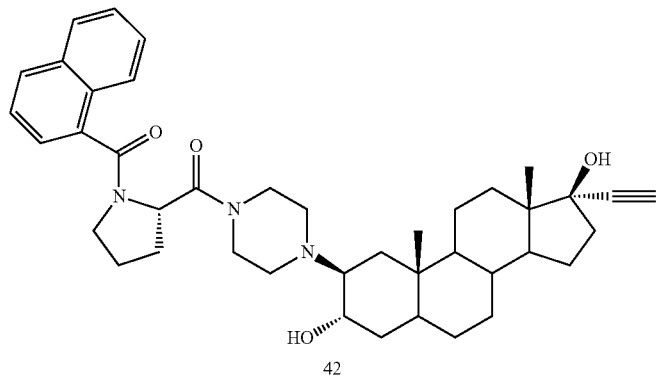
42

Reagents and conditions: (a) 1-(naphtalen-1-ylcarbonyl)-L-proline, PyBOP, HOBt, DIPEA, DMF, rt; (b) Trimethylsilylethinyl, MeLi, Ether/THF; (c) MeOH, $K_2CO_3$ (10%), rt.

In accordance with an embodiment of the present disclosure, the preparation of {4-[(2β,3α,5α,17α)-3,17-dihydroxypregn-20-yn-2-yl]piperazin-1-yl}[(2S)-1-(isoquinolin-3-ylcarbonyl)pyrrolidin-2-yl]methanone (45) is illustrated hereinbelow in Scheme 12.

Scheme 12:

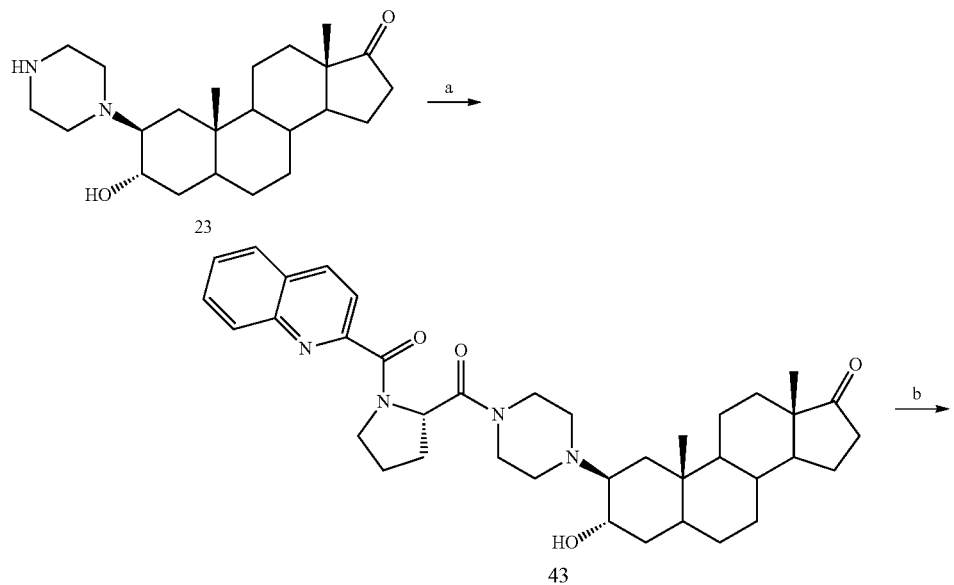

-continued

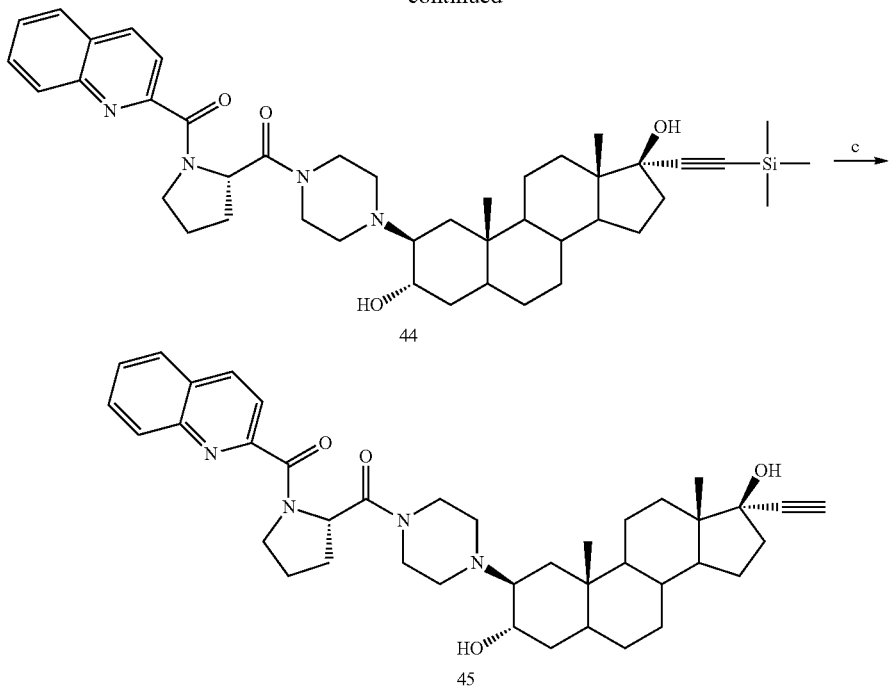

Reagents and conditions: (a) 1-(isoquinolin-3-ylcarbonyl)-L-proline, PyBOP, HOBt, DIPEA, DMF, rt; (b) Trimethylsilylethinyl, MeLi, Ether/THF; (c) MeOH, K$_2$CO$_3$ (10%), rt In accordance with an embodiment of the present disclosure, the preparation of {4-[(2β,3α,5α,17β)-3,17-dihydroxyandrostan-2-yl]piperazin-1-yl}[(2S)-1-(naphthalen-1-ylcarbonyl)pyrrolidin-2-yl]methanone (46); {4-[(2β,3α,5α,17β)-3,17-dihydroxyandrostan-2-yl]piperazin-1-yl} {(2S)-1-[(1-oxidoquinolin-3-yl)carbonyl]pyrrolidin-2-yl}methanone (47); and {4-[(2β,3α,5α,17β)-3,17-dihydroxyandrostan-2-yl]-4-oxidopiperazin-1-yl}[(2S)-1-(quinolin-3-ylcarbonyl)pyrrolidin-2-yl]methanone(49) is illustrated hereinbelow in Scheme 13.

Scheme 13:
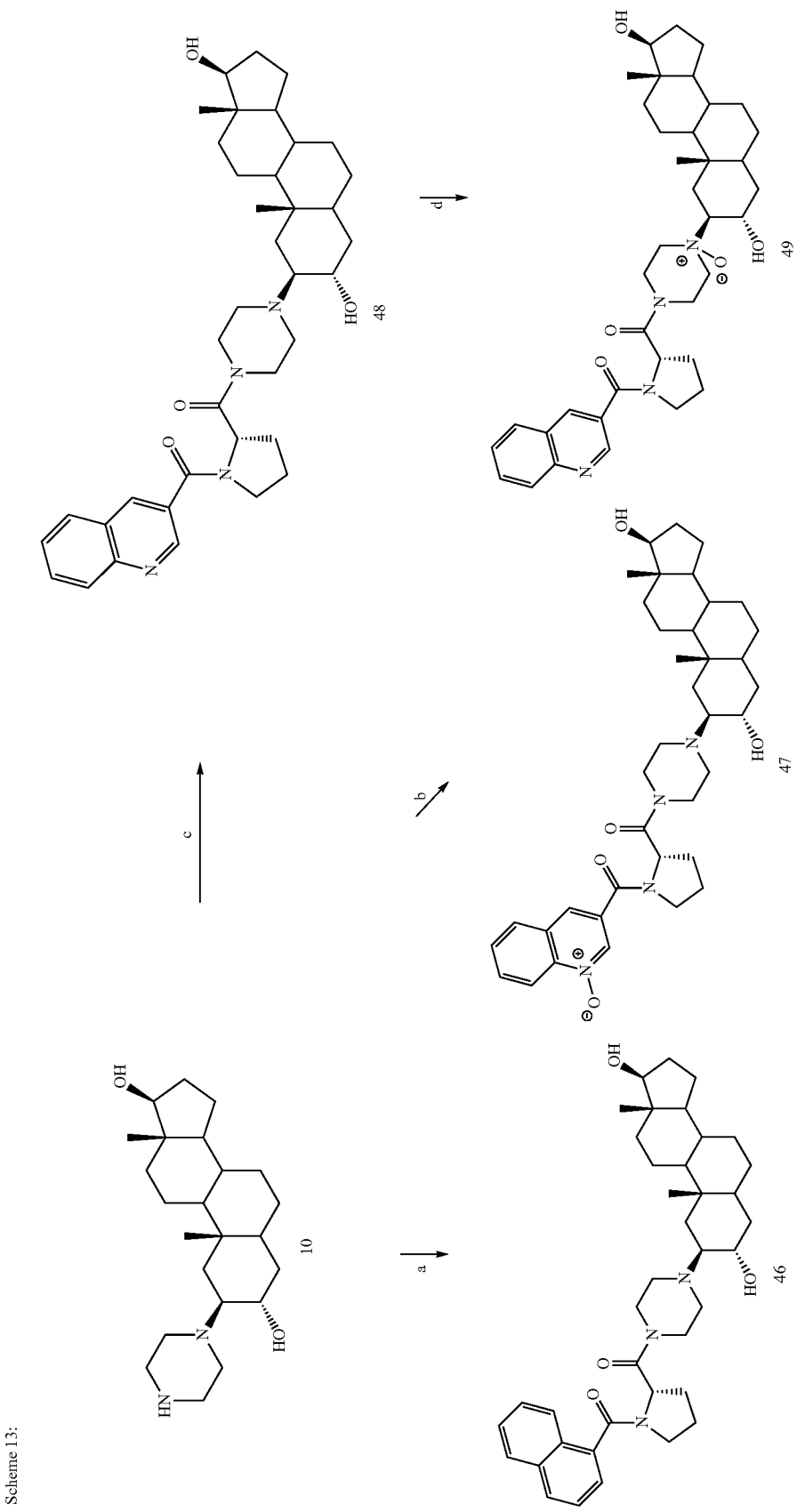
Reagents and conditions: (a) 1-(naphthalen-1-ylcarbonyl)-L-proline, PyBOP, HOBt, DIPEA, DMF, rt; (b) 1-((1-oxidoquinolin-3-yl)carbonyl)-L-proline, PyBOP, HOBt, DIPEA, DMF, rt; (c) 1-(quinolin-3-ylcarbonyl)-L-proline, PyBOP, HOBt, DIPEA, DMF, rt; (d) oxone, MeOH, H₂O.

Biological Activity
Cell Culture

All of the following cell lines were maintained under a $CO_2$ humidified atmosphere at 37° C. The culture media were changed every 3-4 days and the cells were split once a week.

Cancer Cells

MCF-7 breast cancer cells were maintained in Dulbecco's Modified Eagle's Medium (DMEM) containing a nutriment mixture F-12 ham (DME-F12) (Sigma, Saint Louis, USA) supplemented with 5% (v/v) fetal bovine serum (FBS), L-glutamine (2 nM), penicillin (100 IU/ml), streptomycin sulphate (50 µg/ml) and estradiol (1 nM). For the assay, DME-F12 was supplemented with 5% (v/v) charcoal-strippes FBS, insulin (50 ng/ml) and the same concentrations of antibiotics as above.

Shionogi mammary carcinoma cells bearing androgen-sensitive (AR+) were routinely grown in Eagle's Minimal Essential Medium (MEM) (Sigma, Saint Louis, USA) supplemented with 5% (v/v) fetal bovine serum (FBS), penicillin (100 IU/ml), streptomycin sulphate (50 µg/ml), 1% (v/v) non-essential amino acids and dihydrotestosterone DHT ($10^{-8}$ M). For the assay, MEM devoid of the pH indicator phenol red was supplemented with 2% (v/v) charcoal-strippes FBS and the same concentrations of antibiotics and non-essential amino acids as above.

LNCaP prostate cancer cells were grown in RPMI-1640 (Sigma, Saint Louis, USA) supplemented with 10% (v/v) FBS, L-glutamine (2 nM), penicillin (100 IU/ml) and streptomycin sulphate (50 µg/ml). For the assay, RPMI-1640 was supplemented with 2% (v/v) charcoal-strippes FBS, insulin (50 ng/ml) and the same concentrations of antibiotics as above.

OVCAR-3 ovarian cancer cells were maintained in RPMI-1640 (Sigma, Saint Louis, USA) supplemented with 20% (v/v) FBS, L-glutamine (2 nM), penicillin (100 IU/ml), streptomycin sulphate (50 µg/ml), insulin (50 ng/ml) and estradiol (1 nM). For the assay, the culture medium was the same, but without estradiol.

MDA-MB-231 (ER−) breast cancer cells, PC-3 (AR−) prostate cancer cells, HL-60 acute promyelocytic leukemia cells and K-562 leukemia cells were routinely grown in suspension in RPMI-1640 (Sigma, Saint Louis, USA) containing 10% (v/v) FBS, L-glutamine (2 nM), penicillin (100 IU/ml) and streptomycin sulphate (50 µg/ml). For the assay, the culture medium was the same.

Normal Cells

WI-38 diploid fibroblasts derived from embryonic human lung were cultured in MEM (devoid of the pH indicator phenol red) supplemented with 10% (v/v) FBS, L-glutamine (2 nM), penicillin (100 IU/ml), streptomycin sulphate (50 µg/ml), sodium pyruvate (1 mM) and non-essential amino acids (0.1 mM).

Lymphocytes from peripheral blood were obtained by veinipuncture from healthy adult donors and mononuclear cells were isolated by density gradient separation using Histopaque (Histopaque-1077; Sigma, Saint Louis, USA). Monocytes were allowed to adhere on the cell culture plastic flask over a period of 6 hours, the lymphocytes were then washed and re-suspended in RPMI-1640 (Sigma, Saint Louis, USA) containing 10% (v/v) FBS, L-glutamine (2 nM), penicillin (100 IU/ml) and streptomycin sulphate (50 µg/ml). For the assay, the culture medium was the same.

Cell Proliferation Assay

The cell proliferation assay was performed using 3-(4,5-dimethylthiazol-2-yl)-5-(3-carboxymethoxyphenyl)2-(4-sulfophenyl)-2H-tetrazolium (MTS) (Cell Titer 96 Aqueous, Promega, USA). MTS is converted into water-soluble colored formazan by dehydrogenase enzymes present in metabolically active cells, which allows the measurement of the number of viable cells. Briefly, cells were plated in 96-well microtiter plates(Becton Dickinson and Company, Lincoln Park, N.J., USA) ($10^4$ cells/well for HL-60, MCF-7, PC-3, MDA-MB-231 and WI-38 cells, $5 \times 10^3$ cells/well for OVCAR-3, LNCaP and K-562 cells and $10^5$ cells/well for normal lymphocytes), in triplicate and in a total of 100 µl medium.

The cells were incubated at 37° C. and 5% $CO_2$. The steroid derivatives of the present disclosure were dissolved in ethanol to prepare the $1 \times 10^{-2}$ M stock solutions. The stock solutions and doxorubicin (DOX) (Novapharm, Toronto, Canada) were diluted at multiple concentrations with culture media, added to each well, as indicated, and incubated for 3 days. Following each treatment, 20 µl MTS was added to each well and the mix was incubated for 4 h. The plates were subsequently read at 490 nm using a microplate reader (Molecular Devices, Sunnyvale, Calif., USA) and the $IC_{50}$ value (50% of cell growth inhibition) was determined (Tables 3 and 4).

TABLE 3

Antiproliferative (cytotoxic) activity ($IC_{50}$ in µM) on different cancer cell lines of selected 2-(N-substituted piperazinyl) steroid derivatives of the present disclosure.[a]

| Compound ID | MCF-7 | MDA-MB-231 | Shio | LNCaP | PC-3 | OVCAR-3 | HL-60 | K-562 | WI-38 | Lymph Norm. |
|---|---|---|---|---|---|---|---|---|---|---|
| Doxorubicin | >10 | 0.9 | 1.3 | 0.1 | 0.9 | 0.9 | 0.080 | 0.4 | 3 | 0.16 |
| RM | 0.6 | >10 | 0.2 | 1.5 | 6.5 | 1.1 | 2.1 | >10 | >10 | 27.4 |
| PC-37 | 0.5 | >10 | 0.2 | 1.5 | 6.5 | 1.4 | 2.5 | 10.6 | >10 | 36 |
| PC-41 | 0.4 | >10 | 0.2 | 1.0 | 6.5 | 0.8 | 3.1 | >10 | >10 | 19.3 |
| PC-42 | 0.4 | >10 | 0.2 | 0.5 | 4 | 0.8 | 1.5 | 9.3 | >10 | 7.9 |
| PC-46 | 0.7 | >10 | 0.2 | 0.9 | 4 | 1.3 | 1.9 | 14.1 | >10 | 9.3 |
| FC-48 | 1.5 | >10 | 1.3 | 2.2 | >10 | 1.6 | 1.8 | >10 | >10 | >50 |
| TC-12 | 0.3 | >10 | 0.2 | 0.8 | 3 | 0.7 | 1.7 | 7.8 | >10 | 9.3 |

[a]Concentration of some synthesized compounds inhibiting 50% of cell growth ($IC_{50}$ in µM) of various cancer cells lines (MCF-7, MDA-MB-231, Shionogi, LNCaP, PC-3, OVCAR-3, HL-60, K-562) and normal cells (WI-38 and normal lymphocytes).

TABLE 4

Antiproliferative (cytotoxic) activity on HL-60 cancer cell line.

| Aminosteroid ID | $IC_{50}$ µM |
|---|---|
| PC-37 | 1.9 |
| 26 (AH-71) | 1.9 |
| 30 (AH-56) | 4.7 |
| 31 (AH-38) | 1.6 |

TABLE 4-continued

Antiproliferative (cytotoxic) activity on HL-60 cancer cell line.

| Aminosteroid ID | IC$_{50}$ µM |
|---|---|
| 32 (AH-47) | 4.7 |
| 33 (AH-62) | 1.4 |
| 37 (AH-55) | 4.5 |
| 38 (AH-75) | >10 |
| 39 (AH-70) | 5.0 |

Plasmatic Concentration (AUC) of Aminosteroids After a Single Subcutaneous Injection in Rat Animals: Six to seven week-old male Sprague-Dawley rats (Crl:CD®(SD)Br VAF/Plus™) weighing approximately 220 g were obtained from Charles-River, Inc (St-Constant, Qc., Canada). The animals were acclimatized to environmental conditions (temperature: 22±3° C.; humidity: 50±20%; 12-h light/12-h dark cycles, lights on at 07:15 h) for at least 5 days before starting the experiment. The animals were housed three per cage and were allowed free access to water and a certified commercial rodent food (Rodent Diet #T.2018.15, Harlan Teklad, Madison, Wis., U.S.A.) and were randomized according to their body weight. The experiments with animals were conducted in an animal facility approved by the Canadian Council on Animal Care (CCAC) and the Association for Assessment and Accreditation of Laboratory Animal Care. The study was performed in accordance with the CCAC Guide for Care and Use of Experimental Animals.

Assay: A pharmacokinetic study was carried out following one subcutaneous (s.c.) injection of the aminosteroids at one concentration (2.3 mg/kg of body weight in 0.5 mL of vehicle fluid). The compound was first dissolved in Ethanol (EtOH) followed by the addition of propylene glycol such that a final concentration of EtOH of 8% was obtained. During this experiment, the rats were housed individually and were fasted for 8h before injection of the aminosteroid. Blood samples for determination of aminosteroid plasma concentration were collected at the jugular vein (0.4 mL by animal) at target intervals of 3, 7, 12 and 24 h (or 3 and 12 h) post-dose from six rats per time point (Tables 5, 6 and 7). After the collect at 7 h, a replacement fluid (0.9% sodium chloride injection USP) was injected in the rat. Blood samples were collected in Microvette potassium-EDTA (ethylenediamine tetra-acetic acid)-coated tubes (Sarstedt, Aktiengesellchaft & Co, Germany) and centrifuged at 3200 rpm for 10 minutes at 4° C. The plasma was collected and stored at −80° C. until analyzed by liquid chromatography/mass spectrometry/mass spectrometry (LC/MS/MS) analysis.

TABLE 5

Plasmatic concentration (AUC) of aminosteroid injected subcutaneous one time (2.3 mg/kg) in rat.

| Aminosteroid ID | AUC (7 h) (ng/mL · h) | AUC(12 h) (ng/mL · h) | AUC (24 h) (ng/mL · h) |
|---|---|---|---|
| RM | 258 | 280 | 280 |
| RM (HCl) | 331 | 348 | 348 |
| PC-37 | 337 | 462 | 552 |
| PC-42 | 641 | 751 | 767 |
| PC-46 | 771 | 830 | 830 |
| FC-48 | 290 | 413 | 555 |
| LPC-37 | 372 | 525 | 681 |
| LPC-48 | 474 | 543 | 543 |

TABLE 6

Antiproliferative (cytotoxic) activity of aminosteroids on HL-60 cancer cell line and their plasmatic concentration (AUC) of aminosteroid injected subcutaneous one time (2.3 mg/kg) in rat.

| Aminosteroid ID | AUC (0-3 h) (ng/mL · h) | AUC (0-12 h) (ng/mL · h) | IC$_{50}$ (HL-60) (µM) |
|---|---|---|---|
| PC-37 | 97 | 429 | 1.9 |
| 26 (AH-71) | 278 | 1338 | 1.9 |
| 31 (AH-38) | 244 | 991 | 1.6 |
| 32 (AH-47) | 292 | 1172 | 4.7 |
| 33 (AH-62) | 185 | 752 | 1.4 |
| 30 (AH-56) | 183 | 876 | 4.7 |
| 37 (AH-55) | 50 | 234 | 4.5 |
| 38 (AH-75) | 38 | 72 | >10 |
| 39 (AH-70) | 11 | 67 | 5.0 |

Aminosteroid measurement: The concentration of the aminosteroid was determined by LC/MS/MS analysis using a procedure developed at the CHUQ (CHUL)—Research Center (Québec, Qc, Canada). Briefly, for extraction from serum, 100 vL, of the serum sample was transferred to individual tubes and 600 µL of ammonium acetate (1 mM) was added. A methanolic solution (50 µL) containing a steroidal internal standard was then added to each tube. Samples were transferred on Strata-X SPE columns (Phenomenex, Torrance, Calif., USA), which have been conditioned with 2 mL of MeOH and 2 mL of water. Each column was washed with 2 mL of MeOH:water (10:90, v/v). The aminosteroid was then eluted with 5 mL of MeOH containing 5 mM ammonium acetate. The MeOH was evaporated at 45° C. under inert atmosphere and the dried residue dissolved in 100 µL of MeOH:water (85:15, v/v). For the aminosteroid analysis, the HPLC system used a 75×4.6-mm, 3-µm reversed-phase Luna Phenyl-Hexyl column (Phenomenex, Torrance, Calif., USA) at a flow rate of 0.8 mL/min. The inhibitor was detected using an API 3000 mass spectrometer, equipped with Turbolon-Spray (Applied Biosystems, Canada). ESI in positive ion mode was used.

Efficacy of PC-37 to Reduce the Growth of Human MCF-7 Breast Cancer Xenografts in Nude Mice MCF-7 breast cancer cells were obtained from the ATCC (Rockville, Md.) and were propagated in Dubelcco's Modified Eagle's Medium nutrient mixture F-12 ham (DME-F12) medium supplemented with 5% FBS, glutamine (2 mM), penicillin (100 IU/mL), streptomycin (100 µg/mL) and estradiol (1 nM). These cells were used to induce tumors in homozygous female nu/nu Brathymic mice (28-42 days old) that were obtained from Charles River (Saint-Constant, Canada). Bilateral ovariectomy was performed under isoflurane-induced anesthesia. At the time of ovariectomy, an implant of estradiol (E2) was inserted s.c. to stimulate initial tumor growth. E2 implants were prepared in 1 cm long Silastic tubing (inside diameter 0.062 inch, outside diameter 0.095 inch) containing 5 mm of 1:8 (w/w) mixture of E2 and cholesterol. One week after ovariectomy, 4.1×10$^6$ MCF-7 cells were inoculated s.c. in 0.1 mL of medium growth+30% Matrigel on both flanks of each ovariectomized (OVX) mouse through a 2.5 cm long 22-gauge needle. After approximately 5 weeks, the mice were randomly assigned to 2 groups according to tumor size. The estradiol implant was replaced by a new one in both groups and 1500 µg of PC-37 (60 mg/kg on average) suspended in 0.2 mL of 8% ethanol in propylene glycol was injected subcutaneously 3 times a week (group 2). Animals in the control group (group 1) received 0.2 mL of the vehicle alone only. The size of tumors was measured by two perpendicular diameters and tumor area (mm$^2$) was calculated using the formula L/2×W/2×π. The area measured on the first day of treatment was taken as 100% (FIG. 1). After 28 days of treatment, the animals were weighed, anesthetized with isoflurane and killed by cervical dislocation.

Experimental

General. Unless otherwise noted, starting materials and reactants were obtained commercially and were used as such or purified by standard means. The solvents were obtained from Fisher Scientific (Montréal, Qc, Canada) and were used as received. Anhydrous tetrahydrofuran (THF) and dichloromethane ($CH_2Cl_2$) were obtained from Sigma-Aldrich (St-Louis, Mo., USA). Anhydrous acetonitrile (MeCN), toluene and $CH_2Cl_2$ were obtained by distilling from $CaH_2$ under argon whereas anhydrous THF and $Et_2O$ were obtained by distilling from sodium metal/benzophenone ketyl under argon. Thin-layer chromatography (TLC) and flash-column chromatography (FCC) were performed on 0.20-mm silica gel 60 F254 plates (Whatman Ltd, England) and with Silicycle R10030B 230-400-mesh silica gel (Québec, Qc, Canada) respectively. When required, all glassware was flame dried and allowed to cool under a stream of dry argon.

$^1$H NMR and $^{13}$C NMR, recorded at 400 MHz and 100.6 MHz respectively, were performed on a Brucker Avance 400 digital spectrometer (Billerica, Mass., USA) and reported in ppm. Proton chemical shifts were internally referenced to the residual proton resonance in $CDCl_3$ (δ 7.26 ppm), $CD_3OD$ (δ 3.31 ppm), d6-Acetone (δ 2.05 ppm), $CD_3CN$ (δ 1.94 ppm), or d6-DMSO (δ 2.50 ppm). Carbon chemical shifts were internally referenced to the deuterated solvent signals in $CDCl_3$ (δ 77.2 ppm), $CD_3OD$ (δ 49.0 ppm), d6-Acetone (δ 206.3 ppm) or d6-DMSO (δ 39.5 ppm). Low-resolution mass spectra (LRMS) were recorded on a PE Sciex API-150EX apparatus (Foster City, Calif., USA) equipped with a turbo ionspray source.

The various libraries were synthesized in parallel fashion using an automated synthesizer (model 'The solution' from aapptec, Louisville, Ky., USA) with a reaction block (Ares block) of 96 wells (4 mL per wells). The work-up following final cleavage from the solid support was assisted with a separator phase syringe (10 mL) from Biotage (Charlottesville, Va., USA).

Preparation of 5α-Androst-2-en-17-one (2)

To a solution of epiandrosterone (150 mg, 0.517 mmol) in anhydrous dichloromethane (11 mL) at −78° C. under argon atmosphere was added diethylaminosulfur trifluoride (DAST) (0.082 mL, 0.620 mmol) and the resulting solution stirred for 1 h at −78° C. The solution was then directly evaporated with silica gel and purified by FCC with EtOAc/hexanes (1:99) as eluant to give the desired compound 2 (42 mg, 30%) with a ratio of $C_2$-$C_3$ alkene vs. $C_3$-$C_4$ alkene isomer of less than 90:10. $^1$H NMR ($CDCl_3$) δ: 0.78 (s, 18-$CH_3$), 0.87 (s, 19-$CH_3$), 0.9-2.0 (residual CH and $CH_2$), 2.06 (m, 16α-CH), 2.44 (dd, $J_1$=8.8 Hz and $J_2$=19.2 Hz, 16β-CH), 5.59 (m, 2-CH and 3-CH). $^{13}$C NMR ($CDCl_3$) δ: 11.6, 13.7, 20.2, 21.7, 28.4, 30.2, 30.6, 31.5, 34.7, 35.1, 35.8, 39.7, 41.4, 47.7, 51.4, 54.1, 125.7, 125.8, 221.5. LRMS for $C_{19}H_{29}O$ [M+H]$^+$: 273.1 m/z.

Preparation of 5α-Androst-2-ene-17β-ol (3)[19,20]

To a solution of compound 2 (5.0 g, 18.3 mmol) in MeOH (300 mL) at room temperature was added $NaBH_4$ (905 mg, 23.4 mmol). The solution was stirred at room temperature for 24 h. The resulting solution was concentrated under reduced pressure, diluted with EtOAc, washed sequentially with water and brine, and finally dried over magnesium sulfate. The crude compound was purified by FCC using EtOAc/hexanes (1:9) as eluant to give title compound 3 (4.8 g, 95%). IR (film): 3252 (OH), 3017 (C=C); $^1$H NMR ($CDCl_3$) δ: 0.74 (s, 19-$CH_3$), 0.76 (s, 18-$CH_3$), 0.70-2.10 (residual CH and $CH_2$), 3.63 (t, J=8.5 Hz, 17α-CH), 5.58 (m, 2H alkene); $^{13}$C NMR ($CDCl_3$) δ: 11.05, 11.71, 20.48, 23.37, 28.60, 30.28, 30.50, 31.37, 34.70, 35,63, 36.75, 39.79, 41.51, 42.86, 51.00, 54.17, 82.01, 125.85 (2×); LRMS for $C_{19}H_{34}ON$ [M+$NH_4$]$^+$: 292.3 m/z; HRMS calcd for $C_{19}H_{30}OAg$ [M+Ag]$^{30}$: 381.13412, found 381.13421.

Preparation of (2α,3α,5α,17β)-2,3-Epoxyandrostan-17-ol (4)[19,20]

To a solution of compound 3 (1.02 g, 3.7 mmol) in dry $CH_2Cl_2$ (35 mL) at 0° C. was added portion-wise m-chloroperbenzoic acid (m-CPBA) 77% pure (1.23 g, 5.46 mmol). The mixture was stirred for 1 h at 0° C., then allowed to warm to room temperature and stirred overnight. The mixture was concentrated under reduced pressure, the residue diluted in EtOAc, the solution washed successively with a saturated aqueous solution of $Na_2S_2O_3$ (2×100 mL) and a saturated aqueous solution of $Na_2CO_3$ (2×100 mL), dried over $MgSO_4$, filtered and evaporated to dryness. Purification by flash chromatography (EtOAc:hexanes, 1:5) yielded 909 mg (85%) of title compound 4 as a white solid. IR (film): 3262 (OH); $^1$H NMR ($CDCl_3$) δ: 0.72 (s, 19-$CH_3$), 0.76 (s, 18-$CH_3$), 0.55-2.10 (residual CH and $CH_2$), 3.12 (m, 2H epoxide), 3.63 (t, J=8.5 Hz, 17α-CH); $^{13}$C NMR ($CDCl_3$) δ: 11.02, 12.95, 20.45, 23.34, 28.26, 29.00, 30.44, 31.20, 33.70, 35.67, 36.28, 36.60, 38.27, 42.78, 50.78, 51.04, 52.42, 53.79, 81.88; LRMS for $C_{19}H_{31}O_2$ [M+H]$^+$: 291.3 m/z; HRMS calcd for $C_{19}H_{30}O_2Na$ [M+Na]$^+$: 313.21380, found 313.21362.

Preparation of (2β,3α,5α,17β)-2-(Piperazin-1-yl)androstane-3,17-diol ($_5$)[19,20]

A solution of compound 4 (6.46 g, 22.3 mmol) in piperazine (50 g, 582 mmol) and water (6.3 mL) was refluxed (160° C.) for 24 h. The mixture was poured in water (500 mL) and the precipitate filtered. The solid was dissolved in $CH_2Cl_2$, the solution dried over $MgSO_4$, filtered, and evaporated to dryness. Purification by flash chromatography (MeOH:$Et_3$N:$CH_2Cl_2$, 14:1:85) yielded 5.76 g (69%) of title compound 5 as a white solid. IR (NaCl film): 3370 (OH, alcohols and NH, amine). $^1$H NMR ($CD_3OD$) δ: 0.74 (s, 18-$CH_3$), 0.99 (s, 19-$CH_3$), 0.70-2.25 (residual CH and $CH_2$), 2.33, 2.48, 2.55 and 2.82 (4m, 4×$CH_2$N and 2α-CH), 3.54 (t, J=8.6 Hz, 17α-CH), 4.05 (m, 3β-CH). $^1$H NMR ($CDCl_3$) δ: 0.71 (s, 18-$CH_3$), 0.84 (s, 19-$CH_3$), 0.65-2.15 (residual CH and $CH_2$), 2.42, 2.58 and 2.90 (3m, 4×$CH_2$N and 2α-CH), 3.62 (t, J=8.5 Hz, 17α-CH), 3.84 (m, 3β-CH). $^{13}$C NMR ($CD_3OD$) δ: 11.7, 14.6, 21.8, 24.3, 29.1, 30.6, 32.7, 34.3, 36.2, 36.6, 37.3, 38.1, 40.5, 44.2, 46.8 (2×), 52.0 (2×), 52.4, 57.0, 66.4, 66.9, 82.5; $^{13}$C NMR ($CDCl_3$) δ: 11.2, 17.3, 20.9, 23.3, 28.2, 30.5, 31.1, 32.6, 34.7, 35.5, 35.7, 36.9, 38.4, 43.0, 46.7 (2×), 49.4 (2×), 50.9, 56.2, 63.3, 65.0, 81.6; LRMS for $C_{23}H_{41}O_2N_2$ [M+H]$^+$: 377.3 m/z; HRMS calcd for $C_{23}H_{41}O_2N_2$ [M+H]$^+$: 377.31625, found 377.31596.

Preparation 9H-Fluoren-9-ylmethyl 4-[2β, 3α, 5α, 17β)-3,17-dihydroxyandrostan-2-yl]piperazine-1-carboxylate (6)[19, 20]

To a solution of compound 5 (5.76 g, 15.3 mmol) in a mixture of THF:water (5:1, 275 mL) was added successively aqueous $NaHCO_3$ 1 M (37 mL) and N-(9-fluorenylmethoxycarbonyloxy)-succinimide (Fmoc-O-Suc). The mixture was stirred for 3 h, then diluted in water and extracted with EtOAc. The organic phase was dried over $MgSO_4$, filtered, and evaporated to dryness. Purification by flash chromatography (EtOAc:hexanes, 1:1) followed by crystallization from a mixture of $CH_2Cl_2$ and hexanes yielded 6.1 g (70%) of title compound 6 as a white solid. IR (NaCl film): 3423 (OH, alcohol), 1690 (C=O, carbamate), 1448 (aromatic ring), 1243 (C—O—C, carbamate); $^1$H NMR ($CDCl_3$) δ: 0.74 (s, 18-CH$_3$), 0.87 (s, 19-CH$_3$), 0.70-2.20 (residual CH and CH$_2$), 2.4-2.9 (broad, 2×CH$_2$N and 2α-CH), 3.4-3.7 (broad, 2×CH$_2$NCO), 3.63 (t, J=8.5 Hz, 17α-CH), 3.85 (m, 3β-CH), 4.24 (t, J=6.6 Hz, CHCH$_2$ of Fmoc), 4.45 (d, J=6.3 Hz, CH$_2$O of Fmoc), 7.34 (t, J=7.4 Hz, 2H of Fmoc), 7.40 (t, J=7.4 Hz, 2H of Fmoc), 7.57 (d, J=7.4 Hz, 2H of Fmoc), 7.77 (d, J=7.5 Hz, 2H of Fmoc); $^{13}$C NMR (CDCl$_3$) δ: 11.2, 17.3, 20.9, 23.3, 28.1, 30.5, 31.1, 32.9, 34.7, 35.5, 35.8, 36.8, 38.4, 43.1, 44.1, 47.3, 48.0, 50.8, 56.1, 63.7, 64.9, 67.2, 81.8, 119.9 (2×), 124.9 (2×), 127.0 (2×), 127.7 (2×), 141.3, 143.9, 155.0; LRMS for C$_{38}$H$_{51}$O$_4$N$_2$ [M+H]$^+$: 599.3 m/z; HRMS calcd for C$_{38}$H$_{51}$O$_4$N$_2$ [M+H]$^+$: 599.38433, found 599.38400.

Preparation of 9H-Fluoren-9-ylmethyl 4-[2β,3α,5α,17β)-3,17-dihydroxyandrostan-2-yl]piperazine-1-carboxylate loaded resin (7)[19, 20]

To PS-DES resin (2.00 g, 1.58 mmol/g theoretical loading) previously dried under vacuum over a period of 2 days, charged in a 50 mL peptide flask under argon and swollen in dry CH$_2$Cl$_2$ (10 mL), was added 1,3-dichloro-5,5-dimethyl-hydantoin (1.86 g, 9.47 mmol) in dry CH$_2$Cl$_2$ (10 mL). After 1 h, the resulting chlorosilyl resin was washed under argon with dry CH$_2$Cl$_2$ (3×20 mL). The disappearance of the SiH band at 2100 cm$^{-1}$ was confirmed by the IR spectrum. The resin was next used for the loading step. Under argon, the resin was swollen in dry CH$_2$Cl$_2$ (10 mL) and a solution of imidazole (645 mg, 9.46 mmol) and hydroxysteroid 6 (5.66 g, 9.47 mmol) in CH$_2$Cl$_2$ (10 mL) was added. The solution was vortexed with a Burrell wrist-action shaker over a period of 4 h at room temperature. The resin was washed with CH$_2$Cl$_2$ (5×20 mL), MeOH (3×20 mL), and dried overnight under vacuum to give 3.24 g of resin 7 with a loading of 0.64 mmol/g. IR (KBr): 3465 (OH, alcohol), 1702 (C=O, carbamate). Any free steroid 6 (4.26 g) was easily recovered following flash chromatography with EtOAc:hexanes (1:1).

General Procedure for the Preparation of Resin-Bound Derivatives 8A-8C

To resin 7 (17.5 g, 0.52 mmol/g) was added 200 mL of a solution of piperidine in dichloromethane (20%, v/v). The suspension was vortexed using a Burrell wrist-action shaker over a period of 1 h at room temperature. The resin was then filtered and washed successively with dichloromethane (5×250 mL) and methanol (5×250 mL), and finally dried overnight to provide 14.8 g of Fmoc deprotected resin.

The resin was divided in three portions (4.90 g, 0.52 mmol/g in a 100 mL peptide flask). To each portion was added a solution of the appropriate amino acid (Fmoc-PRO—OH (3.5 g, 10.3 mmol), Fmoc-PHE-OH (4.0 g, 10.3 mmol) or Fmoc-TIC—OH (4.1 g, 10.3 mmol)), PyBOP (5.35 g, 10.3 mmol) and HOBt (1.39 g, 10.3 mmol) in DMF (60 mL) under an argon atmosphere. Diisopropylethylamine (DIPEA) (3.6 mL, 20.6 mmol) was added to the suspensions and the peptide flasks were vortexed with a Burrell wrist-action shaker over a period of 5 hr at room temperature. The resins were then filtered and washed successively with dichloromethane (5×75 mL) and methanol (5×75 mL) and finally dried overnight to give resins 8A-8C. The coupling reaction was repeated a second time in each case in order to ensure complete coupling.

General Procedure for the Preparation of Resin-Bound Derivatives 9A-9C

To each of the resins-bound derivatives 8A-8C (3×5.7 g) was added 60 mL of a solution of piperidine in dichloromethane (20%, v/v). The three suspensions were vortexed with a Burrell wrist-action shaker over a period of 1 h at room temperature. The resins were then filtered, washed successively with dichloromethane (5×75 mL) and methanol (5×75 mL) and finally dried overnight to provide Fmoc deprotected resins 9A-9C.

General Procedure for the Synthesis of an Amide Library Amide Formation

Portions of the appropriate resin-bound derivative were placed in each of the reactor wells (4 mL) of the automated synthesizer reaction block (48-well format). To each well was successively added 0.7 mL of a 0.3 M solution of the appropriate carboxylic acid in DMF, 0 7 mL of a 0.3 M solution of PyBOP and HOBt in DMF, and finally 0.7 mL of 0.6 M solution of DIPEA in DMF. The resulting suspensions were vortexed at 600 rpm over a period of 3 h under an argon atmosphere. The wells were then filtered to remove the reaction solution from the resin. The coupling reaction cycle was repeated a second time and the resulting resins were washed successively with DMF (2×3 mL), dichloromethane (2×3 mL) and methanol (2×3 mL). This procedure was repeated for each of the resin-bound derivatives 9A-9C such that a total of 144 amide compounds were prepared (3×48).

Cleavage of the Resin-Bound Derivatives.

To each of the resin-bound derivatives was added 2 mL of an acid solution of HCl (2M)/MeOH (AcCl+MeOH) in CH$_2$Cl$_2$ (20:80, v/v) and the resulting suspensions vortexed at 600 rpm over a period of 1 h. The suspensions were then filtered and the recovered filtrate neutralized with 0.5 mL of 10% aqueous NaHCO$_3$ (pH=8). The biphasic solution was then filtered using a phase separator syringe (Biotage) and the resulting organic solution evaporated under reduced pressure. Finally, the crude amide compounds were purified by filtration over a silica gel plug (10 mL) using EtOAc/hexanes (1:1) (15 mL) and then EtOAc (20 mL) to provide the amide compounds (PC1-PC48, FC1-FC48 and TC1-TC48; Table 1).

{4-[(2β,3α,5α,17β)-3,17-Dihydroxyandrostan-2-yl]piperazin-1-yl}[2S)-1(naphtalen-1-ylcarbonyl)pyrrolidin-2-yl]methanone (PC-37)

Yield: 47%; $^1$H NMR (CDCl$_3$) δ: 0.73 (s, 18-CH$_3$), 0.85 (s,19-CH$_3$), 0.65-2.20 (residual CH and CH$_2$), 2.40-2.80 (broad, 2×CH$_2$N and 2α-CH), 3.50-3.95 (broad, 2×CH$_2$NCO, CH$_2$N of proline, 17α-CH, and 3β-CH), 5.14 (dd, J$_1$=6.0 Hz, J$_2$=8.1 Hz, NCHCO of proline), 7.50 (m, 2×CH of naphthalene), 7.67 (d, J=7.2 Hz, 1×CH of naphthalene), 7.86 (m, 2×CH of naphthalene), 8.09 (s, 1×CH of naphthalene); $^{13}$C NMR (CDCl$_3$) δ: 11.2, 17.2, 20.9, 23.3, 25.6, 28.2, 29.3, 29.4, 30.5, 31.1, 33.0, 34.6, 35.5, 35.8, 36.8, 38.5, 42.7, 43.1, 46.3, 48.9, 50.3, 50.9, 56.2, 63.8, 64.9, 81.9, 124.5, 126.6, 127.1, 127.4, 127.7, 128.0, 128.6, 132.5, 133.7, 133.9, 169.5, 170.4. LRMS for C$_{39}$H$_{54}$N$_3$O$_4$ [M+H]$^+$: 628.5 m/z.

4-{[(2S)-2-({4-[(2β,3α,5α,17β)-3,17-dihydroxyandrostan-2-yl]piperazin-1-yl}carbonyl)pyrrolidin-1-yl]carbonyl}benzonitrile (PC-41)

Yield: 19%; $^1$H NMR (CDCl$_3$) δ: 0.73 (s, 18-CH$_3$), 0.85 (s,19-CH$_3$), 0.65-2.30 (residual CH and CH$_2$), 2.40-2.75 (broad, 2×CH$_2$N and 2α-CH), 3.40-3.95 (broad, 2×CH$_2$NCO, CH$_2$N of proline, 17α-CH, 3β-CH), 5.05 (dd, J$_1$=5.5 Hz, J$_2$=8.2 Hz, NCHCO of proline), 7.70 (q of AB system, 4×CH of benzonitrile); $^{13}$C NMR (CDCl$_3$) δ: 11.2, 17.1, 20.9, 23.3, 25.4, 28.2, 29.3, 30.5, 31.1, 33.0, 34.6, 35.5, 35.8, 36.8, 38.5, 42.7, 43.1, 46.2, 48.1, 48.7, 50.0, 50.9, 56.1, 56.5, 63.8, 64.9, 81.9, 113.8, 118.2, 127.9 (2×), 132.2 (2×), 140.7, 167.4, 169.7. LRMS for C$_{36}$H$_{51}$N$_4$O$_4$ [M+H]$^+$: 603.5 m/z.

(2E)-1-{(2S)-2-{4-[(2β,3α,5α,17β)-3,17-Dihydroxyandrostan-2-yl]piperazin-1-yl}carbonyl)pyrrolidin-1-yl]-3-phenylprop-2-en-1-one (PC-42)

Yield: 46%; ¹H NMR (CDCl₃) δ: 0.74 (s, 18-CH₃), 0.86 (s,19-CH₃), 0.65-2.30 (residual CH and CH₂), 2.40-2.75 (broad, 2×CH₂N and 2α-CH), 3.40-3.95 (broad, 2'CH₂NCO, CH₂N of proline, 17α-CH, 3β-CH), 5.00 (dd, $J_1$=3.6 Hz, $J_2$=8.1 Hz, NCHCO of proline), 6.77 (d, J=15.5 Hz, CH=C HCO), 7.35 (m 3×CH of phenyl), 7.52 (m, 2×CH of phenyl), 7.70(d, J=15.5 Hz, CH=CHCO); ¹³C NMR (CDCl₃) δ: 11.2, 17.2, 21.0, 23.3, 24.8, 28.2, 29.1, 29.3, 30.5, 31.1, 33.0, 34.6, 35.5, 35.8, 36.8, 38.5, 42.6, 43.1, 46.2, 47.2, 48.0, 48.8, 50.9, 56.1, 56.3, 63.8, 64.9, 81.9, 118.3, 127.9 (2×), 128.8 (2×), 129.7, 135.2, 142.6, 164.7, 170.2. LRMS for $C_{37}H_{54}N_3O_4$ [M+H]⁺: 604.5 m/z.

{4-[(2β,3α,5α,17β)-3,17-Dihydroxyandrostan-2-yl]piperazin-1-yl}[2S)-1-{[(4R)-4-(prop-1-en-2yl)cyclohex-1-en-1-yl)carbonyl)pyrrolidin-2-yl]methanone (PC-46)

Yield: 59%; ¹H NMR (CDCl₃) δ: 0.73 (s, 18-CH₃), 0.84 (s, 19-CH₃), 1.74 (s, CH₂=CH₃), 0.65-2.30 (residual CH and CH₂), 2.35-2.75 (broad, 2×CH₂N and 2α-CH), 3.40-3.90 (broad, 2×CH₂NCO, CH₂N of proline, 17α-CH, 3β-CH), 4.73 (d, J=13.8 Hz, CH₂=CH₃), 4.91 (t, J=7.3 Hz, NCHCO of proline), 6.15 (s, CH=C—CON), ¹³C NMR (CDCl₃) δ: 11.2, 17.2, 20.8, 20.9, 23.3, 25.5, 25.8, 27.0, 28.2, 29.2, 30.2, 30.5, 31.1, 33.0, 34.6, 35.5, 35.8, 36.8, 38.5, 40.10, 42.6, 43.1, 46.1, 48.0, 48.8, 49.5, 50.9, 55.6, 56.1, 63.8, 64.9, 81.9, 109.0, 129.8, 134.4, 149.1, 170.5 (2×). LRMS for $C_{38}H_{60}N_3O_4$ [M+H]⁺: 622.5 m/z.

3-acetyl-N-[(2S)-1-{4-[(2β,3α,5α,17β)-3,17-Dihydroxyandrostan-2-yl]piperazin-1-yl}1-oxo-3-phenylpropan-2-yl]benzamide (FC-48)

Yield: 62%; ¹H NMR (CDCl₃) δ: 0.74 (s, 18-CH₃), 0.82 (s, 19-CH₃), 0.65-2.75 (residual CH and CH₂), 2.25 and 2.75 (2 m, 2×CH₂N and 2α-CH), 2.65 (s, CH₃CO), 3.00-3.85 (broad m, 2×CH₂NCO, CH₂Ph, 17α-CH, 3β-CH), 5.36 (m, NH CHCO); 7.27 (m, CH₂Ph), 7.55 (t, J=7.8 Hz, CH of acetophenone), 7.97 (d, J=7.8 Hz, CH of acetophenone), 8.10 (d, J=7.8 Hz, CH of acetophenone), 8.36 (s, CH of acetophenone). ¹³C NMR (CDCl₃) δ: 11.2, 17.2, 21.0, 23.3, 26.8, 28.1, 30.5, 31.1, 32.9, 34.6, 35.5, 35.7, 36.8, 38.4, 40.0, 42.5, 43.1, 46.2, 47.4, 48.2, 50.1, 50.9, 56.2, 63.7, 64.6, 81.9, 127.0, 127.1, 128.7 (2×), 129.0, 129.7 (2×), 131.3, 131.4, 134.4, 136.0, 137.4, 165.7, 169.4, 197.3. LRMS for $C_{41}H_{56}N_3O_5$ [M+H]⁺: 670.5 m/z.

General Procedure for the Synthesis of a Sulfonamide Library

Sulfonamide Formation

Portions of the appropriate resin-bound derivative were placed in 10 reactor wells (4 mL) of the automated synthesizer reaction block (48-well format). To each well was successively added 1.0 mL of a 0.3 M solution of triethylamine and 1.0 mL of a 0.3 M solution of the appropriate sulfonyl chloride. The resulting suspensions were vortexed at 600 rpm over a period of 3 h under an argon atmosphere. The wells were then filtered to remove the reaction solution from the resin. The coupling reaction cycle was repeated a second time and the resulting resins were washed successively with dichloromethane (2×3 mL) and methanol (2×3 mL). This procedure was repeated for each of the resin-bound derivatives 9A-9C such that a total of 30 sulfonamide compounds were prepared (3×10).

Cleavage of the Resin-Bound Derivatives.

To each of the resin-bound derivatives was added 2 mL of an acid solution of HCl (2M)/MeOH (AcCl+MeOH) in CH₂Cl₂ (20:80, v/v) and the resulting suspensions vortexed at 600 rpm over a period of 1 h. The suspensions were then filtered and the recovered filtrate neutralized with 0.5 mL of 10% aqueous NaHCO₃ (pH=8). The biphasic solution was then filtered using a phase separator syringe (Biotage) and the resulting organic solution evaporated under reduced pressure. Finally, the crude sulfonamide compounds were purified by filtration over a silica gel plug (10 mL) using EtOAc/hexanes (1:1) (15 mL) and then EtOAc (20 mL) to provide the sulfonamide compounds (PS1-PS10, FS1-FS10 and TS1-TS10; Table 1).

{(2S)-1-[4-tent-butylphenyl)sulfonyl]pyrrolidin-2-yl}{4-[(2β,3α,5α,17β)-3,17-Dihydroxyandrostan-2-yl]piperazin-1-yl}methanone (PS-2)

Yield: 42%; ¹H NMR (acetone-d₆) δ: 0.73 (s, 18-CH₃), 1.04 (s, 19-CH₃), 1.36 (s, (CH₃)₃C), 0.70-2.10 (residual CH and CH₂), 2.40-2.70 (broad m, 2×CH₂N and 2α-CH), 3.38 (t, CH₂N of proline), 3.45-3.80 (broad m, 2×CH₂NCO, 17α-CH), 4.08 (broad s, 3β-CH), 4.83 (m, COCHNSO₂ of proline) 7.83 (d, J=1.9 Hz, 2×CH of phenyl), 7.85 (d, J=1.9 Hz, 2×CH of phenyl). ¹³C NMR (CDCl₃) δ: 11.2, 17.2, 21.0, 24.9, 28.2, 30.5, 30.7, 31.1 (3×), 31.2, 32.9, 34.6, 35.1, 35.5, 35.8, 36.8, 38.4, 42.7, 43.1, 46.2, 47.4, 48.1, 48.3, 48.5, 50.9, 56.1, 57.8, 63.8, 64.9, 81.9, 125.9 (2×), 127.4 (2×) 135.8, 156.4, 169.8. LRMS for $C_{38}H_{60}N_3O_5S$ [M+H]⁺: 670.5 m/z.

General Procedure for the Synthesis of a Benzylamine Library

Benzylamine Formation

Portions of the appropriate resin-bound derivative were placed in 6 reactor wells (4 mL) of the automated synthesizer reaction block (48-well format). To each well was successively added 1.0 mL of a 0.3 M solution of triethylamine and 1.0 mL of a 0.3 M solution of the appropriate benzyl bromide. The resulting suspensions were vortexed at 600 rpm over a period of 3 h under an argon atmosphere. The wells were then filtered to remove the reaction solution from the resin and the resulting resins were washed successively with dichloromethane (2×3 mL) and methanol (2×3 mL). This procedure was repeated for each of the resin-bound derivatives 9A-9C such that a total of 18 benzylamine compounds were prepared (3×6).

Cleavage of the Resin-Bound Derivatives.

To each of the resin-bound derivatives was added 2 mL of an acid solution of HCl (2M)/MeOH (AcCl+MeOH) in CH₂Cl₂ (20:80, v/v) and the resulting suspensions vortexed at 600 rpm over a period of 1 h. The suspensions were then filtered and the recovered filtrate neutralized with 0.5 mL of 10% aqueous NaHCO₃ (pH=8). The biphasic solution was then filtered using a phase separator syringe (Biotage) and the resulting organic solution evaporated under reduced pressure. Finally, the crude benzylamine compounds were purified by filtration over a silica gel plug (10 mL) using EtOAc/hexanes (1:1) (15 mL) and then EtOAc (20 mL) to provide the benzylamine compounds (PB1-PB6, FB1-FB6 and TB1-TB6; Table 1).

{(2S)-1-[3,5-bis(trifluoromethyl)benzyl]pyrrolidin-2-yl}{4-[(2β,3α,5α,17β)-3,17-dihydroxyandrostan-2-yl]piperazin-1-yl}methanone (PB-3)

Yield: 70%; ¹H NMR (acetone-d₆) δ: 0.72 (s, 18-CH₃), 1.01 (s, 19-CH₃), 0.65-2.25 (residual CH and CH₂), 2.35-3.05 (broad m, 2'CH₂N, CH₂N of proline and 2α-CH), 3.4-4.1 (broad m, 2×CH₂NCO, 1 CH of NCH₂Ph, 17α-CH), 4.05 (broad s, 3β-CH), 4.08 (d, J=14.0 Hz, 1×CH of NCH₂Ph), 7.90 (s, CH of phenyl), 8.08 (s, 2×CH of phenyl). ¹³C NMR (CDCl₃) δ: 11.2, 17.1, 20.9, 22.8, 23.3, 28.2, 28.8, 30.5, 31.1, 32.7, 34.6, 35.5, 35.8, 36.7, 38.4, 42.3, 43.1, 45.6, 48.0, 49.0, 50.9, 52.8, 56.1, 57.2, 63.8, 64.5, 64.8, 81.9, 121.1, 122.0, 124.7, 129.0 (2×), 131.5 (q, J=33.3 Hz, 2×CF3), 141.7, 171.0. LRMS for $C_{37}H_{52}F_6N_3O_3$ [M+H]⁺: 700.3 m/z.

General Procedure for the Synthesis of a Urea Library
Urea Formation

Portions of the appropriate resin-bound derivative were placed in 11 reactor wells (4 mL) of the automated synthesizer reaction block (48-well format). To each well was successively added 1.0 mL of a 0.3 M solution of triethylamine and 1.0 mL of a 0.3 M solution of the appropriate isocyanate. The resulting suspensions were vortexed at 600 rpm over a period of 3 h under an argon atmosphere. The wells were then filtered to remove the reaction solution from the resin. The coupling reaction cycle was repeated a second time and the resulting resins were washed successively with dichloromethane (2×3 mL) and methanol (2×3 mL) This procedure was repeated for each of the resin-bound derivatives 9A-9C such that a total of 33 urea compounds were prepared (3×11).

Cleavage of the Resin-Bound Derivatives.

To each of the resin-bound derivatives was added 2 mL of an acid solution of HCl (2M)/MeOH (AcCl+MeOH) in $CH_2Cl_2$ (20:80, v/v) and the resulting suspensions vortexed at 600 rpm over a period of 1 h. The suspensions were then filtered and the recovered filtrate neutralized with 0.5 mL of 10% aqueous $NaHCO_3$ (pH=8). The biphasic solution was then filtered using a phase separator syringe (Biotage) and the resulting organic solution evaporated under reduced pressure. Finally, the crude urea compounds were purified by filtration over a silica gel plug (10 mL) using EtOAc/hexanes (1:1) (15 mL) and then EtOAc (20 mL) to provide the urea compounds (PI1-PI11, FI1-FI11 and TI1-TI11; Table 1).

(2S)—N-(cyclohexylmethyl)-2-({4-[(2β,3α,5α,17β)-3, 17-Dihydroxyandrostan-2-yl]piperazin-1-yl}carbonyl)pyrrolidine-1-carboxamide (P1-5)

Yield: 52%; $^1H$ NMR ($CDCl_3$) δ: 0.73 (s, 18-$CH_3$), 0.84 (s, 19-$CH_3$), 0.65-2.25 (residual CH and $CH_2$), 2.35-2.75 (broad m, 2×$CH_2$N and 2α-CH), 2.90-3.75 (broad m, 2×$CH_2$NCO, $CH_2$N of proline, $HNCH_2$, 17α-CH), 3.86 (m, 3β-CH), 4.35 (t, J=5.7 Hz), 4.85 ($\overline{dd, J_1}$=2.9 Hz, $J_2$=8.0 Hz, CHNCO of proline); $^{13}C$ NMR ($CDCl_3$) δ: 11.2, 17.2, 20.9, 23.3, 24.6, 25.9, 26.5, 28.2, 29.5, 30.5, 30.8, 31.1, 32.9, 34.6, 35.5, 35.8, 36.8, 38.3, 38.5, 42.5, 43.1, 45.8, 45.9, 46.9, 48.2, 48.5, 50.9, 56.1, 56.4, 63.7, 64.9, 81.9, 156.6, 171.3. LRMS for $C_{36}H_{61}N_4O_4$ $[M+H]^+$: 613.5 m/z.

Preparation of 5α-Pregn-2-en-20-one (11)

To a solution of 5α-pregnan-3β-ol-20-one (3.75 g, 11.8 mmol) in anhydrous dichloromethane (200 mL) at −78° C. under argon atmosphere was added diethylaminosulfur trifluoride (DAST) (2.30 mL, 17.7 mmol) and the resulting solution stirred over a period of 1 h at −78° C. The solution was then directly evaporated with silica gel and purified by FCC with EtOAc/hexanes (2:98) as eluant to give the desired compound 11 (880 mg, 25%) with a ratio of $C_2$-$C_3$ alkene vs. $C_3$-$C_4$ alkene isomer of 96:4. $^1H$ NMR (acetone-$d_6$) δ: 0.60 (s, 18-$CH_3$), 0.78 (s, 19-$CH_3$), 0.75-2.40 (residual CH and $CH_2$), 2.07 (s, 21-$CH_3$), 2.60 (t, J=9.1 Hz, 17α-CH), 5.57 (m, 2-CH and 3-CH). $^{13}C$ NMR ($CDCl_3$) δ: 11.7, 13.4, 20.9, 22.7, 24.4, 28.6, 30.2, 31.6, 31.7, 34.6, 35.6, 39.1, 39.7, 41.4, 44.2, 53.9, 56.7, 63.9, 125.8, 125.9, 209.8. LRMS for $C_{21}H_{32}O$ $[M+H]^+$: 301.1 m/z.

Preparation of (5α)-Pregn-2-en-20-ol (12)

To a solution of 5-α-pregn-2-en-20-one (11) (860 mg, 2.86 mmol) in anhydrous dichloromethane (120 mL) at −78° C. under an argon atmosphere was slowly added DIBAL-H (1.0 M in hexane) (5.72 mL, 5.72 mmol). The solution was stirred at −78° C. over a period of 3 h and successively washed with an aqueous HCl solution (5%) and a Rochelle salt solution. The organic phase was then filtered using a phase separator syringe (Biotage) and evaporated. Purification by FCC (EtOAc/hexanes, 5:95) yielded 672 mg (78%) of title compound 12 as a white solid. $^1H$ NMR ($CDCl_3$) δ: 0.76 (s, 18-$CH_3$ and 19-$CH_3$), 1.13 (d, J=6.1 Hz, 21-$CH_3$), 0.70-2.10 (residual CH and $CH_2$), 3.73 (m, 20-CH), 5.58 (m, 2-CH and 3-CH). $^{13}C$ NMR ($CDCl_3$) δ; 11.7, 12.5, 20.8, 23.6, 24.4, 25.6, 28.7, 30.3, 31.9, 34.6, 35.4, 39.8, 40.1, 41.4, 42.4, 54.0, 55.9, 58.6, 70.6, 125.8, 126.0. LRMS for $C_{21}H_{33}$ [MH—$H_2O]^+$: 285.2 m/z.

Preparation of (2α-3α,5α)-2,3-Epoxypregnan-20-ol (13)

To a solution of 5-α-pregn-2-en-20-ol (12) (660 mg, 2.18 mmol) in anhydrous dichloromethane (20 mL) at 0° C. under an atmosphere of argon was added in six portions m-CPBA (733 mg, 3.27 mmol). The solution was stirred over a period of 1 h at 0° C. and then allowed to return to room temperature overnight. The resulting solution was diluted with dichloromethane (30 mL) and successively washed with a $Na_2S_2O_3$ aqueous solution (10%) and a $Na_2CO_3$ aqueous solution (10%), dried with $MgSO_4$, filtered and evaporated to dryness. Purification by FCC (EtOAc/hexanes, 5:95) yielded 511 mg (73%) of title compound 13 as a white solid. $^1H$ NMR (acetone-$d_6$) δ: 0.74 (s, 18-$CH_3$), 0.79 (s, 19-$CH_3$), 1.07 (d, J=6.1 Hz, 21-$CH_3$), 0.60-2.30 (residual CH and $CH_2$), 3.06 (m, 2×CH of epoxide), 3.62 (m, 20-CH); $^{13}C$ NMR ($CDCl_3$) δ: 12.4, 12.9, 20.7, 23.6, 24.4, 25.6, 28.4, 29.0, 31.7, 33.6, 35.4, 36.2, 38.2, 39.9, 42.3, 51.1, 52.4, 53.7, 55.7, 58.5, 70.6, LRMS for $C_{21}H_{34}O_2$ $[M+H]^+$: 319.1 m/z.

Preparation of (β,3α,5α)-2-(piperazin-1-yl)Pregnane-3, 20-diol (14)

To 2α-3α-epoxy-5α-pregnan-20-ol (13) (500 mg, 1.57 mmol) were added piperazine (3.5 g, 40.6 mmol) and water (1 mL). The suspension was heated overnight at 150° C. The resulting solution was cooled to room temperature, diluted with dichloromethane (50 mL) and washed three times with water (100 mL). The organic layer was dried using a phase separator syringe (Biotage). Purification by FCC ($CH_2Cl_2$/MeOH/triethylamine, 94:4:1) yielded 529 mg (83%) of title compound 14. $^1H$ NMR (acetone $d_6$) δ: 0.75 (s, 18-$CH_3$), 0.99 (s, 19-$CH_3$), 1.07 (d, J=6.1 Hz, 21-$CH_3$), 0.70-2.25 (residual CH and $CH_2$), 2.35, 2.50 and 2.77 (3 m, 4×$CH_2$N and 2α-CH), 3.62 (m, 20-CH), 4.01 (m, 3(3-H); $^{13}C$ NMR ($CDCl_3$) δ: 12.8, 14.7, 22.0, 23.8, 25.5, 26.8, 29.2, 33.3, 34.3, 36.4, 37.2, 40.5, 41.1, 43.8, 46.7 (2×), 51.8 (2×), 57.0, 57.5, 59.4, 66.4, 66.9, 70.9.LRMS for $C_{25}H_{44}N_2O_2$ $[M+H]^+$: 405.4 m/z.

Preparation of 9H-Fluoren-9-ylmethyl 4-[(2β,3α,5α)-3, 20-dihydroxypregnan-2-yl]piperazine-1-carboxylate (15)

To a solution of 2β-piperazino-5α-pregnane-3α, 20-diol (14) (520 mg, 1.27 mmol) in THF (12 mL) was added water (3 mL), $NaHCO_3$ (322 mg, 3.83 mmol) and Fmoc-O-succinimide (518 mg, 1.53 mmol). The solution was stirred overnight at room temperature. The resulting solution was diluted with EtOAc (50 mL), washed two times with water (70 mL), once with brine (30 mL), dried with $MgSO_4$, filtered and evaporated to dryness. Purification by FCC ($CH_2Cl_2$/MeOH, 98:2) yielded 530 mg (65%) of title compound 15. $^1H$ NMR (acetone-$d_6$) δ: 0.76 (s, 18-$CH_3$), 1.01 (s,19-$CH_3$), 1.07 (d, J=6.1 Hz, 21-$CH_3$), 0.7-2.6 (residual CH and $CH_2$), 2.21 (m, CH), 2.40 and 2.52 (2m, 2×$CH_2$N and 2α-CH), 3.41 (broad, s, 2×$CH_2$NCO), 3.65 (m, 20-CH), 4.04 (m, 3(3β-CH), 4.28 (t, J=6.5 Hz, CH of Fmoc), 4.42 (d, J=6.6 Hz, $CH_2$O of Fmoc), 7.34 (t, J=7.4 Hz, 2×CH of Fmoc), 7.42 (t, J=7.4 Hz, 2×CH of Fmoc), 7.67 (d, J=7.3 Hz, 2×CH of Fmoc), 7.87 (d, J=7.5 Hz, 2×CH of Fmoc). $^{13}C$ NMR ($CDCl_3$) δ: 12.6, 17.3, 21.2, 23.6, 24.4, 25.6, 28.3, 31.6, 32.8, 34.7, 35.4, 38.4, 40.1, 42.6, 47.4, 48.0, 55.8, 56.0, 58.5, 63.7, 64.9, 67.2, 120.0 (2×), 125.0 (2×), 127.0 (2×), 127.7 (2×), 141.3, (2×), 144.0 (2×), 155.1. LRMS for $C_{40}H_{54}N_2O_4$ $[M+H]^+$: 627.4 m/z.

Preparation of 9H-Fluoren-9-ylmethyl 4-[(2β,3α,5α)-3,20-dihydroxypregan-2-yl]piperazine-1-carboxylate loaded resin 16

1,3-Dichloro-5,5-dimethylhydantoin (5.85 g, 29.7 mmol) in dry $CH_2Cl_2$ (60 mL) was added to PS-DES resin (5.44 g, 1.56 mmol/g theorical loading) that had been previously dried under vacuum over a period of 2 days, the mixture placed into a 100 mL peptide flask under argon, and the resin allowed to swell in dry $CH_2Cl_2$ (25 mL). After a period of 1 h, the resulting chlorosilyl resin was washed under argon with dry $CH_2Cl_2$ (3×75 mL). The disappearance of the Si—H band at 2100 $cm^{-1}$ was confirmed by the IR spectrum. The resin was next used for the loading step.

The chlorosilyl resin was swollen in dry $CH_2Cl_2$ (20 mL) while under an argon atmosphere. A solution of imidazole (1.16 g, 17.0 mmol) and diol 15 (10.7 g, 16.8 mmol) in $CH_2Cl_2$ (20 mL) was subsequently added. The mixture was vortexed overnight at room temperature using a Burrell wrist-action shaker. The loaded resin was washed with $CH_2Cl_2$ (3×75 mL) and dried overnight under vacuum to provide 7.3 g of resin 16 with a loading of 0.40 mmol/g. IR (KBr): ν 3442 (OH, alcohol), 1702 (C=O, carbamate) $cm^{-1}$. The free diol 15 (8.7 g) was easily recovered after flash chromatography using EtOAc/hexanes (1:1).

General Procedure for the Preparation of Resin-Bound Derivatives 17A-17D

To resin 16 (7.3 g, 0.4 mmol/g) was added 70 mL of a solution of piperidine in dichloromethane (20% v/v). The suspension was vortexed using a Burrell wrist-action shaker over a period of 1 h at room temperature. The resin was then filtered and washed successively with dichloromethane (5×75 mL) and methanol (5×75 mL), and finally dried overnight to provide 6.5 g of Fmoc deprotected resin. The resin was divided into four portions (1.80 g, 0.40 mmol/g in a 50 mL peptide flask). To each portion was added a solution of the appropriate amino acid (Fmoc-L-PRO—OH (2.5 g, 7.5 mmol) or Fmoc-D-PRO—OH (2.5 g, 7.5 mmol); Fmoc-L-PHE-OH (2.9 g, 7.5 mmol) or Fmoc-D-PHE-OH (2.9 g, 7.5 mmol)), PyBOP (3.9 g, 7.5 mmol) and HOBt (1.0 g, 7.5 mmol) in DMF (25 mL) under an argon atmosphere. Diisopropylethylamine (DIPEA) (2.6 mL, 15.0 mmol) was added to the suspensions and the peptide flasks were vortexed with a Burrell wrist-action shaker over a period of 5 hr at room temperature. The resins were then filtered and washed successively with dichloromethane (5×25 mL) and methanol (5×25 mL) and finally dried overnight to give the title resins 17A-17D. The coupling reaction was repeated a second time in each case in order to ensure complete coupling.

General Procedure for the Preparation of Resin-Bound Derivatives 18A-18D

To each of the resins-bound derivatives 17A-17D (4×2.5 g) was added 30 mL of a solution of piperidine in dichloromethane (20%, v/v). The four suspensions were vortexed with a Burrell wrist-action shaker over a period of 1 h at room temperature. The resins were then filtered, washed successively with dichloromethane (5×30 mL) and methanol (5×30 mL) and finally dried overnight to provide Fmoc deprotected resins 18A-18D.

General Procedure for the Synthesis of an Amide Library Amide Formation

Portions (100 mg) of the appropriate resin-bound derivative were placed in 7 reactor wells (4 mL) of the automated synthesizer reaction block (48-well format). To each well was successively added 0.7 mL of a 0.3 M solution of the appropriate carboxylic acid in DMF, 0.7 mL of a 0.3 M solution of PyBOP and HOBt in DMF, and finally 0.7 mL of 0.6 M solution of DIPEA in DMF. The resulting suspensions were vortexed at 600 rpm over a period of 3 h under an argon atmosphere. The wells were then filtered to remove the reaction solution from the resin. The resins were subsequently washed successively with DMF (2×3 mL), dichloromethane (2×3 mL) and methanol (2×3 mL). This procedure was repeated for each of the resin-bound derivatives 18A-18D such that a total of 28 amide compounds were prepared (4×7).

Cleavage of the Resin-Bound Derivatives.

To each of the resin-bound derivatives was added 2 mL of an acid solution of HCl (2M)/MeOH (AcCl+MeOH) in $CH_2Cl_2$ (20:80, v/v) and the resulting suspensions vortexed at 600 rpm over a period of 1 h. The suspensions were then filtered and the recovered filtrate neutralized with 0.5 mL of 10% aqueous $NaHCO_3$ (pH=8). The biphasic solution was then filtered using a phase separator syringe (Biotage) and the resulting organic solution evaporated under reduced pressure. Finally, the crude amide compounds were purified by filtration over a silica gel plug (10 mL) using EtOAc/hexanes (1:1) (15 mL) and then EtOAc (20 mL) to provide the amide compounds illustrated in Table 2.

{4-[(2β,3α,5α,17β)-3,17-Dihydroxypregnan-2-yl]piperazin-1-yl}[2S)-1-(naphtalen-1-ylcarbonyl)pyrrolidin-2-yl]methanone (LPC-37)

Yield: 36%; $^1H$ NMR ($CDCl_3$) δ: 0.73 (s, 18-$CH_3$), 0.84 (s, 19-$CH_3$), 1.12 (d, J=6.1 Hz, 20-CH), 0.65-2.30 (residual CH and $CH_2$), 2.40-2.80 (broad m, 2×$CH_2$N and 2α-CH), 3.40-3.95 (broad m, 2×$CH_2$NCO, $CH_2$N of proline, 17α-CH, 3β-CH), 5.14 (m, NCHCO of proline), 7.53 (m, 2×CH of naphthalene), 7.67 (dd, $J_1$=1.3 Hz, J2=8.3 Hz), 1×CH of naphthalene), 7.86 (m, 2×CH of naphthalene), 8.10 (s, 1×CH of naphthalene); $^{13}C$ NMR ($CDCl_3$): δ 12.2, 17.2, 21.2, 23.6, 24.4, 25.6, 28.3, 29.4, 29.7, 31.6, 32.9, 34.6, 35.3, 35.8, 38.4, 40.1, 42.6, 46.3, 48.2, 48.8, 50.3, 55.8, 56.0, 56.2, 58.5, 63.8, 64.9, 70.6, 124.5, 126.5, 127.1, 127.4, 127.7, 128.0, 128.6, 132.5, 133.7, 133.9, 169.5, 170.4. LRMS for $C_{41}H_{58}N_3O_4$ [M+H]$^+$: 656.4 m/z.

General Procedure for the Preparation of 2β-piperazino-androstane and 2β-piperazino-pregnane derivatives by solution phase synthesis tert-Butyl-1(naphthalene-1-ylcarbonyl)-L-Prolinate (19)

To a solution of H-L-Pro-OtBu (HC1) salt (1.00 g, 4.8 mmol) in anhydrous dichloromethane (35 mL) at room temperature under an atmosphere of argon were added triethylamine (2.0 mL, 14.4 mmol) and 2-naphthoyl chloride (1.12 g, 5.9 mmol). The solution was stirred at room temperature over a period of 4 h. The resulting solution was evaporated with silica gel and then purified by FCC (EtOAc/hexanes, 7:3) to give 1.51 g (96%) of title compound 19. $^1H$ NMR (acetone-$d_6$) δ: 1.18 and 1.49 (2s, ($CH_3$)$_3$C, two rotomers), 2.00 and 2.35 (2m, 3H and 1H, 2×$CH_2$ of proline), 3.68 (m, $CH_2$N of proline), 4.48 (m, NCHCO of proline), 7.59 (m, 2×CH of naphthalene), 7.66 (d, J=8.4 Hz, 1×CH of naphthalene), 7.97 (m, 2×CH of naphthalene), 8.12 (s, 1×CH of naphthalene). LRMS for $C_{20}H_{24}NO_3$ [M+H]$^+$: 325.9 m/z.

1-(Naphthalene-1-ylcarbonyl)-L-Proline (20)

To compound 19 (550 mg, 1.7 mmol) was added a solution of TFA in dichloromethane (95:5, v/v) (4.0 mL). The solution was stirred over a period of 4 h at room temperature under an argon atmosphere. The resulting solution was evaporated under reduced pressure and purified by FCC ($CH_2Cl_2$/MeOH, 95:5) to give 415 mg (89%) of title compound 20. $^1H$ NMR (acetone-$d_6$) δ: 2.00 and 2.35 (2m, 3.2 H and 0.8 H, 2×$CH_2$ of proline), 3.66 and 3.74 (2m, 1.6H and 0.4H, $CH_2$N of proline), 4.60 and 4.67 (m, 0.2H and 0.8H, NCHCO of proline), 7.57 (broad, m, 2×CH of naphthalene), 7.67 (d, J=8.4 Hz, 1×CH of naphthalene), 7.95 (broad, m, 2×CH of naphthalene), 8.14 (s, 1×CH of naphthalene). LRMS for $C_{16}H_{16}NO_3$ [M+H]$^+$: 270.0 m/z.

{4-[(2β,3α,5α,17β)-3,17-Dihydroxyandrostan-2-yl]piperazin-1-yl}[2S)-1(naphtalen-1-ylcarbonyl)pyrrolidin-2-yl]methanone (PC-37)

To a solution of compound 5 (528 mg, 1.4 mmol) in anhydrous DMF (17 mL) at room temperature under an atmosphere of argon were added carboxylic acid 20 (415 mg, 1.6 mmol), PyBOP (827 mg, 1.6 mmol), HOBt (208 mg, 1.6 mmol), and DIPEA (540 μL, 3.1 mmol). The solution was stirred overnight at room temperature. The resulting solution was poured into water and extracted two times with EtOAc (2×30 mL), washed with brine, dried with MgSO$_4$ and evaporated to dryness. Purification by FCC (CH$_2$Cl$_2$/MeOH, 95:5) yielded 917 mg (95%) of title compound 21a (PC-37). $^1$H NMR, $^{13}$C NMR and MS data are the same as previously reported for PC-37 as prepared by solid-phase synthesis.

Preparation of (2α,3α)-2,3-epoxyandrostan-17-one (22)

To a solution of compound 2 (320 mg, 1.17 mmol) in anhydrous dichloromethane (25 mL) was added m-CPBA (316 mg, 1.41 mmol) at 0° C. under an atmosphere of argon. The solution was stirred at 0° C. for 3 h. The solution was then diluted with dichloromethane (50 mL) and washed with an aqueous sodium bicarbonate solution (10%). The organic layer was dried with sodium sulfate and evaporated under reduced pressure. The crude compound was purified by flash chromatography (Hexanes/EtOAc: 8:2) to yield compound 22 (260 mg, 78%). $^1$H NMR (CDCl$_3$) δ: 0.79 (s, 18-CH$_3$), 0.85 (s, 19-CH$_3$), 0.60-2.11 (residual CH and CH$_2$), 2.43 (dd, J$_1$=18.8 Hz, J$_2$=8.7 Hz, 16β-H), 3.12 (t, J=5.8 Hz, 2×CH of epoxide), 3.16 (broad, s, 2×CH of epoxide).

Preparation of (2β,3α)-3-hydroxy-2-(piperazin-1-yl)androstan-17-one (23)

To compound 22 (202 mg, 0.70 mmol) was added water (1 mL) and piperazine (3.5 g, 41 mmol). The solution was subsequently heated at 150° C. over a period of 24 h. The resulting mixture was diluted with dichloromethane (50 mL) and washed with water, dried with Na$_2$SO$_4$, filtered and evaporated under reduced pressure. The crude compound was purified by flash chromatography (DCM/MeOH: 9:1 containing 0.5% of TEA) to yield compound 23 (169 mg, 65%). $^1$H NMR (CDCl$_3$) δ: 0.87 (s, 18-CH$_3$ and 19-CH$_3$), 0.73-2.17 (residual CH and CH$_2$), 2.45, 2.64 and 2.91 (3m, 4×CH$_2$N and 2α-CH), 3.85 (m, 3β-CH).

Preparation of (2β,3α)-3-hydroxy-2-(4-{[(2S)-14naphthalen-2-ylcarbonyl)pyrrolidin-2-yl]carbonyl}piperazin-1-yl)androstan-17-one (24)

To a solution of compound 23 (150 mg, 0.40 mmol) in anhydrous DMF (7 mL) at room temperature under an atmosphere of argon were added carboxylic acid 20 (119 mg, 0.44 mmol), PyBOP (229 mg, 0.44 mmol), HOBt (60 mg, 0.44 mmol), and DIPEA (220 μL, 1.26 mmol). The solution was subsequently stirred overnight at room temperature. The resulting solution was then poured into water and extracted with EtOAc (2×30 mL), washed with brine, dried with MgSO$_4$ and evaporated to dryness. Purification by flash chromatography (Hexanes/Acetone: 1:1) yielded 157 mg (63%) of compound 24. $^1$H NMR (CDCl$_3$) δ: 0.89 (s, 18-CH$_3$ and 19-CH$_3$), 0.70-2.50 (residual CH and CH$_2$), 3.45-3.90 (broad, NCH$_2$ of proline and 2×CH$_2$NCO), 3.95 (m, 3β-CH), 5.09 (broad, NCHCO of proline), 7.55 (m, 2×CH of naphthalene), 7.61 (m, CH of naphthalene), 7.87 (m, 3×CH of naphthalene), 8.06 (s, CH of naphthalene).

Preparation of {4-[(2β,3α,5α,17α)-3,17-dihydroxy-21-(trimethylsilyl)pregn-20-yn-2-yl]piperazin-1-yl}[(2S)-1-(naphthalen-2-ylcarbonyl)pyrrolidin-2-yl]methanone (25)

To a solution of trimethylacetylene (0.125 mL, 0.8 mmol) in anhydrous ethyl ether (10 mL) at 0° C. under an atmosphere of argon was added dropwise MeLi (0.5 mL, 0.64 mmol). The solution was allowed to return to room temperature and stirred over a period of 1 h. The solution was subsequently cooled to 0° C. and compound 24 (113 mg, 0.16 mmol) in anhydrous THF (20 mL) was slowly added. The resulting solution was stirred for an additional 4 h at room temperature. The solution was then diluted with ethyl acetate (100 mL) and washed with a saturated ammonium chloride aqueous solution (3×50 mL). The organic layer was dried over Na$_2$SO$_4$, filtered and evaporated under reduced pressure. The crude compound was purified by flash chromatography (DCM/MeOH: 95:5) to yield compound 25 (58 mg, 44%). $^1$H NMR (CDCl$_3$) δ: 0.17 (m, (CH$_3$)$_3$Si), 0.78 and 0.82 (2s, 19-CH$_3$), 0.88 (s, 18-CH$_3$), 0.65-2.30 (residual CH and CH$_2$), 2.3-3.1 (broad m, 2×NCH$_2$ and 2α-CH), 3.45-4.08 (broad m, NCH$_2$ of proline, 2×CH$_2$NCO and 3β-CH), 5.08 (broad, NCHCO of proline), 7.54 (m, 2×CH of naphthalene) 7.65 (d, J=8.6 Hz, CH of naphthalene,), 7.87 (m, 3×CH of naphthalene) 8.08 (s, CH of naphthalene).

Preparation of {4-[(2β,3α,5α,17α)-3,17-dihydroxypregn-20-yn-2-yl]piperazin-1-yl}[(2S)-1-(naphthalen-2-ylcarbonyl)pyrrolidin-2-yl]methanone (26)

Compound 25 (46 mg, 0.06 mmol) was dissolved in methanol (9 mL) and K$_2$CO$_3$ (900 mg) was added. The solution was then vigorously stirred over a period of 3 h. The solution was subsequently filtered, diluted with ethyl acetate (50 mL) and neutralized with an aqueous ammonium chloride solution to pH 7. The organic layer was washed with brine, dried with Na$_2$SO$_4$ and evaporated under reduced pressure. The crude compound was purified by flash chromatography using DCM/MeOH (5:95) as eluant to yield compound 26 (24 mg, 58%). $^1$H NMR (CDCl$_3$) δ: 0.82 (s, 18-CH$_3$) 0.84 (s, 19-CH$_3$) 0.70-2.20 (residual CH and CH$_2$), 2.40-2.80 (broad m, 2×CH$_2$N and 2α-CH), 2.55 (s, CH of ethynyl), 3.50-3.95 (broad m, 2×CH$_2$NCO, CH$_2$N of proline, 3β-CH), 5.13 (dd, J$_1$=6.1 Hz J$_2$=8.1 Hz, NCHCO of proline), 7.52 (m, 2×CH of naphthalene), 7.67 (d, J=7.1 Hz, 1×CH of naphthalene), 7.85 (m, 3×CH of naphthalene), 8.09 (s, 1×CH of naphthalene); $^{13}$C NMR (CDCl$_3$): 12.8, 17.2, 21.0 23.0 25.6 28.1 29.4 31.1 32.7 32.9 34.6 35.8 36.1, 38.4, 38.9, 42.7, 46.2, 47.0, 47.9, 48.0, 48.9, 50.3, 55.6, 56.2, 63.8, 64.9, 73.8, 79.8, 87.6, 124.5, 126.6, 127.1, 127.4, 127.8, 128.0, 128.6, 132.5, 133.6, 133.9, 169.5, 170.4; HRMS: calcd for $C_{41}H_{54}N_3O_4$ [M+H]$^+$ 652.4109, found 652.4115.

Preparation of (17β)-17-methylandrost-2-en-17-ol (27)

To a solution of compound 2 (300 mg, 1.10 mmol) in anhydrous THF (15 mL) under an atmosphere of argon at 0° C. was added methyl magnesium bromide (1.4 M in THF; 945 μL, 1.32 mmol). The solution was allowed to return to room temperature and was subsequently stirred overnight. The solution was then diluted with ethyl acetate and poured into water. The organic layer was washed with brine, dried over Na$_2$SO$_4$, filtered and evaporated under reduced pressure. The crude compound was purified by high performance flash chromatography (Biotage) using Hexanes/EtOAc (95:5) as eluant to yield compound 27 (123 mg, 39%). $^1$H NMR (CDCl$_3$) δ: 0.78 (s, 18-CH$_3$), 0.86 (s, 19-CH$_3$), 1.21 (s, 17α-CH$_3$), 0.65-2.05 (residual CH and CH$_2$), 5.59 (m, 2×CH of alkene).

Preparation of (2α,3α,17β)-17-methyl-2,3-epoxyandrostan-17-ol (28)

To a solution of compound 27 (120 mg, 0.43 mmol) in anhydrous dichloromethane (10 mL) was added m-CPBA (112 mg, 0.54 mmol) at 0° C. under an atmosphere of argon. The solution was stirred at 0° C. over a period of 3 h. The solution was subsequently diluted with dichloromethane (50 mL) and washed with an aqueous sodium bicarbonate solution (10%). The organic layer was dried with sodium sulfate and evaporated under reduced pressure. The crude compound was purified by flash chromatography (Hexanes/acetone: 95:5) to yield compound 28 (116 mg, 91%). $^1$H NMR (CDCl$_3$) δ: 0.77 (s, 19-CH$_3$), 0.83 (s, 18-CH$_3$), 1.21 (s, 17α-CH$_3$), 0.60-1.95 (residual CH and CH$_2$), 3.11 (t, J=5.8 Hz, CH of epoxide) and 3.15 (broad s, 2×CH of epoxide).

Preparation of (2β,3α,17β)-17-methyl-2-(piperazin-1-yl)androstane-3,17-diol (29)

To compound 28 (103 mg, 0.34 mmol) was added water (1 mL) and piperazine (3.5 g, 41 mmol). The solution was subsequently heated at 150° C. over a period of 24 h. The resulting mixture was diluted with dichloromethane (50 mL) and washed with water, dried with Na$_2$SO$_4$, filtered and evaporated under reduced pressure. The crude compound was purified by flash chromatography (DCM/MeOH: 9:1 containing 1.0% of TEA) to yield compound 29 (80 mg, 60%). $^1$H NMR (CDCl$_3$) δ: 0.85 and 0.86 (2s, 18-CH$_3$ and 19-CH$_3$), 1.20 (s, 17α-CH$_3$) 0.65-1.90 (residual CH and CH$_2$), 2.50-3.30 (broad m, 2×CH$_2$N, 2×CH$_2$NH and 2α-CH), 3.85 (m, 3β-CH).

Preparation of {4-[(2β,3α,17β)-3,17-dihydroxy-17-methylandrostan-2-yl]piperazin-1-yl}[(2S)-1-(naphthalen-2-ylcarbonyl)pyrrolidin-2-yl]methanone (30)

To a solution of compound 29 (80 mg, 0.20 mmol) in anhydrous DMF (5 mL) at room temperature under an atmosphere of argon were added carboxylic acid 20 (61 mg, 0.23 mmol), PyBOP (117 mg, 0.23 mmol), HOBt (30 mg, 0.23 mmol), and DIPEA (114 μL, 0.66 mmol). The solution was subsequently stirred overnight at room temperature. The resulting solution was then poured into water and extracted with EtOAc (2×30 mL), washed with brine, dried with MgSO$_4$ and evaporated to dryness. Purification by two successive flash chromatography procedures using (DCM/MeOH: 95:5) and (Hexanes/Acetone: 1:1) respectively yielded 25 mg (19%) of compound 30. $^1$H NMR (CDCl$_3$) δ: 0.80 (s, 18-CH$_3$), 0.87 (s, 19-CH$_3$), 1.17 (s, 17α-CH$_3$), 0.60-2.30 (residual CH and CH$_2$), 2.30-3.20 (broad m, 2×CH$_2$N et 2α-CH), 3.30-4.20 (broad m, 2×CH$_2$NCO, CH$_2$N of proline and 3β-CH), 5.06 (broad m, NCHCO of proline), 7.56 (m, 2×CH of naphthalene), 7.66 (d, J=7.1 Hz, CH of naphthalene), 7.92 (m, 3×CH of naphthalene), 8.11 (s, CH of naphthalene); $^{13}$C NMR (acetone-d6) δ: 13.7, 20.6, 23.1, 25.2, 25.6, 28.0, 31.8, 33.0, 33.3, 35.9, 36.0, 39.1, 50.8, 56.5, 59.1, 64.2, 65.6, 80.2, 124.8, 126.0, 126.1, 126.5, 126.8, 127.7, 128.5, 132.7, 133.8, 134.8, 168.1, 169.3, 169.9; HRMS: calcd for C$_{40}$H$_{56}$N$_3$O$_4$ [M+H]$^+$ 642.4265, found 642.4272.

Preparation of {4-[(2β,3α,17β)-3,17-dihydroxyandrostan-2-yl]piperazin-1-yl}[(2S)-1-(isoquinolin-3-ylcarbonyl)pyrrolidin-2-yl]methanone (31)

To a solution of compound 10 (250 mg, 0.66 mmol) in anhydrous DMF (15 mL) at room temperature under an atmosphere of argon were added 1-(isoquinolin-3-ylcarbonyl)-pyrrolidine-2-carboxylic acid (197 mg, 0.72 mmol), PyBOP (380 mg, 0.72 mmol), HOBt (99 mg, 0.72 mmol), and DIPEA (370 μL, 2.11 mmol). The solution was subsequently stirred overnight at room temperature. The resulting solution was then poured into water and extracted with EtOAc (2×60 mL), washed with brine, dried with MgSO$_4$ and evaporated to dryness. Purification by two successive flash chromatography procedures using (DCM/MeOH: 95:5) and (Hexanes/Acetone: 1:1) respectively yielded 20 mg (5%) of compound 31. $^1$H NMR (CDCl$_3$) δ: 0.73 and 0.77 (2s, 18-CH$_3$), 0.86 and 0.88 (2s, 19-CH$_3$), 0.65-2.20 (residual CH and CH$_2$), 2.30-2.75 (broad m, 2×CH$_2$N and 2α-CH), 3.30-4.15 (broad m, 2×CH$_2$NCO, CH$_2$N of proline, 17α-CH and 3β-CH), 5.12 and 5.81 (m, NCHCO of proline), 7.70 (m, 2×CH of quinoline), 7.94 (m, 2×CH of quinoline), 8.31 and 8.50 (2s, CH of quinoline), 9.09 and 9.22 (2s, CH of quinoline). $^{13}$C NMR (CDCl$_3$) δ: 11.2, 17.2, 22.1, 23.3, 28.1, 28.9, 30.6, 31.1, 31.8, 32.8, 34.6, 35.5, 35.8, 36.8, 38.5, 42.3, 43.1, 48.7, 50.9, 56.1, 56.1, 57.4, 59.2, 63.8, 64.8, 64.9, 81.9, 122.0, 123.1, 127.5, 127.6, 128.1, 128.7, 128.9, 130.8, 135.8, 136.0, 147.3, 147.5, 149.8, 150.9, 166.1, (166.8), 170.3 (171.0). HRMS: calcd for C$_{38}$H$_{53}$N$_4$O$_4$ [M+H]$^+$ 629.4061, found 629.4063.

Preparation of {4-[(2β,3α,17β)-3,17-dihydroxyandrostan-2-yl]piperazin-1-yl}[(2S)-1-(quinolin-6-ylcarbonyl)pyrrolidin-2-yl]methanone (32)

To a solution of compound 10 (250 mg, 0.66 mmol) in anhydrous DMF (15 mL) at room temperature under an atmosphere of argon were added 1-(quinolin-6-ylcarbonyl)-pyrrolidine-2-carboxylic acid (197 mg, 0.72 mmol), PyBOP (380 mg, 0.72 mmol), HOBt (99 mg, 0.72 mmol), and DIPEA (370 μL, 2.11 mmol). The solution was subsequently stirred overnight at room temperature. The resulting solution was then poured into water and extracted with EtOAc (2×60 mL), washed with brine, dried with MgSO$_4$ and evaporated to dryness. Purification by two successive flash chromatography procedures using (DCM/MeOH: 95:5) and (Hexanes/Acetone: 1:1) respectively yielded 25 mg (6%) of compound 32. $^1$H NMR (CDCl$_3$) δ: 0.69 (s, 18-CH$_3$), 0.87 (s, 19-CH$_3$), 0.65-2.40 (residual CH and CH$_2$), 2.70-3.2 (broad, 2×CH2N and 2α-CH), 3.50-4.20 (broad, 2×CH$_2$NCO, CH$_2$N of proline, 17α-CH, and 3β-CH), 5.05 (broad s, NCHCO of proline), 7.47 (m, CH of quinoline), 7.89 (d, J=8.7 Hz, CH of quinoline), 8.07 (s, CH of quinoline), 8.14 (d, J=8.7 Hz ,CH of quinoline), 8.20 (d, J=8.1 Hz, CH of quinoline), 8.98 (d, J=2.7 Hz,1H of quinoline); $^{13}$C NMR (MeOD-d4) δ : 10.4, 13.3, 20.4, 22.9, 25.1, 27.5, 29.2, 30.7, 31.3, 33.2, 35.9, 36.7, 42.3, 42.8, 44.7, 45.5, (47.0-48.0 residual peaks under solvent) 50.0, 50.3, 51.0, 55.6, 57.3, 59.4, 65.2, 81.1, 122.2, 126.3, 127.3, 127.8, 128.2 (128.3), 134.5 (135.4), 137.6, 147.4 (147.7), 151.3, (151.4), 169.1, (170.3), 170.5, (170.6); HRMS: calcd for C$_{38}$H$_{53}$N$_4$O$_4$ [M+H]$^+$629.4061, found 629.4071.

Preparation of {4-[(2β,3α,17β)-3,17-dihydroxyandrostan-2-yl]piperazin-1-yl}[(2S)-1-(quinolin-2-ylcarbonyl)pyrrolidin-2-yl]methanone (33)

To a solution of compound 10 (250 mg, 0.66 mmol) in anhydrous DMF (15 mL) at room temperature under an atmosphere of argon were added 1-(quinolin-2-ylcarbonyl)-pyrrolidine-2-carboxylic acid (197 mg, 0.72 mmol), PyBOP (380 mg, 0.72 mmol), HOBt (99 mg, 0.72 mmol), and DIPEA (370 μL, 2.11 mmol). The solution was subsequently stirred overnight at room temperature. The resulting solution was then poured into water and extracted with EtOAc (2×60 mL), washed with brine, dried with MgSO$_4$ and evaporated to dryness. Purification by two successive flash chromatography procedures using (DCM/MeOH: 95:5) and (Hexanes/Acetone: 1:1) respectively yielded 41 mg (9%) of compound 33. $^1$H NMR (CDCl$_3$) δ: 0.74 and 0.77 (2s, 18-CH$_3$), 0.82 and 0.87 (2s, 19-CH$_3$), 0.65-2.25 (residual CH and CH$_2$), 2.30-2.80 (broad m, 2×CH$_2$N and 2α-CH), 3.10-4.30 (broad m, 2×CH$_2$NCO, CH$_2$N of proline, 17α-CH and 3β-CH), 5.10 and 5.88 (2 m, NCHCO of proline), 7.59 (m, CH of quinoline), 7.76 (m, CH of quinoline), 7.84 (t, J=8.3 Hz, CH of quinoline), 7.98 (m, 1.5×CH of quinoline), 8.07 (d, J=8.6 Hz, 0.5×CH of quinoline), 8.21 and 8.23 (2d, J=10.0 Hz, CH of quinoline). $^{13}$C NMR (CDCl$_3$) δ: 11.2, 17.2, 22.5, 23.3, 28.1, 29.0, 30.5, 31.1, 32.6, 33.0, 34.5, 35.7, 35.8, 36.8, 38.4, 42.1, 43.1, 45.4, 48.0, 48.3, 50.9, 56.0, 56.1, 57.5, 59.1, 63.7, 64.7, 64.9, 81.8, 121.1, 121.7, 127.6 (127.9), 128.23

(128.29), 129.2, 129.74 (129.86), 136.62 (136.81), 145.80 (146.5), 153.44 (154.17), 166.22 (166.59), 170.06 (170.40). HRMS: calcd for $C_{38}H_{53}N_4O_4$ [M+H]$^+$ 629.4061, found 629.4061.

Preparation of (17β)-17-methoxyandrost-2-ene (34)

To compound 8 (200 mg, 0.73 mmol) in anhydrous DMF (25 mL) under an argon atmosphere was added NaH (60% in oil; 203 mg, 5.1 mmol). The solution was stirred at 0° C. over a period of 1 h and methyl iodide (0.72 mL, 11.7 mmol) was added. The solution was subsequently stirred overnight at room temperature. The resulting solution was then diluted with EtOAc (100 mL) and washed with a saturated solution of ammonium chloride. The organic layer was washed with water and brine, dried over $Na_2SO_4$, filtered and evaporated under reduced pressure. The crude compound was purified by flash chromatography using Hexanes/EtOAc (95:5) as eluant to yield compound 34 (160 mg, 76%). $^1$H NMR (CDCl$_3$) δ: 0.76 (s, 18-CH$_3$ and 19-CH$_3$), 0.68-2.05 (residual CH and CH$_2$), 3.22 (t, J=8.2 Hz, 17α-CH), 3.35 (s, OCH$_3$), 5.59 (m, 2×CH of alkene).

Preparation of (2α,3α,17β)-17-methoxy-2,3-epoxyandrostane (35)

To a solution of compound 34 (160 mg, 0.55 mmol) in anhydrous dichloromethane (10 mL) was added m-CPBA (149 mg, 0.67 mmol) at 0° C. under an atmosphere of argon. The solution was stirred at 0° C. over a period of 3 h. The solution was subsequently diluted with dichloromethane (50 mL) and washed with an aqueous sodium bicarbonate solution (10%). The organic layer was dried with sodium sulfate and evaporated under reduced pressure. The crude compound was purified by flash chromatography (Hexanes/acetone: 9:1) to yield compound 35 (127 mg, 75%). $^1$H NMR (CDCl$_3$) δ: 0.73 (s, 18-CH$_3$), 0.76 (s, 19-CH$_3$), 0.58-2.05 (residual CH and CH$_2$), 3.12 and 3.15 (2 m, 2×CH of epoxide), 3.21 (t, J=8.2 Hz, 17α-CH), 3.34 (s, OCH$_3$).

Preparation of (2β,3α,17β)-17-methoxy-2-(piperazin-1-yl)androstan-3-ol (36)

To compound 35 (100 mg, 0.33 mmol) was added water (1 mL) and piperazine (3.5g, 41 mmol). The solution was subsequently heated at 150° C. over a period of 24 h. The resulting mixture was diluted with dichloromethane (50 mL) and washed with water, dried with $Na_2SO_4$, filtered and evaporated under reduced pressure. The crude compound was purified by flash chromatography (DCM/MeOH: 9:1 containing 0.5% of TEA) to yield compound 36 (90 mg, 70%). $^1$H NMR (CDCl$_3$) δ: 0.72 (s, 18-CH$_3$), 0.82 (s, 19-CH$_3$), 0.65-2.05 (residual CH and CH$_2$), 2.38, 2.60 and 2.86 (3m, 4×CH$_2$N and 2α-CH), 3.18 (t, J=8.2 Hz, 17α-CH), 3.31 (s, OCH$_3$), 3.82 (m, 3β-CH).

Preparation of {4-[(2β,3α,17β)-3-hydroxy-17-methoxyandrostan-2-yl]piperazin-1-yl}[(2S)-1-(naphthalen-2-ylcarbonyl)pyrrolidin-2-yl]methanone (37)

To a solution of compound 36 (90 mg, 0.23 mmol) in anhydrous DMF (5 mL) at room temperature under an atmosphere of argon were added carboxylic acid 20 (68 mg, 0.25 mmol), PyBOP (132 mg, 0.25 mmol), HOBt (34 mg, 0.25 mmol), and DIPEA (128 μL, 0.74 mmol). The solution was subsequently stirred overnight at room temperature. The resulting solution was then poured into water and extracted with EtOAc (2×30 mL), washed with brine, dried with MgSO$_4$ and evaporated to dryness. Purification by two successive flash chromatography procedures using (DCM/MeOH: 95:5) and (Hexanes/Acetone: 1:1) respectively and trituration with diethyl ether yielded 35 mg (23%) of compound 37. $^1$H NMR (CDCl$_3$) δ: 0.73 (s, 18-CH$_3$), 0.84 (s, 19-CH$_3$), 0.65-2.25 (residual CH and CH$_2$), 2.40-2.75 (broad m, 2×CH$_2$N and 2α-CH), 3.19 (t, J=8.3 Hz, 17α-CH), 3.32 (s, OCH$_3$), 3.45-3.95 (broad m, 2×CH$_2$NCO, CH$_2$N of proline and 3β-CH), 5.14 (t, J=7.6 Hz, NCHCO of proline), 7.52 (m, 2×CH of naphthalene), 7.67 (d, J=8.4 Hz, CH of naphthalene), 7.85 (m, 3×CH of naphthalene), 8.09 (s, CH of naphthalene). $^{13}$C NMR (CDCl$_3$) δ: 11.7, 17.1, 21.0, 23.2, 27.6, 28.1, 29.4, 33.0, 35.2, 35.8, 38.4, 43.0, 48.0, 49.0, 50.3, 51.1, 55.7, 56.0, 56.2, 57.8, 59.3, 63.6, 63.8, 64.1, 64.7, 65.0, 66.9, 90.7, 126.6, 127.2, 127.4, 127.7, 127.8, 128.0, 128.6, 132.5, 133.6, 133.9, 169.5, 170.4 HRMS: calcd for $C_{40}H_{55}N_3O_4$: 642.4265, found [M+H]$^+$ 642.4274.

Preparation of 2,2'-{[(2β,3α,5α,17β)-2-{4-[1-(naphthalen-2-ylcarbonyl)-L-prolyl]piperazin-1-yl}androstane-3,17-diyl]bis(oxycarbonyl)}dibenzoic acid (38)

To a solution of compound PC-37 (50 mg, 0.08 mmol) in anhydrous pyridine (1 mL) was added DMAP (19 mg, 0.16 mmol) and phthalic anhydride (24 mg, 0.16 mmol). The resulting solution was subsequently stirred overnight at room temperature under an argon atmosphere and evaporated under reduce pressure. Purification by flash chromatography (DCM/MeOH: 95:5) yielded compound 38 (9 mg, 12%). $^1$H NMR (CDCl$_3$) δ: 0.83 (s, 18-CH$_3$), 1.11 (s, 19-CH$_3$), 0.70-2.35 (residual CH and CH$_2$), 2.4-4.2 (broad m, 2×CH$_2$N, 2α-CH, 2×CH$_2$NCO and CH$_2$N of proline), 4.79 (m, 17α-CH), 5.12 (broad t, 3β-CH), 4.91 and 5.32 (2 broad s, NCHCO of proline), 7.45-8.05 (m, 6×CH of naphthalene and 6×CH of aryl), 8.14 (s, CH of naphthalene).

Preparation of (2β,3α,17β)-2-{4-[1-(naphthalen-2-ylcarbonyl)-L-prolyl]piperazin-1-yl}androstane-3,17-diyl disulfamate (39)

To a solution of compound PC-37 (60 mg, 0.1 mmol) in anhydrous dichloromethane (12 mL) was added 2,6-di-tert-butylmethyl pyridine (118 mg, 0.58 mmol) and sulfamoylchloride (66 mg, 0.57 mmol). The solution was stirred over a period of 1 h followed by the addition of a second portion of 2,6-di-tert-butylmethyl pyridine (118 mg, 0.58 mmol) and sulfamoylchloride (66 mg, 0.57 mmol). The resulting solution was subsequently stirred for an additional hour. The solution was then diluted with dichloromethane (50 mL) and washed with water. The organic layer was dried over $Na_2SO_4$ and evaporated under reduced pressure. The crude compound was purified by flash chromatography (DCM/MeOH: 95:5) to yield compound 39 (34 mg, 45%). $^1$H NMR (acetone-d$_6$) δ: 0.75 and 0.79 (2s, 18-CH$_3$), 0.91 and 1.10 (2s, 19-CH$_3$), 0.65-2.40 (residual CH and CH$_2$), 2.40-3.25 (broad m, 2×CH$_2$N and 2α-CH), 3.50-3.80 (broad m, 2×CH$_2$NCO, CH$_2$N of proline), 4.36 (broad t, J=5.6 Hz, 17α-CH), 4.78 and 5.00 (2s, 3β-CH), 4.90 and 5.13 (2m, NCHCO of proline), 6.60 (s, SO$_2$NH$_2$), 6.71 and 6.80 (2s, SO$_2$NH$_2$), 7.46 and 7.70 (2d, J$_1$=8.4 Hz, CH of naphthalene), 7.57 (m, 2×CH of naphthalene, 7.96 (m, 3.5×CH naphthalene) 8.13 (s, 0.5×CH of naphthalene); HRMS: calcd for $C_{39}H_{55}N_5O_8S_2$: 786.3565 found [M$^+$] 786.3572.

Preparation of (2β,3α,5α)-3-hydroxy-2-(4-{[(2S)-1-(naphthalen-1-ylcarbonybpyrrolidin-2-yl]carbonyl}piperazin-1-yl)androstan-17-one (40)

To a solution of compound 23 (200 mg, 0.54 mmol) in anhydrous DMF (7 mL) at room temperature under an atmosphere of argon were added 1-(naphtalen-1-ylcarbonyl)-L-proline (214 mg, 0.70 mmol), PyBOP (363 mg, 0.70 mmol), HOBt (95 mg, 0.70 mmol), and DIPEA (375 μL, 2.15 mmol). The solution was subsequently stirred overnight at room temperature. The resulting solution was then poured into water and extracted with EtOAc (2×30 mL), washed with brine, dried with MgSO₄ and evaporated to dryness. Purification by two successive flash chromatography procedures using (DCM/MeOH: 95:5) and (Hexanes/Acetone: 1:1) respectively yielded 100 mg (28%) of compound 40. ¹H NMR (CDCl₃) δ: 0.85 (s, 18-CH₃), 0.88 (s, 19-CH₃), 0.70-2.35 (residual CH and CH₂), 2.40-4.05 (broad, 16β-CH, NCH₂ of proline, 2×CH₂NCO, 2×CH₂N, 2α-CH, and 3β-CH), 5.19 (broad, NCHCO of proline), 7.51 (m, 3×CH of naphthalene), 7.59 (t, J=7.0 Hz, CH of naphthalene), 7.87 (t, J=6.7 Hz, 2×CH of naphthalene), 8.26 (s, CH of naphthalene).

Preparation of {4-[(2β,3α,5α,17α)-3,17-dihydroxy-21-(trimethylsilyl)pregn-20-yn-2-yl]piperazin-1-yl}[(2S)-1-(naphthalen-1-ylcarbonyl)pyrrolidin-2-yl]methanone (41)

To a solution of trimethylacetylene (0.105 mL, 0.75 mmol) in anhydrous ethyl ether (10 mL) at 0° C. under an atmosphere of argon was added dropwise MeLi (0.38 mL, 0.60 mmol). The solution was allowed to return to room temperature and stirred over a period of 1h. The solution was subsequently cooled to 0° C. and compound 40 (100 mg, 0.15 mmol) in anhydrous THF (20 mL) was slowly added. The resulting solution was stirred for an additional 4 h at room temperature. The solution was then diluted with ethyl acetate (100 mL) and washed with a saturated ammonium chloride aqueous solution (3×50 mL). The organic layer was dried over Na₂SO₄, filtered and evaporated under reduced pressure. The crude compound was purified by flash chromatography (DCM/MeOH: 95:5) to yield compound 41 (98 mg, 85%). ¹H NMR (CDCl₃) δ: 0.17 (m, (CH₃)₃Si), 0.80 (s, 18-CH₃), 0.85 (s, 19-CH₃), 0.60-2.35 (residual CH and CH₂), 2.40-2.80 (broad m, 2×NCH₂ and 2α-CH), 3.15-4.00 (broad m, NCH₂ of proline, 2×CH₂NCO and 3β-CH), 5.17 (broad, NCHCO of proline), 7.50 (m, 3×CH of naphthalene), 7.58 (t, J=7.0 Hz, CH of naphthalene), 7.86 (t, J=6.7 Hz, 2×CH of naphthalene), 8.29 (s, CH of naphthalene).

Preparation of {4-[(2β,3α,5α,17α)-3,17-dihydroxypregn-20-yn-2-yl]piperazin-1-yl}[(2S)-1-(naphthalen-1-ylcarbonyl)pyrrolidin-2-yl]methanone (42)

Compound 41 (98 mg, 0.13 mmol) was dissolved in methanol (10 mL) and K₂CO₃ (1.0 g) was added. The solution was then vigorously stirred over a period of 3 h. The solution was subsequently filtered, diluted with ethyl acetate (50 mL) and neutralized with an aqueous ammonium chloride solution to pH 7. The organic layer was washed with brine, dried with Na₂SO₄ and evaporated under reduced pressure. The crude compound was purified by flash chromatography using DCM/MeOH (5:95) as eluant to yield compound 42 (40 mg, 45%). ¹H NMR (CDCl₃) δ: 0.82 (s, 18-CH₃) 0.85, (s, 19-CH₃), 0.70-2.35 (residual CH and CH₂), 2.42-2.80 (broad m, 2×CH₂N and 2α-CH), 2.55 (s, CH of ethynyl), 3.15-4.05 (broad m, 2×CH₂NCO, CH₂N of proline, 3β-CH), 5.18 (broad s, NCHCO of proline), 7.51 (m, 3×CH of naphthalene), 7.59 (t, J=7.2 Hz, CH of naphthalene), 7.87 (t, J=6.8 Hz, 2×CH of naphthalene), 8.28 (s, CH of naphthalene).

Preparation of (2β,3α,5α)-3-hydroxy-2-(4-{[(2S)-1-(isoquinolin-3-ylcarbonyl)pyrrolidin-2-yl]carbonyl}piperazin-1-yl)androstan-17-one (43)

To a solution of compound 23 (356 mg, 0.95 mmol) in anhydrous DMF (5 mL) at room temperature under an atmosphere of argon were added 1-(isoquinolin-3-ylcarbonyl)-L-proline (335 mg, 1.2 mmol), PyBOP (647 mg, 1.2 mmol), HOBt (168 mg, 1.2 mmol), and DIPEA (662 μL, 3.8 mmol). The solution was subsequently stirred overnight at room temperature. The resulting solution was then poured into water and extracted with EtOAc (2×30 mL), washed with brine, dried with MgSO₄ and evaporated to dryness. Purification by two successive flash chromatography procedures using (DCM/MeOH: 95:5) and (Hexanes/Acetone: 1:1) respectively yielded 302 mg (50%) of compound 43. ¹H NMR (CDCl₃) δ: 0.84 and 0.86 (2s, 18-CH₃), 0.89 and 0.90 (2s, 19-CH₃), 0.70-2.30 (residual CH and CH₂), 2.35-2.85 (broad m, 2×CH₂N, 16β-CH and 2α-CH), 3.10-4.27 (broad m, 2×CH₂NCO, CH₂N of proline, and 3β-CH), 5.10 and 5.88 (2m, NCHCO of proline), 7.58 (m, CH of quinoline), 7.76 (m, CH of quinoline), 7.84 (t, J=8.3 Hz, CH of quinoline), 7.98 (t, J=8.7 Hz, CH of quinoline), 8.02 and 8.12 (2d, J=8.6 Hz, CH of quinoline), 8.21 and 8.24 (2d, J=8.9 Hz, CH of quinoline).

Preparation of {4-[(2β,3α,5α,17α)-3,17-dihydroxy-21-(trimethylsilyl)pregn-20-yn-2-yl]piperazin-1-yl}[(2S)-1-(isoquinolin-3-ylcarbonyl)pyrrolidin-2-yl]methanone (44)

To a solution of trimethylacetylene (0.122 mL, 0.88 mmol) in anhydrous ethyl ether (10 mL) at 0° C. under an atmosphere of argon was added dropwise MeLi (0.44 mL, 0.70 mmol). The solution was allowed to return to room temperature and stirred over a period of 1 h. The solution was subsequently cooled to 0° C. and compound 43 (110 mg, 0.18 mmol) in anhydrous THF (20 mL) was slowly added. The resulting solution was stirred for an additional 4 h at room temperature. The solution was then diluted with ethyl acetate (100 mL) and washed with a saturated ammonium chloride aqueous solution (3×50 mL). The organic layer was dried over Na₂SO₄, filtered and evaporated under reduced pressure. The crude compound was purified by flash chromatography (DCM/MeOH: 95:5) to yield compound 44 (50 mg, 39%). ¹H NMR (CDCl₃) δ: 0.18 and 0.19 (2s, (CH₃)₃Si), 0.82 and 0.83 (2s, 18-CH₃), 0.87 (s, 19-CH₃), 0.62-2.30 (residual CH and CH₂), 2.32-2.90 (broad m, 2×NCH₂ and 2α-CH), 3.05-4.30 (broad m, NCH₂ of proline, 2×CH₂NCO and 3β-CH), 5.10 and 5.89 (2 m, NCHCO of proline), 7.59 (m, CH of quinoline), 7.75 (m, CH of quinoline), 7.84 (t, J=8.3 Hz, CH of quinoline), 7.98 (t, J=8.7 Hz, CH of quinoline), 8.02 and 8.12 (2d, J=8.5 Hz, CH of quinoline), 8.23 (t, J=8.9 Hz, CH of quinoline).

Preparation of {4-[(2β,3α,5α,17α)-3,17-dihydroxypregn-20-yn-2-yl]piperazin-1-yl}[(2S)-1-(isoquinolin-3-ylcarbonyl)pyrrolidin-2-yl]methanone (45)

Compound 44 (48 mg, 0.13 mmol) was dissolved in methanol (10 mL) and K₂CO₃ (1.0 g) was added. The solution was then vigorously stirred over a period of 3h. The solution was subsequently filtered, diluted with ethyl acetate (50 mL) and neutralized with an aqueous ammonium chloride solution to pH 7. The organic layer was washed with brine, dried with Na₂SO₄ and evaporated under reduced pressure. The crude compound was purified by flash chromatography using DCM/MeOH (5:95) as eluant to yield compound 45 (24 mg, 56%). ¹H NMR (CDCl₃) δ: 0.82 and 0.83 (2s, 18-CH₃), 0.87 and 0.88 (2s, 19-CH₃), 0.70-2.30 (residual CH and CH₂), 2.32-2.90 (broad m, 2×CH₂N, 16β-CH and 2α-CH), 2.58 (2 s, CH of ethynyl), 3.10-4.25 (broad m, 2×CH₂NCO, CH₂N of proline, and 3β-CH), 5.10 and 5.89 (2m, NCHCO of proline), 7.58 (m, CH of quinoline), 7.76 (m, CH of quinoline), 7.84 (t, J=8.3 Hz, CH of quinoline), 7.98 (t, J=8.7 Hz, CH of quinoline), 8.02 and 8.12 (2d, J=8.6 Hz, CH of quinoline), 8.23 (t, J=8.9 Hz, CH of quinoline).

Preparation of {4-[(2β,3α,5α,17β)-3,17-dihydroxyandrostan-2-yl]piperazin-1-yl}[(2S)-1-(naphthalen-1-ylcarbonyl)pyrrolidin-2-yl]methanone (46)

To a solution of compound 10 (100 mg, 0.27 mmol) in anhydrous DMF (5 mL) at room temperature under an atmosphere of argon were added 1-(naphtalen-1-ylcarbonyl)-L-proline (106 mg, 0.35 mmol), PyBOP (181 mg, 0.35 mmol), HOBt (47 mg, 0.35 mmol), and DIPEA (186 μL, 1.1 mmol). The solution was subsequently stirred overnight at room temperature. The resulting solution was then poured into water and extracted with EtOAc (2×30 mL), washed with brine, dried with MgSO$_4$ and evaporated to dryness. Purification by two successive flash chromatography procedures using (DCM/MeOH: 95:5) and (Hexanes/Acetone: 1:1) respectively yielded 90 mg (51%) of compound 46. $^1$H NMR (CDCl$_3$) δ: 0.72 (s, 18-CH$_3$), 0.85 (s, 19-CH$_3$), 0.66-2.34 (residual CH and CH$_2$), 2.40-2.89 (broad m, 2×CH$_2$N and 2α-CH), 3.15-4.05 (broad, NCH$_2$ of proline, 2×CH$_2$NCO, 17α-CH and 3β-CH), 5.19 (m, NCHCO of proline), 7.50 (m, 3×CH of naphthalene), 7.59 (t, J=Hz, 7.0 Hz, CH of naphthalene), 7.87 (t, J=6.7 Hz, 2×CH of naphthalene), 8.27 (s, CH of naphthalene).

Preparation of {4-[(2β,3α,5α,17β)-3,17-dihydroxyandrostan-2-yl[piperazin-1-yl]}{(2S)-1-[(1-oxidoquinolin-3-yl)carbonyl]pyrrolidin-2-yl}methanone (47)

To a solution of compound 10 (100 mg, 0.27 mmol) in anhydrous DMF (5 mL) at room temperature under an atmosphere of argon were added [(1-oxidoquinolin-3-yl)carbonyl]-L-proline (100 mg, 0.35 mmol), PyBOP (182 mg, 0.35 mmol), HOBt (47 mg, 0.35 mmol), and DIPEA (186 μL, 1.1 mmol). The solution was subsequently stirred over a period of 4 hours at room temperature. The resulting solution was then poured into water and extracted with EtOAc (2×30 mL), washed with brine, dried with Na$_2$SO$_4$ and evaporated to dryness. Purification by flash chromatography using (DCM/MeOH: 9:1) yielded 100 mg (58%) of compound 47. $^1$H NMR (CDCl$_3$) δ: 0.72 (s, 18-CH$_3$), 0.86 (s, 19-CH$_3$), 0.68-2.35 (residual CH and CH$_2$), 2.40-2.90 (broad m, 2×CH$_2$N and 2α-CH), 3.05-3.95 (broad, NCH$_2$ of proline, 2×CH$_2$NCO, 17α-CH and 3β-CH), 5.08 (broad, NCHCO of proline), 7.70 (t, J=7.5 Hz, CH of quinoline), 7.83 (t, J=7.3 Hz, CH of quinoline), 7.86 (d, J=8.0 Hz, CH of quinoline), 7.96 (s, CH of quinoline), 8.72 (s, CH of quinoline), 8.75 (d, J=8.8 Hz, CH of quinoline).

Preparation of {4-[(2β,3α,5α,17β)-3,17-dihydroxyandrostan-2-yl]piperazin-1-yl}[(2S)-1-(quinolin-3-ylcarbonyl)pyrrolidin-2-yl]methanone (48)

To a solution of compound 10 (200 mg, 0.54 mmol) in anhydrous DMF (5 mL) at room temperature under an atmosphere of argon were added 1-(quinolin-3-ylcarbonyl)-L-proline (187 mg, 0.70 mmol), PyBOP (364 mg, 0.70 mmol), HOBt (94 mg, 0.70 mmol), and DIPEA (372 μL, 2.1 mmol). The solution was subsequently stirred overnight at room temperature. The resulting solution was then poured into water and extracted with EtOAc (2×30 mL), washed with brine, dried with MgSO$_4$ and evaporated to dryness. Purification by two successive flash chromatography procedures using (DCM/MeOH: 95:5) and (Hexanes/Acetone: 1:1) respectively yielded 20 mg (6%) of compound 48. $^1$H NMR (CDCl$_3$) δ: 0.72 (s, 18-CH$_3$), 0.86 (s, 19-CH$_3$), 0.65-2.38 (residual CH and CH$_2$), 2.40-2.90 (broad m, 2×CH$_2$N and 2α-CH), 3.02-3.92 (broad, NCH$_2$ of proline, 2×CH$_2$NCO, 17α-CH and 3β-CH), 5.12 (broad, NCHCO of proline), 7.61 (t, J=7.2 Hz, CH of quinoline), 7.79 (t, J=7.0 Hz, CH of quinoline), 7.86 (d, J=8.1 Hz, CH of quinoline), 8.14 (d, J=8.5 Hz, CH of quinoline), 8.41 (s, CH of quinoline), 9.12 (s, CH of quinoline).

Preparation of {4-[(2β,3α,5α,17β)-3,17-dihydroxyandrostan-2-yl]-4-oxidopiperazin-1-yl}[(2S)-1-(quinolin-3-ylcarbonyl)pyrrolidin-2-yl]methanone (49)

To a solution of compound 48 (52 mg, 0.08 mmol) in MeOH (4 mL) was added oxone (25 mg, 0.04 mmol) in water (1 ml). The solution was stirred at room temperature over a period of 4 h. The resulting solution was subsequently poured into water (75 mL) and extracted with EtOAc (2×20 mL), washed with brine, dried with MgSO$_4$ and evaporated to dryness. Purification by flash chromatography using (DCM/MeOH: 95:5) yielded 30 mg (56%) of compound 49. $^1$H NMR (CDCl$_3$) δ: 0.57 (s, 18-CH$_3$), 0.95 (s, 19-CH$_3$), 0.55-2.40 (residual CH and CH$_2$), 3.40-4.8 (broad m, 2×CH$_2$N, 2α-CH, NCH$_2$ of proline, 2'CH$_2$NCO, 17α-CH and 3β-CH), 5.11 (t, J=7.4 Hz, NCHCO of proline), 7.64 (t, J=7.0 Hz, CH of quinoline), 7.82 (t, J=7.1 Hz, CH of quinoline), 7.87 (d, J=8.1 Hz, CH of quinoline), 7.15 (d, J=8.5 Hz, CH of quinoline), 8.36 (d, J=1.6 Hz, CH of quinoline), 9.08 (d, J=1.9 Hz, CH of quinoline).

It is to be understood that the disclosure is not limited in its application to the details of construction and parts as described hereinabove. The disclosure is capable of other embodiments and of being practiced in various ways. It is also understood that the phraseology or terminology used herein is for the purpose of description and not limitation. Hence, although the present invention has been described hereinabove by way of illustrative embodiments thereof, it can be modified, without departing from the spirit, scope and nature of the subject disclosure as defined in the appended claims.

References:
1. a) Huggins C, Hodges C V (1941) *Cancer Res.* 1: 293; b) Rasmusson G H (1986) *Ann. Rep. Med. Chem.* 21: 179.
2. a) McGuire W L, Carbone P P Sears M E, Escher G C (1975) In: Estrogen Receptors in Human Breast Cancer (McGuire W L, Carbone P P, Vollmer E P, eds), Raven Press, NY, pp. 1-7; b) Dickson R B, Lippman M E (1987) *Endocr. Rev.* 8: 29.
3. National Cancer Institute of Canada; *Canadian Cancer Statistics* (2004) Toronto, Canada.
4. a) Labrie F, Dupont A, Belanger A (1985) In: Important Advances in Oncology (De Vita V T, Hellman S, Rosenbert S A, eds), J. B. Lippincott, Philadelphia, pp. 193-217; b) Labrie F, Cusan L, Gomez J L, Diamond P, Suburu R, Lemay M, Têtu B, Fradet Y, Candas B (1994) *Urology* 44: 29; c) Labrie F, Cusan L, Gomez J, Luu-The V, Candas B, Bélanger A, Labrie C (2004) *J Steroid Biochem. Molec. Biol.* 92: 327.
5. Taplin, M. E. (2007) *Nat. Clin. Prat.* 4: 236.
6. a) Chauvergne, J.; Hoerni, B. Chimiothérapie anticancéreuse, *Collection Abrégés de Médecine*, (1998) édition Masson, Paris, 105 pages.; b) Chowdhury, S.; Burbridge, S.; Harper, P. G. (2007) *Int. J. Clin. Pract.* 61: 2064.

7. Ferlay, J., Bray, F., Pisani, P., Parkin, D. M. GLOBOCAN 2002: Cancer Incidence, Mortality and Prevalence Worldwide. IARC Cancer base No 5, version 2, IARC Press, Lyon. 2004.
8. U.S. Cancer Statistics Working group. United States Cancer Statistics: (1999-2002) Incidence and Mortality Web based Report Version. Atlanta: Department of Health and Human Services, Centers for Disease Control and Prevention and National Cancer Institute. 2005.
9. McGuire, W. P., Hoskins, W. J., Brady, M. F. (1996) *N. Engl. J. Med.* 334: 1.
10. The International Collaborative Ovarian Neoplasm (ICON) Group. (2002) Lancet, 360:505.
11. Armstrong, D. K., Bundy, B. Wenzel, L. (2006) *N Engl. J. Med.*, 354: 34.
12. National Cancer Institute of Canada: Canadian Cancer Statistics 1995, Toronto, Canada, 1995.
13. http://leukemiabmtprogram.com/public/dideases/html.
14. Harrison, D. J. (1995) *J. Pathol.* 175: 7.
15. Stravrorskaya, A. A. (2000) *Biochemistry* (Mosc) 65: 95.
16. Robert, J., Jarry, C. (2003) *J. Med. Chem.* 46: 4805.
17. Chari, R. V. J. (2008). *Acc. Chem. Res.* 41: 98.
18. J. Roy. Ph.D. Thesis, Université Laval, (2006) Synthèse chimique et activité biologique d'agents stéroïdiens pour le traitement du cancer de la prostate et de la leucémie. N°série: 23962.
19. Roy, J., DeRoy, P., Poirier, D. (2007) 2-beta-(N-substituted piperazino)-5alpha-androstane-3-alpha, 17-beta-diols: parallel solid-phase synthesis and antiproliferative activity on human leukemia HL-60 cells. *J. Comb. Chem.*, 9: 347.
20. Thibeault, D., Roy, J., DeRoy, P., Poirier, D (2008). Chemical synthesis of 2beta-amino-5alpha-androstane-3 alpha, 17-beta-diol N-derivatives and their antiproliferative effect on HL-60 human leukemia cells. *Bioorg. Med. Chem.*, 16: 5062.

What is claimed is:

1. A 2-(N-substituted piperazinyl) steroid derivative of Formula I and having antiproliferative activity:

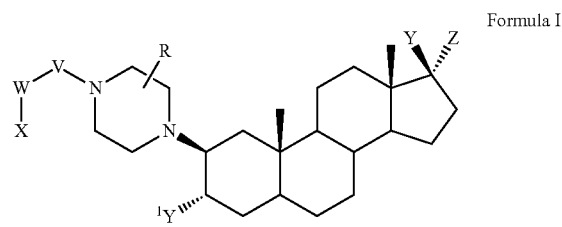

Formula I wherein;
a) Y and $Y^1$ are OH, OMe, $OSO_2NH_2$, CHOHMe, or

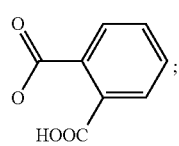 [SMILES: O=C(O)c1ccccc1C(=O)O]

b) Z is H, C≡CH, or Me;
c) Y and Z on the same carbon atom may be a double bonded oxygen (=O);
d) R is H; and
e) V is L-proline, L-phenylalanine, D-proline, D-phenylalanine, or tetrahydroisoquinolone; and wherein the variables W and X are linked to form the linkage W—X, and wherein W—X is selected from the group consisting of

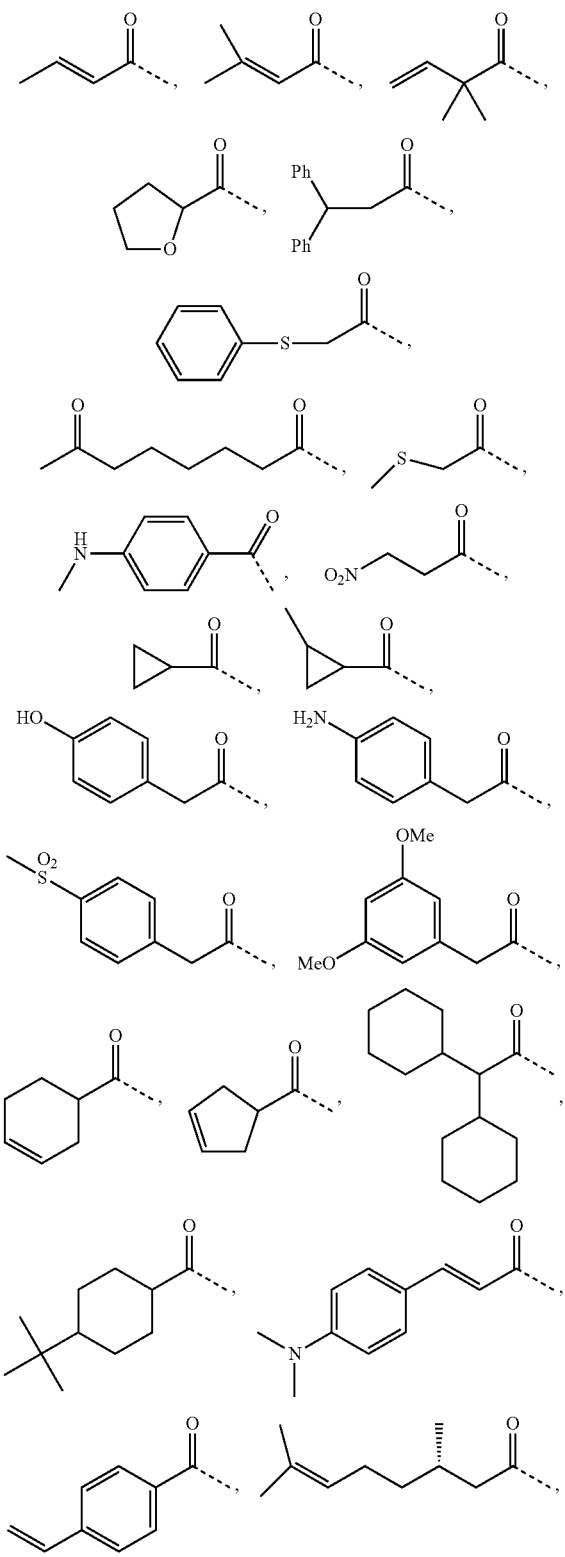

111
-continued
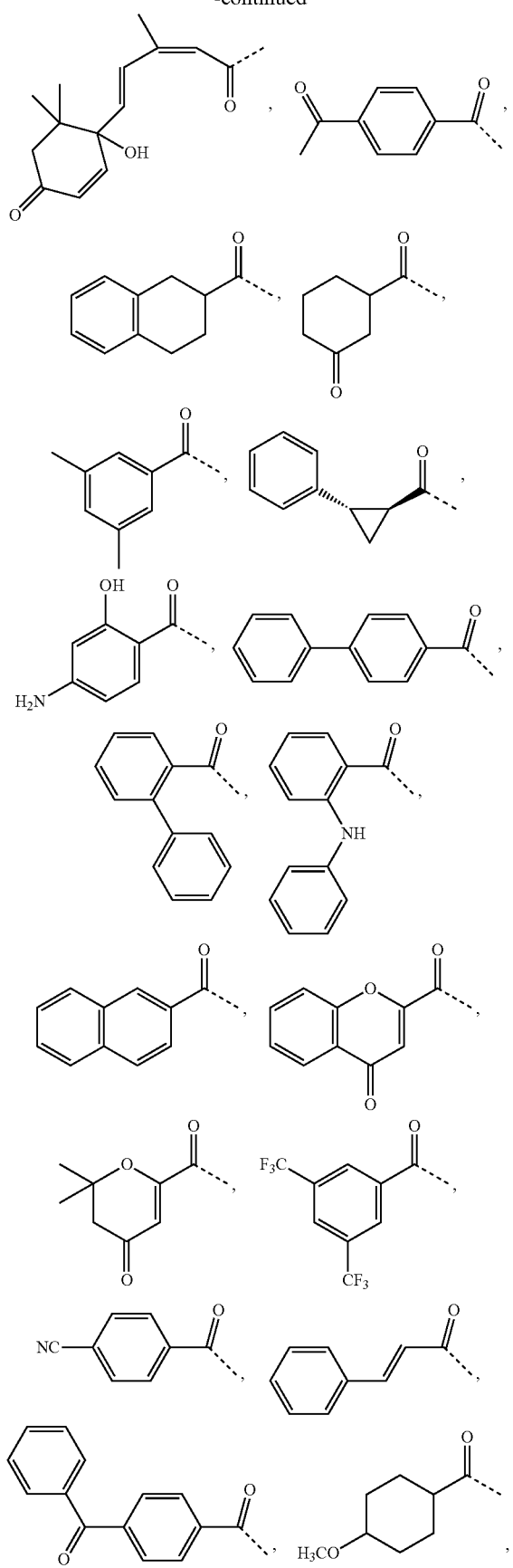
112
-continued
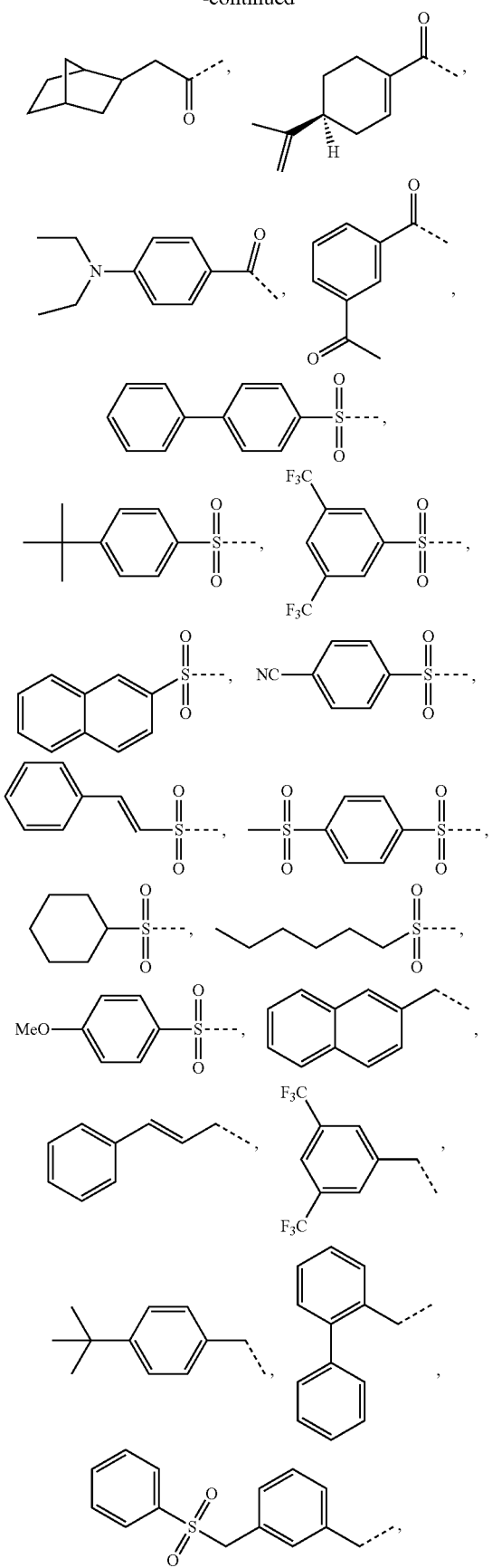

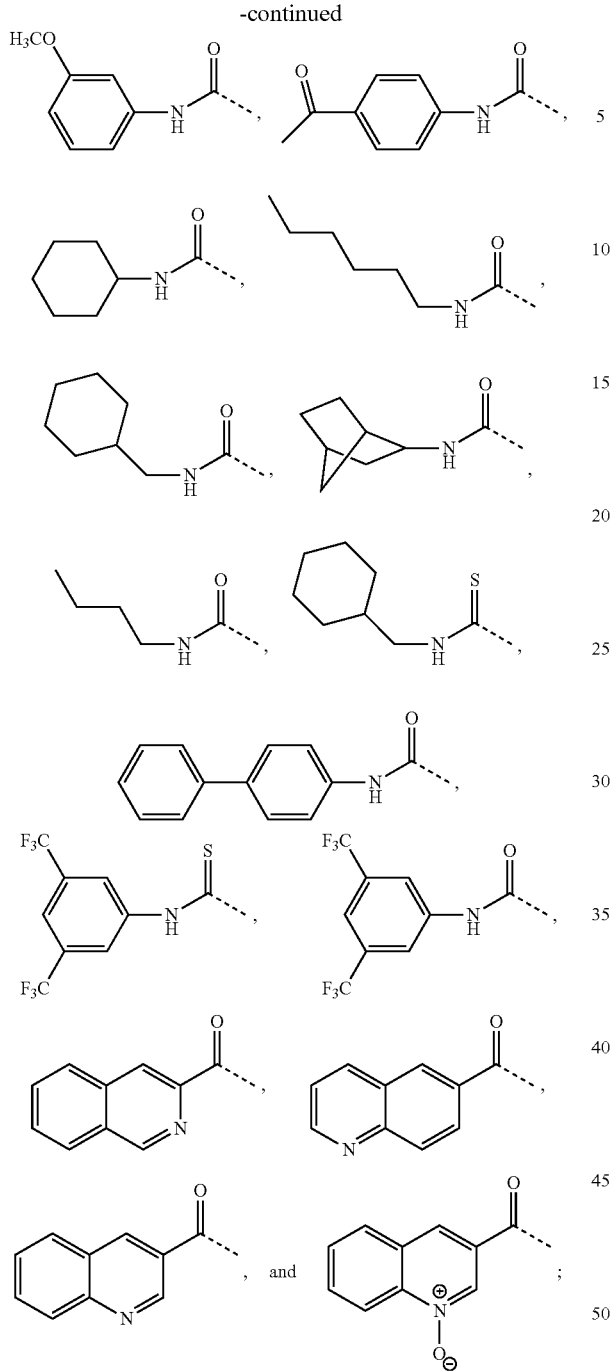

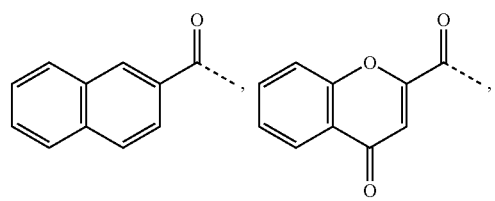
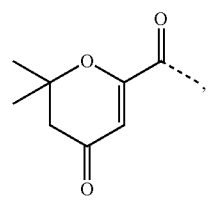
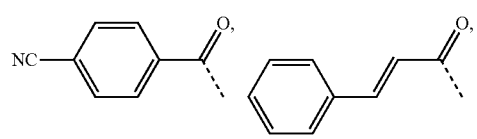
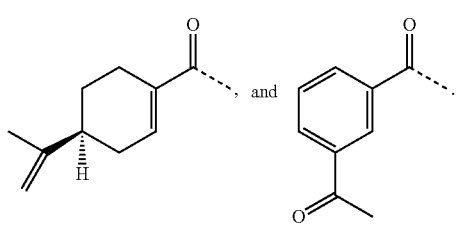

or a pharmaceutically acceptable salt thereof, an N-oxide thereof or a solvate thereof.

2. The steroid derivative according to claim 1, wherein:
a) Y and $Y^1$ are OH and CHOHMe respectively;
b) Z is H;
c) R is H; and
d) V is L-proline, L-phenylalanine, D-proline, or D-phenylalanine; and wherein the variables W and X are linked to form the linkage W-X, and wherein W-X is selected from the group consisting of 3. The steroid derivative according to claim 1, wherein the steroid derivative is:

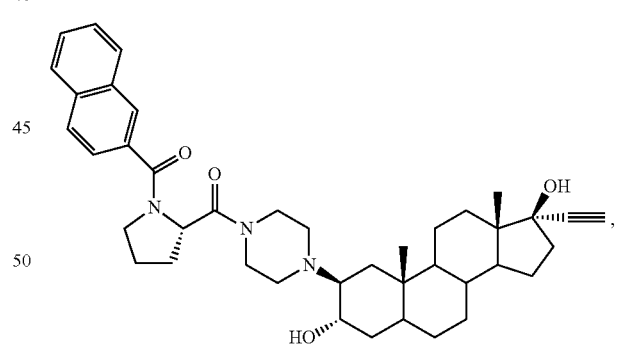

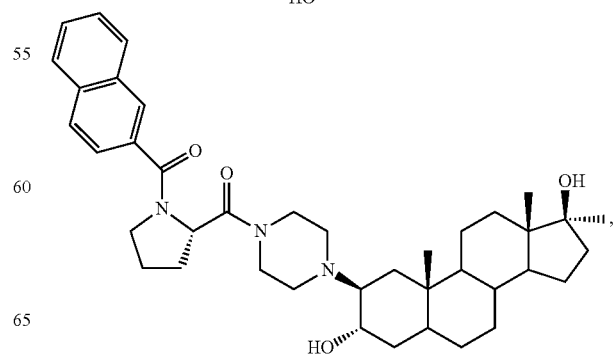

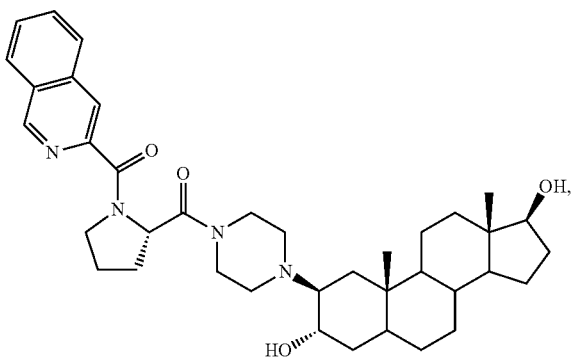
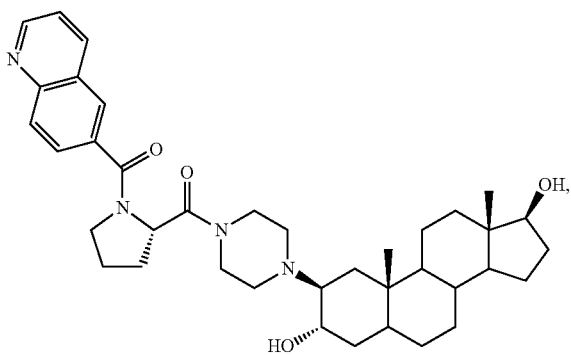
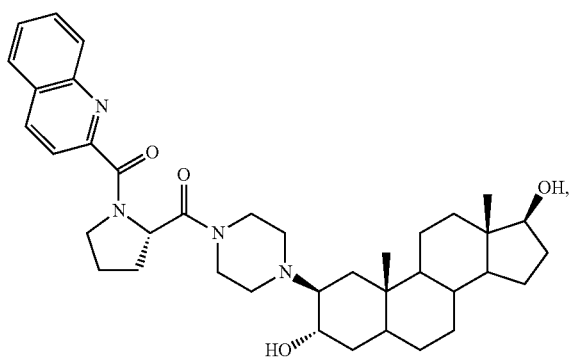
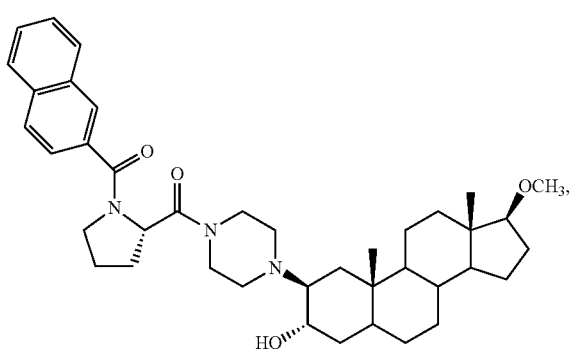
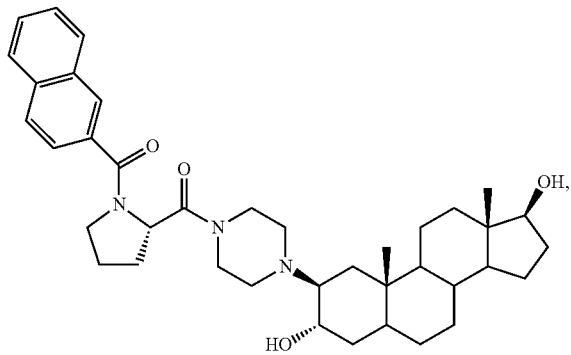
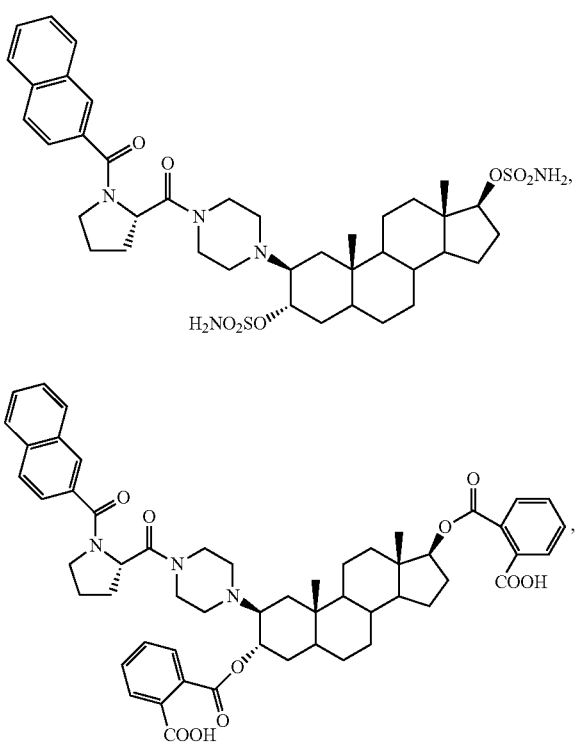
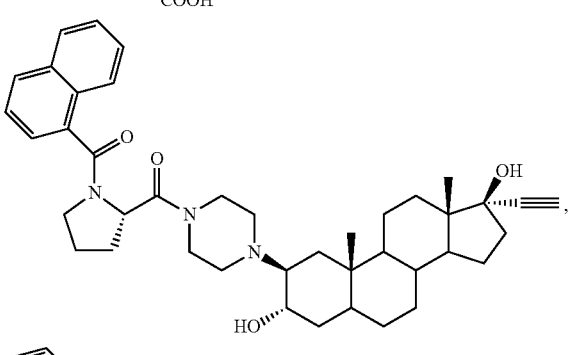
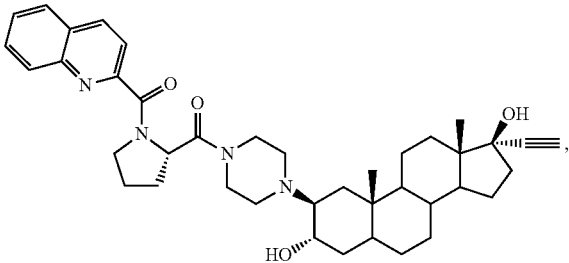

117
-continued

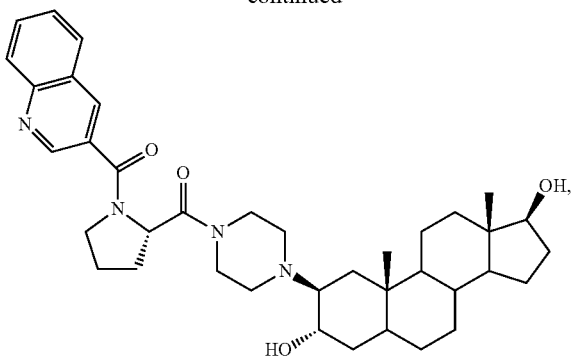

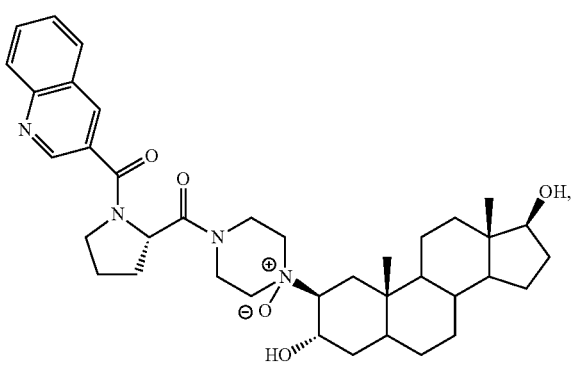

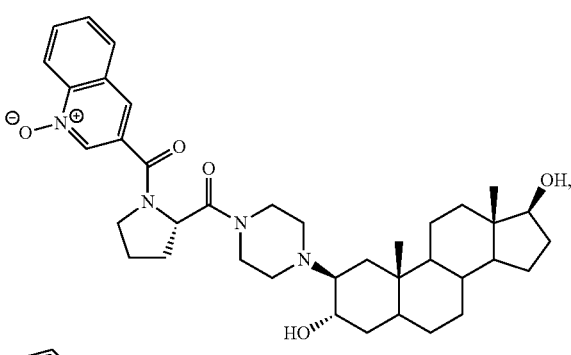

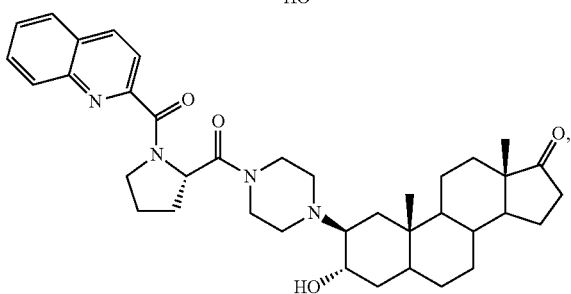

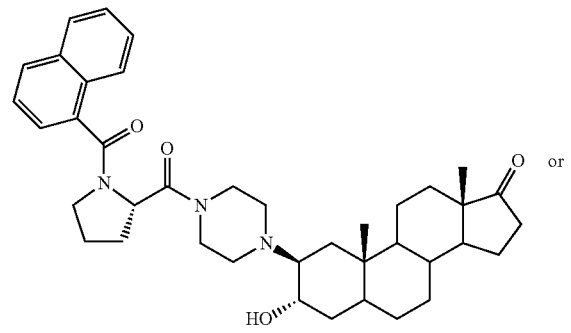

118
-continued

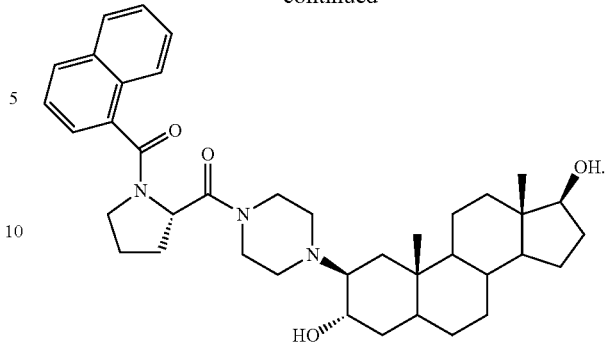

4. A pharmaceutical composition comprising a pharmaceutically acceptable amount of the steroid derivative according to claim 1 and a pharmaceutically acceptable carrier.

5. A method of treating cancer comprising administering to a patient afflicted with cancer, a therapeutically effective amount of one or more steroid derivatives according to claim 1.

6. The method of claim 5, wherein the cancer is selected from the group consisting of breast cancer, prostate cancer, ovarian cancer, leukemia and lymphoid cancer.

7. A pharmaceutical composition comprising an anti-tumor effective amount of the steroid derivative according to claim 1, a pharmaceutically acceptable salt thereof, an N-oxide thereof, or a solvate thereof, and a pharmaceutically acceptable carrier.

8. A pharmaceutical composition comprising an anti-tumor effective amount of a 2-(N-substituted piperazinyl) steroid derivative, a pharmaceutically acceptable salt thereof, an N-oxide thereof, or a solvate thereof, and a pharmaceutically acceptable carrier, wherein the 2-(N-substituted piperazinyl) steroid derivative is of Formula I:

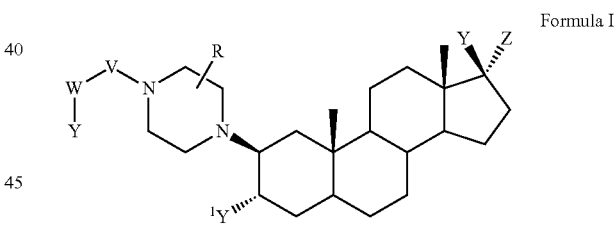

Formula I and wherein:
a) Y and $Y^1$ are OH, OMe, $OSO_2NH_2$, CHOHMe, or

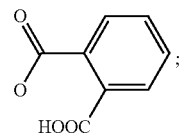

b) Z is H, C≡CH, or Me;
c) Y and Z on the same carbon atom may be a double bonded oxygen (═O);
d) R is H; and
e) V is L-proline, L-phenylalanine, D-proline, D-phenylalanine, or tetrahydroisoquinolone; and
wherein the variables W and X are linked to form the linkage W—X, and wherein W—X is selected from the group consisting of

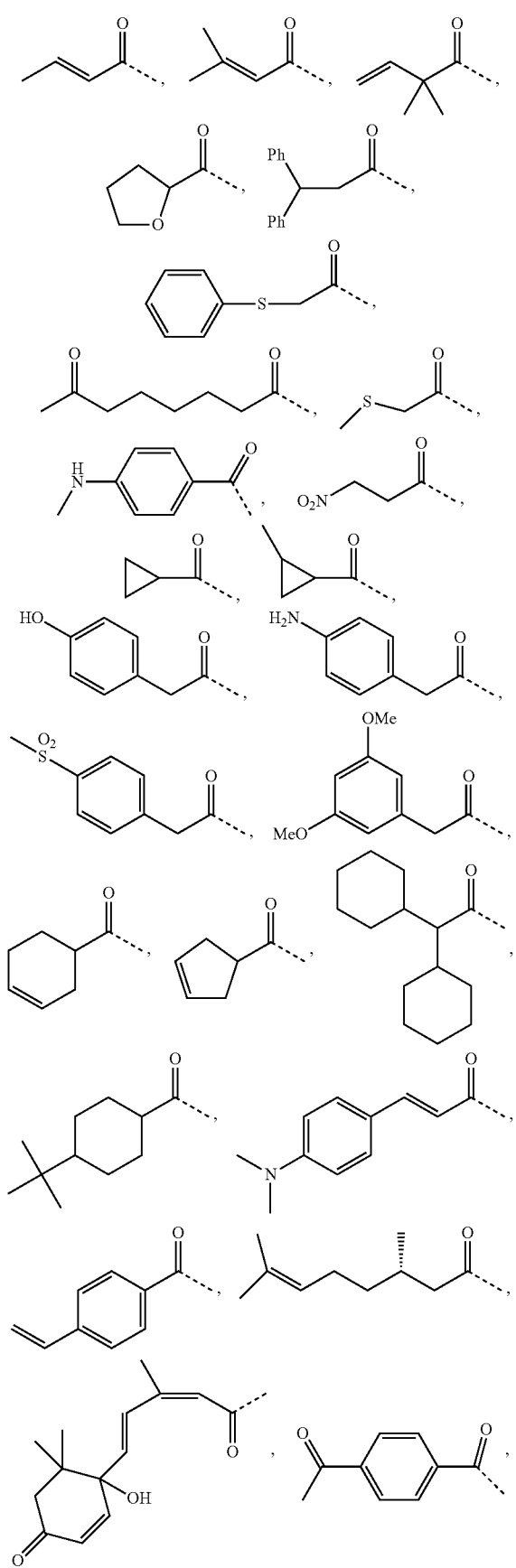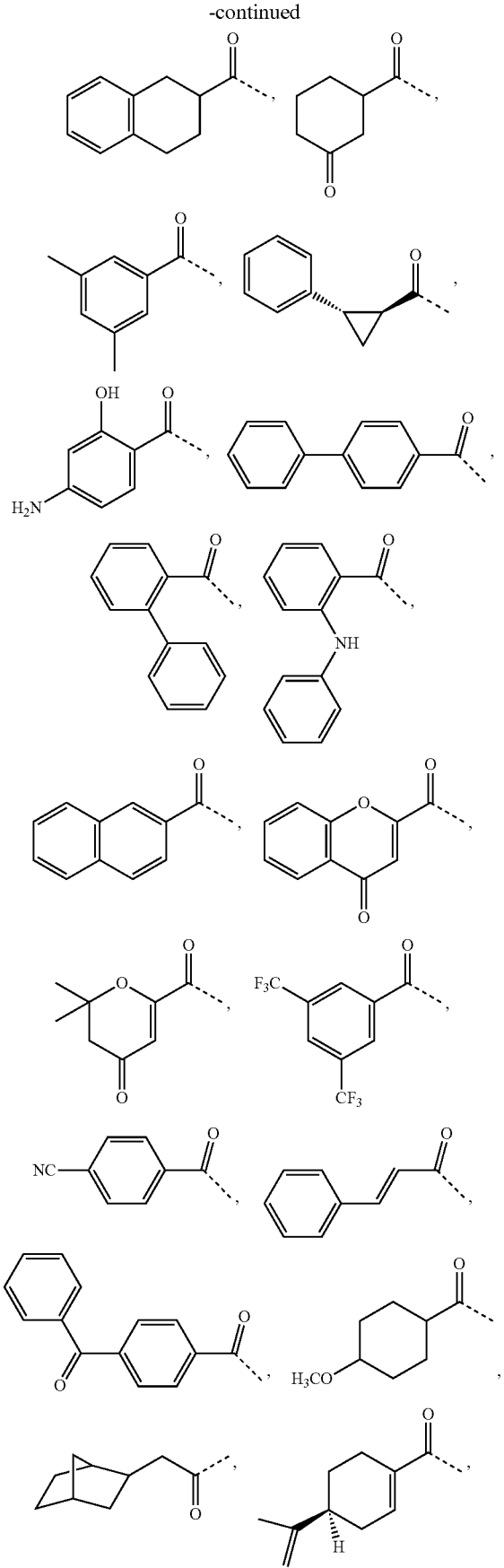

121
-continued

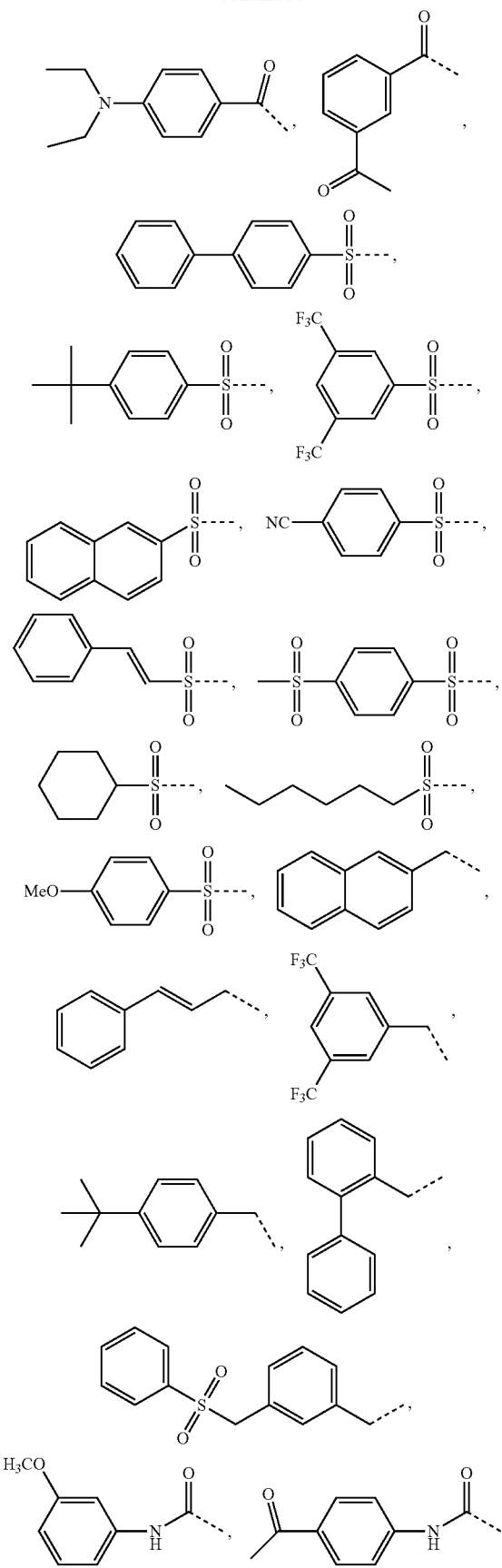

122
-continued

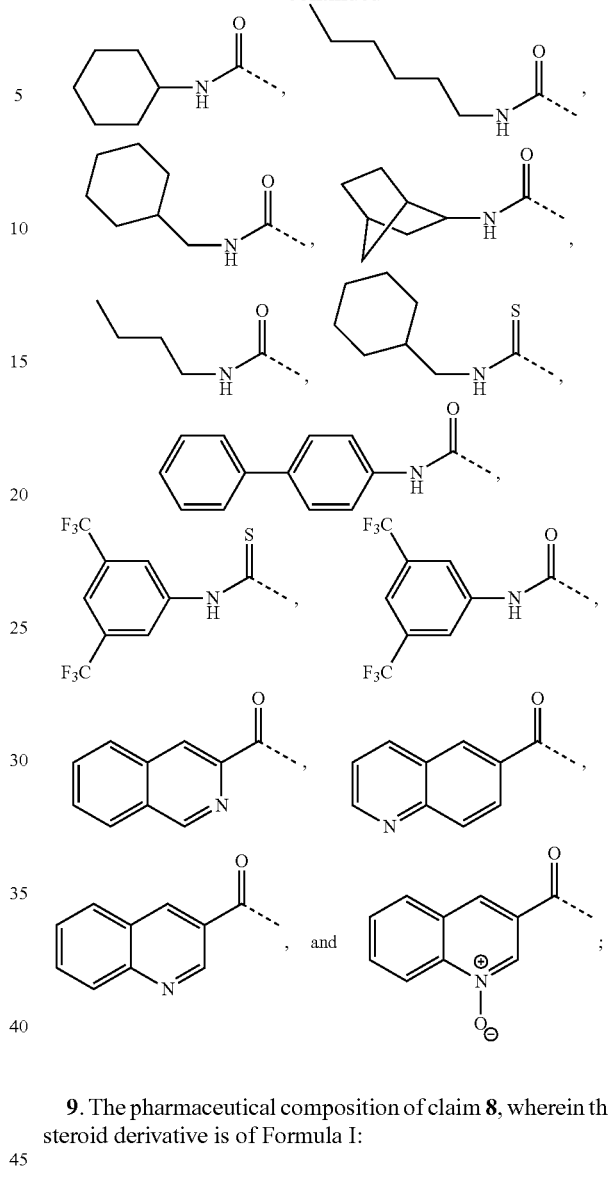

9. The pharmaceutical composition of claim 8, wherein the steroid derivative is of Formula I:

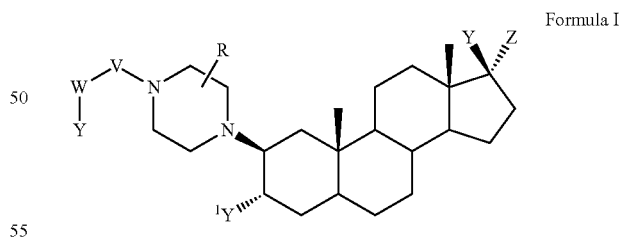

Formula I and wherein
  a) Y and $Y^1$ are OH and CHOHMe respectively;
  b) Z is H;
  c) R is H; and
  d) V is selected from the group consisting of L-proline, L-phenylalanine, D-proline, and D-phenylalanine; and
wherein the variables W and X are linked to form the linkage W—X, and wherein W—X is selected from the group consisting of

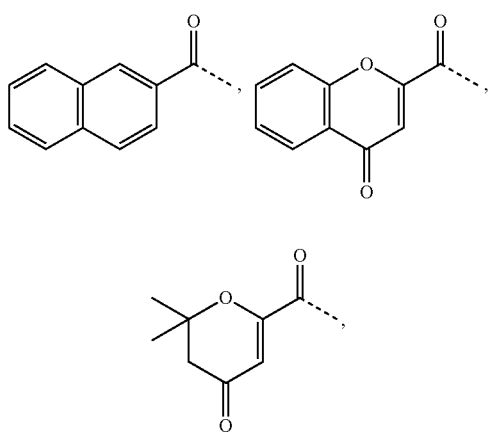
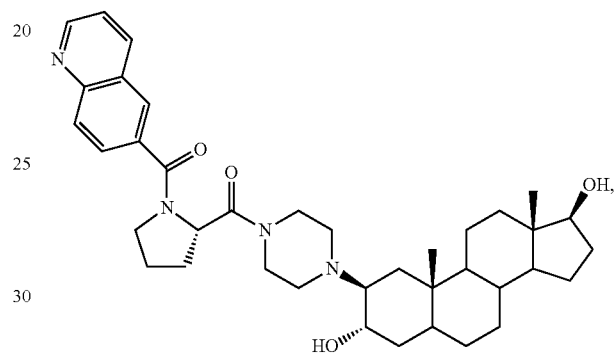
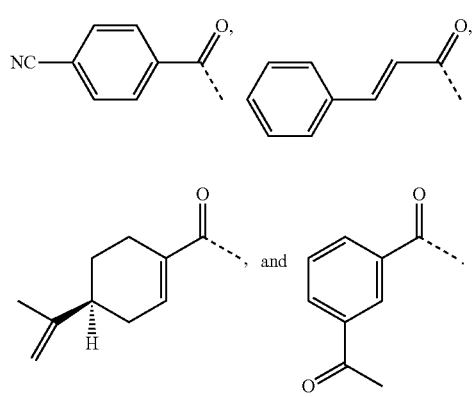
10. The pharmaceutical composition of claim 8, wherein the steroid derivative is,
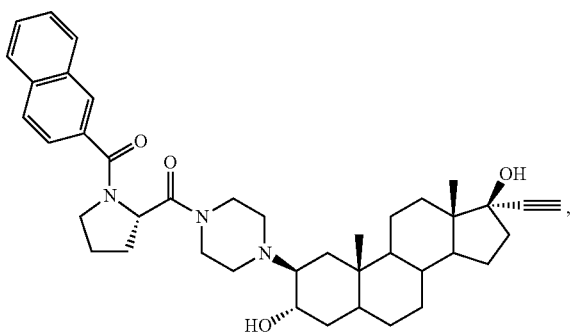
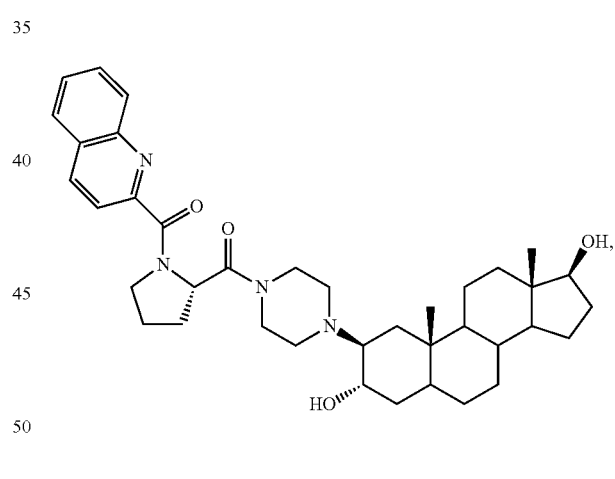
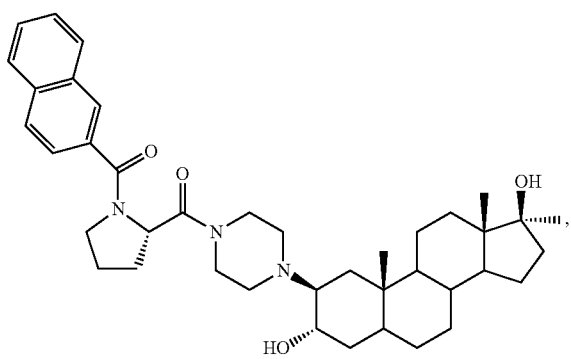
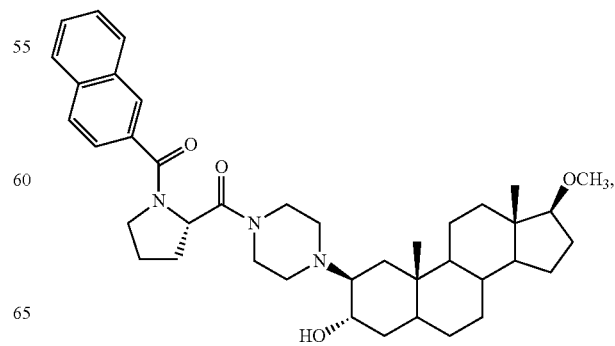

125
-continued
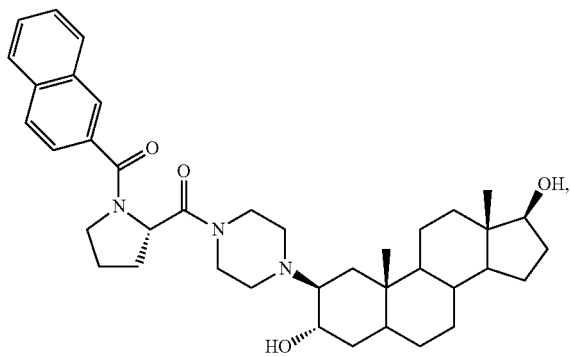
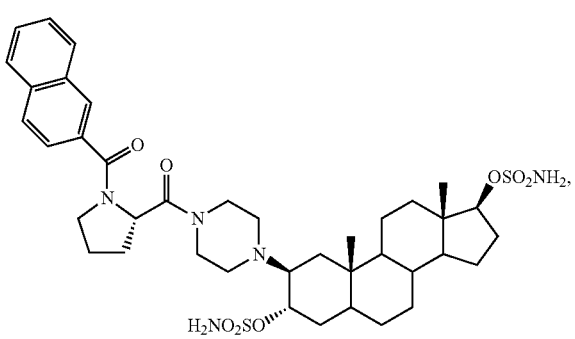
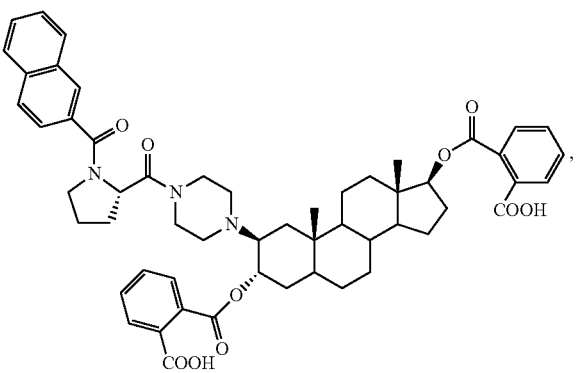
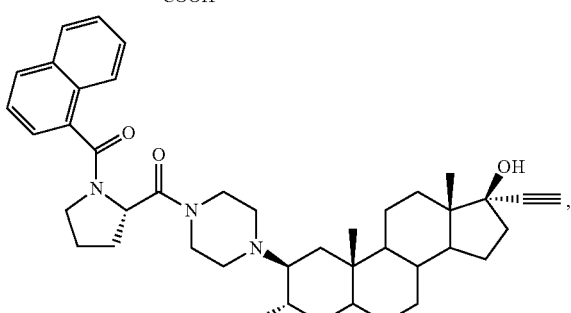
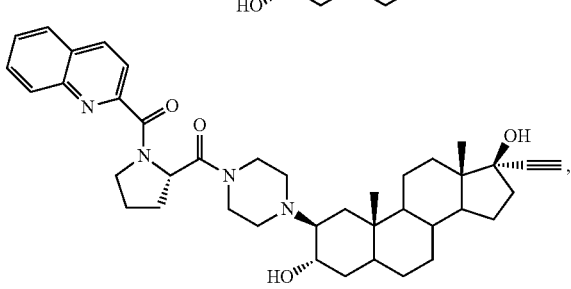
126
-continued
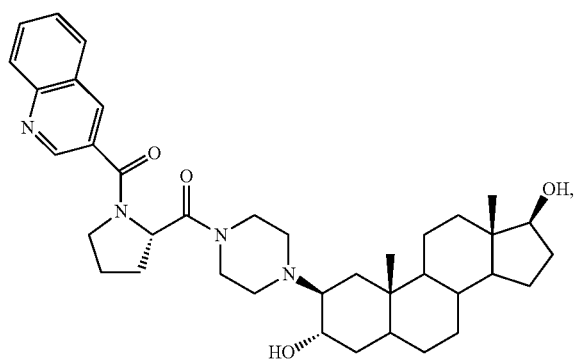
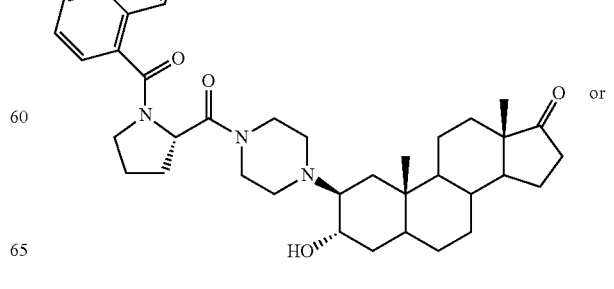

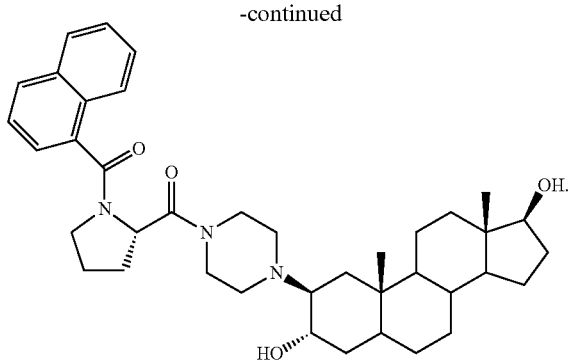
* * * * *